US012759968B2

(12) United States Patent
Silverman et al.

(10) Patent No.: US 12,759,968 B2
(45) Date of Patent: Oct. 13, 2026

(54) (S)-3-AMINO-4-(DIFLUOROMETHYLENE) CYCLOHEXENE AND CYCLOHEXANE CARBOXYLIC ACID AND USES THEREOF AS SELECTIVE INACTIVATORS OF HUMAN ORNITHINE AMINOTRANSFERASE (hOAT)

(71) Applicant: Northwestern University, Evanston, IL (US)

(72) Inventors: Richard B. Silverman, Evanston, IL (US); Wei Zhu, Evanston, IL (US)

(73) Assignee: Northwestern University, Evanston, IL (US)

( * ) Notice: Subject to any disclaimer, the term of this patent is extended or adjusted under 35 U.S.C. 154(b) by 308 days.

(21) Appl. No.: 18/554,265

(22) PCT Filed: Apr. 8, 2022

(86) PCT No.: PCT/US2022/024041
§ 371 (c)(1),
(2) Date: Oct. 6, 2023

(87) PCT Pub. No.: WO2022/217063
PCT Pub. Date: Oct. 13, 2022

(65) Prior Publication Data

US 2024/0239738 A1 Jul. 18, 2024

Related U.S. Application Data

(60) Provisional application No. 63/201,008, filed on Apr. 8, 2021.

(51) Int. Cl.
*C07C 229/48* (2006.01)
*A61K 31/196* (2006.01)

(52) U.S. Cl.
CPC .......... *C07C 229/48* (2013.01); *A61K 31/196* (2013.01); *C07B 2200/07* (2013.01); *C07C 2601/14* (2017.05); *C07C 2601/16* (2017.05)

(58) Field of Classification Search
CPC .. C07C 229/48; C07C 2601/16; A61K 31/196
USPC .......................................................... 514/561
See application file for complete search history.

(56) References Cited

U.S. PATENT DOCUMENTS

2016/0151316 A1 6/2016 Miller et al.
2018/0098952 A1 4/2018 Silverman et al.

FOREIGN PATENT DOCUMENTS

WO 2016073983 A2 5/2016
WO 2020206234 A1 10/2020

OTHER PUBLICATIONS

Zigmond et al., Suppression of Hepatocellular Carcinoma by Inhibition of Overexpressed Ornithine Aminotransferase, ACS Medicinal Chemistry Letters, vol. 6, No. 8, May 29, 2015.

Pubchem, SID 365844026, Available Date: May 25, 2018 [retrieved on Jul. 26, 2022].,Retrieved from the Internet <URL: https://pubchem.ncbi.nlm.nih.gov/substance/365844026>.

International Search Report and Written Opinion, corresponding to PCT/US2022/024041, dated Aug. 18, 2022.

Altman, B. J.; Stine, Z. E.; Dang, C. V., From Krebs to clinic: glutamine metabolism to cancer therapy. Nat Rev Cancer 2016, 16 (10), 619-34.

Boyd, S., Molecular operating environment. Chem World-Uk 2005, 2 (9), 66-66.

Briggs, S. W.; Mowrey, W.; Hall, C. B.; Galanopoulou, A. S., CPP-115, a vigabatrin analogue, decreases spasms in the multiple-hit rat model of infantile spasms. Epilepsia 2014, 55 (1), 94-102.

Butrin, A.; Beaupre, B. A.; Kadamandla, N.; Zhao, P.; Shen, S.; Silverman, R. B.; Moran, G. R.; Liu, D., Structural and Kinetic Analyses Reveal the Dual Inhibition Modes of Ornithine Aminotransferase by (1S,3S)-3-Amino-4-(hexafluoropropan-2-ylidenyl)-cyclopentane-1-carboxylic Acid (BCF3). Acs Chem Biol 2021, 16 (1), 67-75.

Cadoret, A.; Ovejero, C.; Terris, B.; Souil, E.; Levy, L.; Lamers, W. H.; Kitajewski, J.; Kahn, A.; Perret, C., New targets of beta-catenin signaling in the liver are involved in the glutamine metabolism. Oncogene 2002, 21 (54), 8293-8301.

Christensen, E. M.; Patel, S. M.; Korasick, D. A.; Campbell, A. C.; Krause, K. L.; Becker, D. F.; Tanner, J. J., Resolving the cofactor-binding site in the proline biosynthetic enzyme human pyrroline-5-carboxylate reductase 1. J Biol Chem 2017, 292 (17), 7233-7243.

Churchich, J. E.; Moses, U., 4-Aminobutyrate Aminotransferase—the Presence of Nonequivalent Binding-Sites. J Biol Chem 1981, 256 (3), 1101-1104.

Colnot, S .; Decaens, T.; Niwa-Kawakita, M.; Godard, C.; Hamard, G.; Kahn, A.; Giovannini, M.; Perret, C., Liver-targeted disruption of Apc in mice activates beta-catenin signaling and leads to hepatocellular carcinomas. P Natl Acad Sci USA 2004, 101 (49), 17216-17221.

Cooper, A. J. L., Glutamate-Gamma-Aminobutyrate Transaminase. Methods in Enzymology 1985, 113, 80-82.

De Lope, C. R.; Tremosini, S.; Forner, A.; Reig, M.; Bruix, J., Management of HCC. J Hepatol 2012, 56, S75-S87.

De Rosamel, L.; Blanc, J. F., Emerging tyrosine kinase inhibitors for the treatment of hepatocellular carcinoma. Expert Opin Emerg Dr 2017, 22 (2), 175-190.

(Continued)

*Primary Examiner* — Kahsay Habte
(74) *Attorney, Agent, or Firm* — Quarles & Brady LLP

(57) ABSTRACT

Disclosed are amino-substituted, halomethylene-substituted cyclohexene carboxylic acid compounds and amino-substituted, halomethylene-substituted cyclohexane carboxylic acid compounds. The disclosed compounds and compositions thereof may be utilized in methods for modulating human ornithine aminotransferase (AO AT) activity, including methods for treating diseases or disorders associated with AO AT activity or expression such as cell proliferative diseases and disorders including cancer.

18 Claims, 35 Drawing Sheets

Specification includes a Sequence Listing.

(56) References Cited

OTHER PUBLICATIONS

Dehart, C. J.; Fellers, R. T.; Fornelli, L.; Kelleher, N. L.; Thomas, P. M., Bioinformatics Analysis of Top-Down Mass Spectrometry Data with ProSight Lite. Methods Mol Biol 2017, 1558, 381-394.
Ding, Z.; Ericksen, R. E.; Escande-Beillard, N.; Lee, Q. Y.; Loh, A.; Denil, S.; Steckel, M.; Haegebarth, A.; Wai Ho, T. S.; Chow, P.; Toh, H. C.; Reversade, B.; Gruenewald, S.; Han, W., Metabolic pathway analyses identify proline biosynthesis pathway as a promoter of liver tumorigenesis. J Hepatol 2020, 72 (4), 725-735.
Doumlele, K.; Conway, E.; Hedlund, J.; Tolete, P.; Devinsky, O., A case report on the efficacy of vigabatrin analogue (1S, 3S)-3-amino-4-difluoromethylenyl-1-cyclopentanoic acid (CPP-115) in a patient with infantile spasms. Epilepsy Behav Case 2016, 6, 67-69.
Earley, L.; Anderson, L. C.; Bai, D. L.; Mullen, C.; Syka, J. E.; English, A. M.; Dunyach, J. J.; Stafford, G. C., Jr.; Shabanowitz, J.; Hunt, D. F.; Compton, P. D., Front-end electron transfer dissociation: a new ionization source. Anal Chem 2013, 85 (17), 8385-90.
Emsley, P.; Lohkamp, B.; Scott, W. G.; Cowtan, K., Features and development of Coot. Acta Crystallographica Section D-Biological Crystallography 2010, 66, 486-501.
Evans, P., Scaling and assessment of data quality. Acta Crystallogr D 2006, 62, 72-82.
Fellers, R. T.; Greer, J. B.; Early, B. P.; Yu, X.; LeDuc, R. D.; Kelleher, N. L.; Thomas, P. M., ProSight Lite: graphical software to analyze top-down mass spectrometry data. Proteomics 2015, 15 (7), 1235-8.
Galvez, J.; Guirado, A., A theoretical study of topomerization of imine systems: inversion, rotation or mixed mechanisms? J Comput Chem 2010, 31 (3), 520-31.
Ginguay, A.; Cynober, L.; Curis, E.; Nicolis, I., Ornithine Aminotransferase, an Important Glutamate-Metabolizing Enzyme at the Crossroads of Multiple Metabolic Pathways. Biology (Basel) 2017, 6 (1).
Grosse-Kunstleve, R. W.; Sauter, N. K.; Moriarty, N. W.; Adams, P. D., The Computational Crystallography Toolbox: crystallographic algorithms in a reusable software framework. J Appl Crystallogr 2002, 35, 126-136.
Heath, T. K.; Lutz, M. R.; Reidl, C. T.; Guzman, E. R.; Herbert, C. A.; Nocek, B. P.; Holz, R. C.; Olsen, K. W.; Ballicora, M. A.; Becker, D. P., Practical spectrophotometric assay for the dapE-encoded N-succinyl-L, L-diaminopimelic acid desuccinylase, a potential antibiotic target. Plos One 2018, 13 (4).
Herzfeld, A.; Knox, W. E., The properties, developmental formation, and estrogen induction of ornithine aminotransferase in rat tissues. J Biol Chem 1968, 243 (12), 3327-32.
Johnson, J. E.; Morales, N. M.; Gorczyca, A. M.; Dolliver, D. D.; McAllister, M. A., Mechanisms of acid-catalyzed Z/E isomerization of imines. J Org Chem 2001, 66 (24), 7979-7985.
Juncosa, J. I.; Lee, H.; Silverman, R. B., Two continuous coupled assays for ornithine-delta-aminotransferase. Anal Biochem 2013, 440 (2), 145-149.
Juncosa, J. I.; Takaya, K.; Le, H. V.; Moschitto, M. J.; Weerawarna, P. M.; Mascarenhas, R.; Liu, D. L.; Dewey, S. L.; Silverman, R. B., Design and Mechanism of (S)-3-Amino-4-(difluoromethylenyl)cyclopent-1-ene-1-carboxylic Acid, a Highly Potent gamma-Aminobutyric Acid Aminotransferase Inactivator for the Treatment of Addiction. J Am Chem Soc 2018, 140 (6), 2151-2164.
Kobayashi, K.; Miyazawa, S.; Endo, A., Isolation and Inhibitory Activity of Gabaculine, a New Potent Inhibitor of Gamma-Aminobutyrate Aminotransferase Produced by a Streptomyces. Febs Lett 1977, 76 (2), 207-210.
Layer, R. W., The Chemistry of Imines. Chem Rev 1963, 63 (5), 489-510.
Leathers, J. S.; Balderramo, D.; Prieto, J.; Diehl, F.; Gonzalez-Ballerga, E.; Ferreiro, M. R.; Carrera, E.; Barreyro, F.; Diaz-Ferrer, J.; Singh, D.; Mattos, A. Z.; Carrilho, F.; Debes, J. D., Sorafenib for Treatment of Hepatocellular Carcinoma A Survival Analysis From the South American Liver Research Network. J Clin Gastroenterol 2019, 53 (6), 464-469.
Lee, H.; Doud, E. H.; Wu, R.; Sanishvili, R.; Juncosa, J. I.; Liu, D. L.; Kelleher, N. L.; Silverman, R. B., Mechanism of Inactivation of gamma-Aminobutyric Acid Aminotransferase by (1S,3S)-3-Amino-4-difluoromethylene-1-cyclopentanoic Acid (CPP-115). J Am Chem Soc 2015, 137 (7), 2628-2640.
Lee, H.; Juncosa, J. I.; Silverman, R. B., Ornithine Aminotransferase versus GABA Aminotransferase: Implications for the Design of New Anticancer Drugs. Med Res Rev 2015, 35 (2), 286-305.
Liebschner, D.; Afonine, P. V.; Baker, M. L.; Bunkoczi, G.; Chen, V. B.; Croll, T. I.; Hintze, B.; Hung, L. W.; Jain, S.; McCoy, A. J.; Moriarty, N. W.; Oeffner, R. D.; Poon, B. K.; Prisant, M. G.; Read, R. J.; Richardson, J. S.; Richardson, D. C.; Sammito, M. D.; Sobolev, O. V.; Stockwell, D. H.; Terwilliger, T. C.; Urzhumtsev, A. G.; Videau, L. L.; Williams, C. J.; Adams, P. D., Macromolecular structure determination using X-rays, neutrons and electrons: recent developments in Phenix. Acta Crystallogr D 2019, 75, 861-877.
Liu Wei; Le Anne; Hancock Chad; Lane Andrew N; Dang Chi V; Fan Teresa W-M; Phang James M. Reprogramming of proline and glutamine metabolism contributes to the proliferative and metabolic responses regulated by oncogenic transcription factor c MYC. Proc. Natl. Acad. Sci. USA 2012, 109(23), 8983-8988.
Liu, F.; Lossl, P.; Scheltema, R.; Viner, R.; Heck, A. J. R., Optimized fragmentation schemes and data analysis strategies for proteome-wide cross-link identification. Nat Commun 2017, 8, 15473.
Liu, Y. F.; Wu, L.; Li, K.; Liu, F. R.; Wang, L.; Zhang, D. L.; Zhou, J.; Ma, X.; Wang, S. Y.; Yang, S. Y., Ornithine aminotransferase promoted the proliferation and metastasis of non-small cell lung cancer via upregulation of miR-21. J Cell Physiol 2019, 234 (8), 12828-12838.
Lucero OM, Dawson DW, Moon RT, et al. A re-evaluation of the “oncogenic” nature of Wnt/beta-catenin signaling in melanoma and other cancers. Curr Oncol Rep 2010, 12, 314-318.
Markova, M.; Peneff, C.; Hewlins, M. J. E.; Schirmer, T.; John, R. A., Determinants of substrate specificity in omega-aminotransferases. J Biol Chem 2005, 280 (43), 36409-36416.
Marty, M. T.; Baldwin, A. J.; Marklund, E. G.; Hochberg, G. K.; Benesch, J. L.; Robinson, C. V., Bayesian deconvolution of mass and ion mobility spectra: from binary interactions to polydisperse ensembles. Anal Chem 2015, 87 (8), 4370-6.
Mascarenhas, R.; Le, H. V.; Clevenger, K. D.; Lehrer, H. J.; Ringe, D.; Kelleher, N. L.; Silverman, R. B.; Liu, D., Selective Targeting by a Mechanism-Based Inactivator against Pyridoxal 5 '-Phosphate-Dependent Enzymes: MechanismS of Inactivation and Alternative Turnover. Biochemistry—Us 2017, 56 (37), 4951-4961.
Mccoy, A. J.; Grosse-Kunstleve, R. W.; Adams, P. D.; Winn, M. D.; Storoni, L. C.; Read, R. J., Phaser crystallographic software. J Appl Crystallogr 2007, 40, 658-674.
Mehta, P. K.; Hale, T. I.; Christen, P., Evolutionary Relationships among Aminotransferases—Tyrosine Aminotransferase, Histidinol-Phosphate Aminotransferase, and Aspartate-Aminotransferase Are Homologous Proteins. Eur J Biochem 1989, 186 (1-2), 249-253.
Milgrom, D. P.; Maluccio, M. A.; Koniaris, L. G., Management of Hepatocellular Carcinoma (HCC). Curr Surg Rep 2016, 4 (6).
Morris, G. M.; Huey, R.; Lindstrom, W.; Sanner, M. F.; Belew, R. K.; Goodsell, D. S.; Olson, A. J., AutoDock4 and AutoDockTools4: Automated Docking with Selective Receptor Flexibility. J Comput Chem 2009, 30 (16), 2785-2791.
Moschitto, M. J.; Doubleday, P. F.; Catlin, D. S.; Kelleher, N. L.; Liu, D. L.; Silverman, R. B., Mechanism of Inactivation of Ornithine Aminotransferase by (1S,3S)-3-Amino-4-(hexafluoropropan-2-ylidenyl)cyclopentane-1-carboxylic Acid. J Am Chem Soc 2019, 141 (27), 10711-10721.
Moschitto, M. J.; Silverman, R. B., Synthesis of (S)-3-Amino-4-(difluorornethylenyl)-cyclopent-1-ene-1-carboxylic Acid (OV329), a Potent Inactivator of gamma-Aminobutyric Acid Aminotransferase. Org Lett 2018, 20 (15), 4589-4592.
Nanavati, S. M.; Silverman, R. B., Mechanisms of Inactivation of Gamma-Aminobutyric-Acid Aminotransferase by the Antiepilepsy Drug Gamma-Vinyl Gaba (Vigabatrin). J Am Chem Soc 1991, 113 (24), 9341-9349.
Niedermeyer, T. H.; Strohalm, M., mMass as a software tool for the annotation of cyclic peptide tandem mass spectra. Plos One 2012, 7 (9), e44913.

(56) References Cited

OTHER PUBLICATIONS

Olsen, J. V.; Macek, B.; Lange, O.; Makarov, A.; Horning, S.; Mann, M., Higher-energy C-trap dissociation for peptide modification analysis. Nat Methods 2007, 4 (9), 709-12.

Pan, Y.; Gerasimov, M. R.; Kvist, T.; Wellendorph, P.; Madsen, K. K.; Pera, E.; Lee, H.; Schousboe, A.; Chebib, M.; Brauner-Osborne, H.; Craft, C. M.; Brodie, J. D.; Schiffer, W. K.; Dewey, S. L.; Miller, S. R.; Silverman, R. B., (1S, 3S)-3-Amino-4-difluoromethylenyl-1-cyclopentanoic Acid (CPP-115), a Potent gamma-Aminobutyric Acid Aminotransferase Inactivator for the Treatment of Cocaine Addiction. J Med Chem 2012, 55 (1), 357-366.

Pan, Y.; Qiu, J.; Silverman, R. B., Design, synthesis, and biological activity of a difluoro-substituted, conformationally rigid vigabatrin analogue as a potent gamma-aminobutyric acid aminotransferase inhibitor. J Med Chem 2003, 46 (25), 5292-5293.

Peraino, C.; Bunville, L. G.; Tahmisia.Tn, Chemical Physical and Morphological Properties of Ornithine Aminotransferase from Rat Liver. J Biol Chem 1969, 244 (9), 2241-9.

Personeni, N.; Rimassa, L., Hepatocellular Carcinoma: A Global Disease in Need of Individualized Treatment Strategies. J Oncol Pract 2017, 13 (6), 368-370.

Pettersen, E. F.; Goddard, T. D.; Huang, C. C.; Couch, G. S.; Greenblatt, D. M.; Meng, E. C.; Ferrin, T. E., UCSF chimera—A visualization system for exploratory research and analysis. J Comput Chem 2004, 25 (13), 1605-1612.

Phang, J. M.; Liu, W.; Hancock, C. N.; Fischer, J. W., Proline metabolism and cancer: emerging links to glutamine and collagen. Curr Opin Clin Nutr Metab Care 2015, 18 (1), 71-7.

Phang, J. M.; Liu, W.; Zabirnyk, O., Proline metabolism and microenvironmental stress. Annu Rev Nutr 2010, 30, 441-63.

Pronk, S.; Pall, S.; Schulz, R.; Larsson, P.; Bjelkmar, P.; Apostolov, R.; Shirts, M. R.; Smith, J. C.; Kasson, P. M.; van der Spoel, D.; Hess, B.; Lindahl, E., Gromacs 4.5: a high-throughput and highly parallel open source molecular simulation toolkit. Bioinformatics 2013, 29 (7), 845-54.

Rando, R. R., Mechanism of Irreversible Inhibition of Gamma-Aminobutyric Acid-Alpha-Ketoglutaric Acid Transaminase by Neurotoxin Gabaculine. Biochemistry—Us 1977, 16 (21), 4604-4610.

Rando, R. R., Mechanism-Based Enzyme Inactivators. Pharmacol Rev 1984, 36 (2), 111-142.

Sayiner, M.; Golabi, P.; Younossi, Z. M., Disease Burden of Hepatocellular Carcinoma: A Global Perspective. Digest Dis Sci 2019, 64 (4), 910-917.

Shah, S. A.; Shen, B. W.; Brunger, A. T., Human ornithine aminotransferase complexed with L-canaline and gabaculine: structural basis for substrate recognition. Structure 1997, 5 (8), 1067-1075.

Shen, B. W.; Hennig, M.; Hohenester, E.; Jansonius, J. N.; Schirmer, T., Crystal structure of human recombinant ornithine aminotransferase. J Mol Biol 1998, 277 (1), 81-102.

Shen, S. D.; Doubleday, P. F.; Weerawarna, P. M.; Zhu, W.; Kelleher, N. L.; Silverman, R. B., Mechanism-Based Design of 3-Amino-4-Halocyclopentenecarboxylic Acids as Inactivators of GABA Aminotransferase. Acs Med Chem Lett 2020, 11 (10), 1949-1955.

Sherman, M.; Bruix, J.; Porayko, M.; Tran, T.; Comm, A. P. G., Screening for hepatocellular carcinoma: The rationale for the American Association for the Study of Liver Diseases recommendations. Hepatology 2012, 56 (3), 793-796.

Silverman, R. B., Design and Mechanism of GABA Aminotransferase Inactivators. Treatments for Epilepsies and Addictions. Chemical Reviews 2018, 118 (7), 4037-4070.

Silverman, R. B., Mechanism-Based Enzyme Inactivators. Method Enzymol 1995, 249, 240-283.

Silverman, R., CPP-115: A novel GABA aminotransferase inactivator and potential new treatment for epilepsy, addiction, and hepatocellular carcinoma. Abstr Pap Am Chem S 2016, 252.

Sivenius, M. R.; Ylinen, A.; Murros, K.; Matilainen, R.; Riekkinen, P., Double-blind dose reduction study of vigabatrin in complex partial epilepsy. Epilepsia 1987, 28 (6), 688-92.

Skinner, O. S.; Haverland, N. A.; Fornelli, L.; Melani, R. D.; Do Vale, L. H. F.; Seckler, H. S.; Doubleday, P. F.; Schachner, L. F.; Srzentic, K.; Kelleher, N. L.; Compton, P. D., Top-down characterization of endogenous protein complexes with native proteomics. Nat Chem Biol 2018, 14 (1), 36-41.

Sousa da Silva, A. W.; Vranken, W. F., ACPYPE—AnteChamber PYthon Parser interfacE. BMC Res Notes 2012, 5, 367.

Storici, P.; Capitani, G.; Muller, R.; Schirmer, T.; Jansonius, J. N., Crystal structure of human ornithine aminotransferase complexed with the highly specific and potent inhibitor 5-fluoromethylornithine. J Mol Biol 1999, 285 (1), 297-309.

Tang, L.; Zeng, J.; Geng, P.; Fang, C.; Wang, Y.; Sun, M.; Wang, C.; Wang, J.; Yin, P.; Hu, C.; Guo, L.; Yu, J.; Gao, P.; Li, E.; Zhuang, Z.; Xu, G.; Liu, Y., Global Metabolic Profiling Identifies a Pivotal Role of Proline and Hydroxyproline Metabolism in Supporting Hypoxic Response in Hepatocellular Carcinoma. Clin Cancer Res 2018, 24 (2), 474-485.

Tong, Xuemei; Zhao, Fangping; Thompson, Craig B. The molecular determinants of de novo nucleotide biosynthesis in cancer cells. Curr. Opin. Genet. Devel. 2009, 19(1), 32-37.

Towns, J.; Cockerill, T.; Dahan, M.; Foster, I.; Gaither, K.; Grimshaw, A.; Hazlewood, V.; Lathrop, S.; Lifka, D.; Peterson, G. D.; Roskies, R.; Scott, J. R.; Wilkins-Diehr, N., Xsede: Accelerating Scientific Discovery. Comput Sci Eng 2014, 16 (5), 62-74.

Traven', V. F.; Ivanov, I. V.; Panov, A. V.; Safronova, O. B.; Chibisova, T. A., Solvent-induced E/Z(C=N)-isomerization of imines of some hydroxy-substituted formylcoumarins. Russian Chemical Bulletin 2008, 57 (9), 1989-1995.

Vilar, S.; Cozza, G.; Moro, S., Medicinal Chemistry and the Molecular Operating Environment (MOE): Application of QSAR and Molecular Docking to Drug Discovery. Curr Top Med Chem 2008, 8 (18), 1555-1572.

Walsh, C. T., Suicide Substrates, Mechanism Based Enzyme Inactivators—Recent Developments. Annu Rev Biochem 1984, 53, 493-535.

Wang, J. M.; Wang, W.; Kollman, P. A.; Case, D. A., Automatic atom type and bond type perception in molecular mechanical calculations. J Mol Graph Model 2006, 25 (2), 247-260.

Wheless, J. W.; Ramsay, R. E.; Collins, S. D., Vigabatrin. Neurotherapeutics 2007, 4 (1), 163-172.

Winter, G.; Waterman, D. G.; Parkhurst, J. M.; Brewster, A. S.; Gildea, R. J.; Gerstel, M.; Fuentes-Montero, L.; Vollmar, M.; Michels-Clark, T.; Young, I. D.; Sauter, N. K.; Evans, G., Dials: implementation and evaluation of a new integration package. Acta Crystallogr D 2018, 74, 85-97.

Yang, J. D.; Roberts, L. R., Hepatocellular carcinoma: a global view. Nat Rev Gastro Hepat 2010, 7 (8), 448-458.

Yeung, Y. Y.; Hong, S.; Corey, E. J., A short enantioselective pathway for the synthesis of the anti-influenza neuramidase inhibitor oseltamivir from 1,3-butadiene and acrylic acid. J Am Chem Soc 2006, 128 (19), 6310-1.

Zhu, W.; Doubleday, P. F.; Catlin, D. S.; Weerawarna, P. M.; Butrin, A.; Shen, S.; Wawrzak, Z.; Kelleher, N. L.; Liu, D.; Silverman, R. B., A Remarkable Difference That One Fluorine Atom Confers on the Mechanisms of Inactivation of Human Ornithine Aminotransferase by Two Cyclohexene Analogues of gamma-Aminobutyric Acid. J Am Chem Soc 2020, 142 (10), 4892-4903.

Zubarev, R. A.; Horn, D. M.; Fridriksson, E. K.; Kelleher, N. L.; Kruger, N. A.; Lewis, M. A.; Carpenter, B. K.; McLafferty, F. W., Electron capture dissociation for structural characterization of multiply charged protein cations. Anal Chem 2000, 72 (3), 563-73.

Zhu et al. Remarkable, Unexpected Mechanism for (S)-3-Amino-4-(Difluoromethylenyl)cyclohex-1-Ene-1-Carboxylic Acid as a Selective Inactivator of Human Ornithine Aminotransferase. J Am Chem Soc. 2021, 143(21), 8193-8207.

Zhu et al. Rational Design, Synthesis, and Mechanism of (3S,4R)-3-Amino-4-(difluoromethyl)cyclopent-1-ene-1-carboxylic Acid Employing a Second-Deprotonation Strategy for Selectivity of Human Ornithine Aminotransferase over gamma-Aminobutyric Acid Aminotransferase. J Am Chem Soc. 2022, 144(12), 5629-5642.

Qiu, Jian; Silverman, Richard B. A New Class of Conformationally Rigid Analogs of 4-Amino-5-halopentanoic Acids, Potent Inactivators of gamma-Aminobutyric Acid Aminotransferase. Journal of Medicinal Chemistry (2000), 43(4), 706-720.

9

10

11a, X = H
11b, X = F

Figure 4C

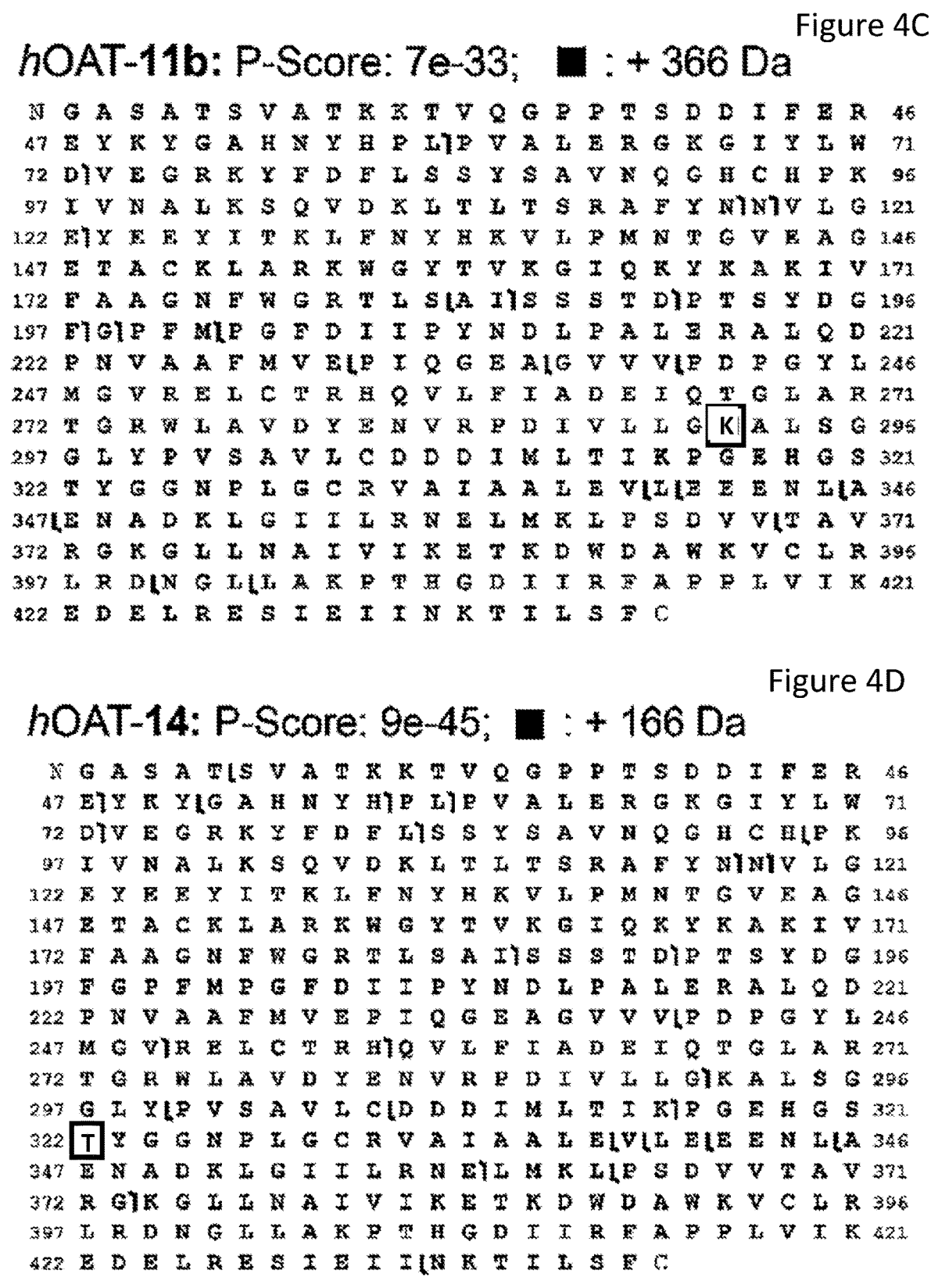

*h*OAT-11b: P-Score: 7e-33; ■ : + 366 Da

N G A S A T S V A T K K T V Q G P P T S D D I F E R 46
47 E Y K Y G A H N Y H P L P V A L E R G K G I Y L W 71
72 D V E G R K Y F D F L S S Y S A V N Q G H C H P K 96
97 I V N A L K S Q V D K L T L T S R A F Y N N V L G 121
122 E Y E E Y I T K L F N Y H K V L P M N T G V E A G 146
147 E T A C K L A R K W G Y T V K G I Q K Y K A K I V 171
172 F A A G N F W G R T L S A I S S S T D P T S Y D G 196
197 F G P F M P G F D I I P Y N D L P A L E R A L Q D 221
222 P N V A A F M V E P I Q G E A G V V V P D P G Y L 246
247 M G V R E L C T R H Q V L F I A D E I Q T G L A R 271
272 T G R W L A V D Y E N V R P D I V L L G K A L S G 296
297 G L Y P V S A V L C D D D I M L T I K P G E H G S 321
322 T Y G G N P L G C R V A I A A L E V L E E E N L A 346
347 E N A D K L G I I L R N E L M K L P S D V V T A V 371
372 R G K G L L N A I V I K E T K D W D A W K V C L R 396
397 L R D N G L L A K P T H G D I I R F A P P L V I K 421
422 E D E L R E S I E I I N K T I L S F C

Figure 4D

*h*OAT-14: P-Score: 9e-45; ■ : + 166 Da

N G A S A T S V A T K K T V Q G P P T S D D I F E R 46
47 E Y K Y G A H N Y H P L P V A L E R G K G I Y L W 71
72 D V E G R K Y F D F L S S Y S A V N Q G H C H P K 96
97 I V N A L K S Q V D K L T L T S R A F Y N N V L G 121
122 E Y E E Y I T K L F N Y H K V L P M N T G V E A G 146
147 E T A C K L A R K W G Y T V K G I Q K Y K A K I V 171
172 F A A G N F W G R T L S A I S S S T D P T S Y D G 196
197 F G P F M P G F D I I P Y N D L P A L E R A L Q D 221
222 P N V A A F M V E P I Q G E A G V V V P D P G Y L 246
247 M G V R E L C T R H Q V L F I A D E I Q T G L A R 271
272 T G R W L A V D Y E N V R P D I V L L G K A L S G 296
297 G L Y P V S A V L C D D D I M L T I K P G E H G S 321
322 T Y G G N P L G C R V A I A A L E V L E E E N L A 346
347 E N A D K L G I I L R N E L M K L P S D V V T A V 371
372 R G K G L L N A I V I K E T K D W D A W K V C L R 396
397 L R D N G L L A K P T H G D I I R F A P P L V I K 421
422 E D E L R E S I E I I N K T I L S F C

Figure 13A (Cont.)

Control *h*OAT

N G A S A T S V A T K K T V Q G P P T S D D I F E R 46

47 E Y K Y G A H N Y H P L P V A L E R G K G I Y L W 71

72 D V E G R K Y F D F L S S Y S A V N Q G H C H P K 96

97 I V N A L K S Q V D K L T L T S R A F Y N N V L G 121

122 E Y E E Y I T K L F N Y H K V L P M N T G V E A G 146

147 E T A C K L A R K W G Y T V K G I Q K Y K A K I V 171

172 F A A G N F W G R T L S A I S S S T D P T S Y D G 196

197 F G P F M P G F D I I P Y N D L P A L E R A L Q D 221

222 P N V A A F M V E P I Q G E A G V V V P D P G Y L 246

247 M G V R E L C T R H Q V L F I A D E I Q T G L A R 271

272 T G R W L A V D Y E N V R P D I V L L G K A L S G 296

297 G L Y P V S A V L C D D D I M L T I K P G E H G S 321

322 T Y G G N P L G C R V A I A A L E V L E E E N L A 346

347 E N A D K L G I I L R N E L M K L P S D V V T A V 371

372 R G K G L L N A I V I K E T K D W D A W K V C L R 396

397 L R D N G L L A K P T H G D I I R F A P P L V I K 421

422 E D E L R E S I E I I N K T I L S F C

Figure 13B (Cont.)

hOAT-14

N G A S A T S V A T K K T V Q G P P T S D D I F E R 46
47 E Y K Y G A H N Y H P L P V A L E R G K G I Y L W 71
72 D V E G R K Y F D F L S S Y S A V N Q G H C H P K 96
97 I V N A L K S Q V D K L T L T S R A F Y N N V L G 121
122 E Y E E Y I T K L F N Y H K V L P M N T G V E A G 146
147 E T A C K L A R K W G Y T V K G I Q K Y K A K I V 171
172 F A A G N F W G R T L S A I S S S T D P T S Y D G 196
197 F G P F M P G F D I I P Y N D L P A L E R A L Q D 221
222 P N V A A F M V E P I Q G E A G V V V P D P G Y L 246
247 M G V R E L C T R H Q V L F I A D E I Q T G L A R 271
272 T G R W L A V D Y E N V R P D I V L L G K A L S G 296
297 G L Y P V S A V L C D D D I M L T I K P G E H G S 321
322 T Y G G N P L G C R V A I A A L E V L E E E N L A 346
347 E N A D K L G I I L R N E L M K L P S D V V T A V 371
372 R G K G L L N A I V I K E T K D W D A W K V C L R 396
397 L R D N G L L A K P T H G D I I R F A P P L V I K 421
422 E D E L R E S I E I I N K T I L S F C

SEQUENCE LISTING

```
<160> NUMBER OF SEQ ID NOS: 1

<210> SEQ ID NO 1
<211> LENGTH: 418
<212> TYPE: PRT
<213> ORGANISM: Artificial Sequence
<220> FEATURE:
<223> OTHER INFORMATION: Synthetic - Portion of the human ornithine
      aminotransferase (hOAT) protein shown in Figures 4B-4D and Figures
      13A-13B

<400> SEQUENCE: 1

Gly Ala Ser Ala Thr Ser Val Ala Thr Lys Lys Thr Val Gln Gly Pro
1               5                   10                  15

Pro Thr Ser Asp Asp Ile Phe Glu Arg Glu Tyr Lys Tyr Gly Ala His
            20                  25                  30

Asn Tyr His Pro Leu Pro Val Ala Leu Glu Arg Gly Lys Gly Ile Tyr
        35                  40                  45

Leu Trp Asp Val Glu Gly Arg Lys Tyr Phe Asp Phe Leu Ser Ser Tyr
    50                  55                  60

Ser Ala Val Asn Gln Gly His Cys His Pro Lys Ile Val Asn Ala Leu
65                  70                  75                  80

Lys Ser Gln Val Asp Lys Leu Thr Leu Thr Ser Arg Ala Phe Tyr Asn
                85                  90                  95

Asn Val Leu Gly Glu Tyr Glu Glu Tyr Ile Thr Lys Leu Phe Asn Tyr
            100                 105                 110

His Lys Val Leu Pro Met Asn Thr Gly Val Glu Ala Gly Glu Thr Ala
        115                 120                 125

Cys Lys Leu Ala Arg Lys Trp Gly Tyr Thr Val Lys Gly Ile Gln Lys
    130                 135                 140
```

-continued

```
Tyr Lys Ala Lys Ile Val Phe Ala Ala Gly Asn Phe Trp Gly Arg Thr
145                 150                 155                 160

Leu Ser Ala Ile Ser Ser Ser Thr Asp Pro Thr Ser Tyr Asp Gly Phe
                165                 170                 175

Gly Pro Phe Met Pro Gly Phe Asp Ile Ile Pro Tyr Asn Asp Leu Pro
            180                 185                 190

Ala Leu Glu Arg Ala Leu Gln Asp Pro Asn Val Ala Ala Phe Met Val
        195                 200                 205

Glu Pro Ile Gln Gly Glu Ala Gly Val Val Val Pro Asp Pro Gly Tyr
    210                 215                 220

Leu Met Gly Val Arg Glu Leu Cys Thr Arg His Gln Val Leu Phe Ile
225                 230                 235                 240

Ala Asp Glu Ile Gln Thr Gly Leu Ala Arg Thr Gly Arg Trp Leu Ala
                245                 250                 255

Val Asp Tyr Glu Asn Val Arg Pro Asp Ile Val Leu Leu Gly Lys Ala
            260                 265                 270

Leu Ser Gly Gly Leu Tyr Pro Val Ser Ala Val Leu Cys Asp Asp Asp
        275                 280                 285

Ile Met Leu Thr Ile Lys Pro Gly Glu His Gly Ser Thr Tyr Gly Gly
    290                 295                 300

Asn Pro Leu Gly Cys Arg Val Ala Ile Ala Ala Leu Glu Val Leu Glu
305                 310                 315                 320

Glu Glu Asn Leu Ala Glu Asn Ala Asp Lys Leu Gly Ile Ile Leu Arg
                325                 330                 335

Asn Glu Leu Met Lys Leu Pro Ser Asp Val Val Thr Ala Val Arg Gly
            340                 345                 350

Lys Gly Leu Leu Asn Ala Ile Val Ile Lys Glu Thr Lys Asp Trp Asp
        355                 360                 365

Ala Trp Lys Val Cys Leu Arg Leu Arg Asp Asn Gly Leu Leu Ala Lys
    370                 375                 380

Pro Thr His Gly Asp Ile Ile Arg Phe Ala Pro Pro Leu Val Ile Lys
385                 390                 395                 400

Glu Asp Glu Leu Arg Glu Ser Ile Glu Ile Ile Asn Lys Thr Ile Leu
                405                 410                 415

Ser Phe
```

(S)-3-AMINO-4-(DIFLUOROMETHYLENE) CYCLOHEXENE AND CYCLOHEXANE CARBOXYLIC ACID AND USES THEREOF AS SELECTIVE INACTIVATORS OF HUMAN ORNITHINE AMINOTRANSFERASE (hOAT)

CROSS-REFERENCE TO RELATED APPLICATIONS

This application represents the national stage entry of PCT/US2022/024041 filed Apr. 8, 2022, which claims benefit of priority to U.S. Patent Application No. 63/201,008, filed Apr. 8, 2021. The contents of each are incorporated by reference in their entireties.

STATEMENT REGARDING FEDERALLY SPONSORED RESEARCH OR DEVELOPMENT

This invention was made with government support under DA030604 awarded by the National Institutes of Health. The government has certain rights in the invention.

REFERENCE TO A SEQUENCE LISTING

This application is being filed electronically via EFS-Web and includes an electronically submitted Sequence Listing in .txt format. The .txt file contains a sequence listing entitled “702581_02111_ST25. txt” created on Apr. 4, 2022 and is 4,198 bytes in size. The Sequence Listing contained in this .txt file is part of the specification and is hereby incorporated by reference herein in its entirety.

BACKGROUND

Liver cancer is the sixth most common cancer and the second leading cause of cancer-related deaths. Among all primary liver cancers, hepatocellular carcinoma (HCC) is the most common neoplasm, accounting for approximately 85-90% of cases. To date, only four small molecules are available on the market as treatment options for HCC, while they lack target selectivity, thereby resulting in various off-target effects and drug resistance. Therefore, there is a significant unmet need for this area. The human ornithine d-aminotransferase (hOAT) gene was found to be overexpressed in liver cancer tissues, while pharmacological inhibition of hOAT leads to promising tumor growth reduction. Therefore, the discovery of hOAT inhibitors may provide a novel therapeutic approach for HCC. In this work, we identified (S)-3-amino-4-(difluoromethylene)cyclohex-1-ene-1-carboxylic acid (WZ-1-181, 14) as a potent and selective inactivator of hOAT. Moreover, the preliminary assessment suggests that WZ-1-181 exhibits favorable DMPK properties, and it is being investigated in the PDX mouse models of HCC.

SUMMARY

Disclosed are compounds, compositions, and related methods of use for the selective inhibition of human ornithine aminotransferase. The disclosed compounds, compositions, and methods can be utilized to treat diseases and disorders associated with human ornithine aminotransferase activity such as cell proliferation diseases and disorders such as cancer.

The disclosed compounds may be described as substituted methylenecyclohexene and substituted methylenecyclohexane compounds. In particular, the disclosed compounds may be described as amino-substituted, halomethylene-substituted cyclohexene carboxylic acid compounds and amino-substituted, halomethylene-substituted cyclohexane carboxylic acid compounds. The disclosed compounds and compositions thereof may be utilized in methods for modulating human ornithine aminotransferase (hOAT) activity, including methods for treating diseases or disorders associated with hOAT activity or expression such as cell proliferative diseases and disorders including cancer.

The disclosed compounds may be directed to a compound of the following formula or a dissociated form, a non-protonated form, a zwitterion form, or a salt thereof:

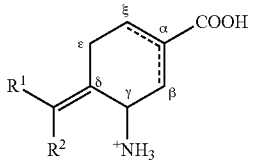

wherein a double bond is optionally present between the α and ζ carbons or wherein a double bond is optionally present between the α and β carbons, and the compound has a formula:

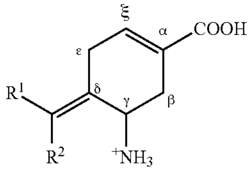

or

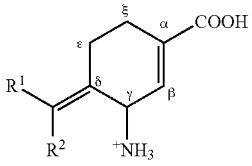

or

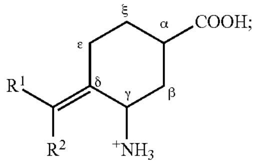

wherein each of $R^1$ and $R^2$ is a halogen such as F, Cl, Br, and I (e.g., F).

In some embodiments, the disclosed compounds may be directed to a compound of the following formula or a dissociated form, a non-protonated form, a zwitterion form, or a salt thereof:

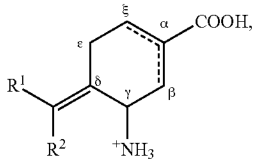

wherein a double bond is present between the α and ζ carbons or a double bond is present between the α and β carbons, wherein each of $R^1$ and $R^2$ is a halogen such as F, Cl, Br, and I (e.g., F).

In other embodiments, the compound is a compound of the following formula or a dissociated form, a non-protonated form, a zwitterion form, or a salt thereof:

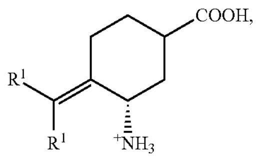

wherein each of $R^1$ and $R^2$ is a halogen such as F, Cl, Br, and I (e.g., F).

In certain embodiments, the compound is a compound of the following formula or a dissociated form, a non-protonated form, a zwitterion form, or a salt thereof:

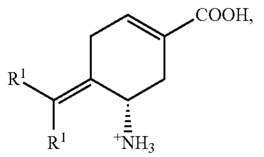

wherein each of $R^1$ and $R^2$ is a halogen such as F, Cl, Br, and I (e.g., F).

In certain embodiments, the compound is a compound of the following formula or a dissociated form, a non-protonated form, a zwitterion form, or a salt thereof:

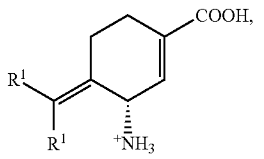

wherein each of $R^1$ and $R^2$ is a halogen such as F, Cl, Br, and I (e.g., F).

As indicated, the disclosed compounds may be protonated, for example to form an ammonium moiety, optionally where the compound is present as a salt (e.g., an ammonium salt). The disclosed compounds also may be non-protonated and/or dissociated, for example, where the carboxylic acid moiety is dissociated to form a carboxylate moiety, optionally where the compound is present as a salt (e.g., a carboxylate salt). The disclosed compounds may be in zwitterionic form where the compound comprises a protonated ammonium moiety and a dissociated carboxylate moiety, optionally where the compound is present as a salt.

The disclosed compounds and compositions may be utilized in methods for modulating human ornithine aminotransferase (hOAT) activity. Such methods can comprise providing a compound as disclosed herein, such as a compound of the following formula or a dissociated form, a zwitterion form, or a salt thereof, and contacting hOAT with the compound:

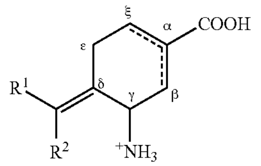

wherein a double bond is optionally present between the α and ζ carbons or wherein a double bond is optionally present between the α and β carbons, wherein each of $R^1$ and $R^2$ is a halogen such as F, Cl, Br, and I (e.g., F). In certain embodiments, no double bond is present between the α and ζ carbons and no double bond is presented between the α and β carbons. In certain embodiments, the double bond is between the α and ζ carbons. In other embodiments, the double bond is between the α and β carbons. In certain embodiments, $R^1$ and $R^2$ are F.

In certain embodiments, the disclosed methods may be directed to reducing activity of an hOAT expressed by a cancer, which may include but is not limited to hepatocellular cancer (HCC), non-small cell lung cancer (NSCLC), and colorectal cancer, or other cancers that express or overexpress hOAT. Such a method can comprise providing a compound as disclosed herein, such as a compound of the following formula or a dissociated form, a non-protonated form, a zwitterion form, or a salt thereof, and contacting the cancer with the compound:

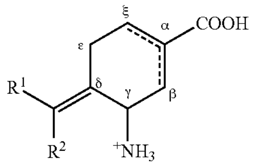

wherein a double bond is optionally present between the α and ζ carbons or wherein a double bond is optionally present between the α and β carbons, wherein each of $R^1$ and $R^2$ is a halogen such as F, Cl, Br, and I (e.g., F). In certain embodiments, no double bond is present between the α and ζ carbons and no bond is presented between the α and β carbons. In certain embodiments, the double bond is between the α and ζ carbons. In other embodiments, the double bond is between the α and β carbons. In certain embodiments, $R^1$ and $R^2$ are F.

In certain embodiments, the disclosed methods may be directed to treating a cell proliferative disease or disorder in a subject in need thereof, which methods comprise administering an effective amount of the compounds disclosed herein or pharmaceutical compositions comprising an effective amount of the compounds disclosed herein for treating the cell proliferative disease or disorder. Suitable cell proliferative diseases and disorders may include cancers that express or overexpress hOAT such as, but not limited to, hepatocellular carcinoma (HCC), non-small cell lung cancer (NSCLC), and colorectal cancer. Such a method can comprise administering to such a subject in need thereof an effective amount of a compound of the following formula or a dissociated form, a non-protonated form, a zwitterion form, or a salt thereof (or a pharmaceutical composition comprising an effective amount of the compound, a dissociated form, a non-protonated form, a zwitterion form, or a salt thereof:

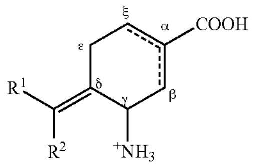

wherein a double bond is optionally present between the α and ζ carbons or wherein the double bond is optionally present between the α and β carbons, wherein each of $R^1$ and $R^2$ is independently selected from a halogen such as F, Cl, Br, and I (e.g., F). In certain embodiments, no double bond is present between the α and ζ carbons and no double bond is present between the α and β carbons. In certain embodiments, the double bond is between the α and ζ carbons. In other embodiments, the double bond is between the α and β carbons. In certain embodiments, $R^1$ and $R^2$ are F.

The compounds disclosed herein are without stereochemical or configurational limitation and encompass all stereochemical or configurational isomers, unless stereochemical or configurational limitations are indicated. As illustrated and discussed below, such compounds and/or their intermediates are available as single enantiomers, racemic mixtures from which isomers can be resolved, or diastereomers from which the corresponding enantiomers can be separated. Accordingly, any stereocenter can be (S) or (R) with respect to any other stereocenter(s). As another separate consideration, various compounds can be present as an acid or base salt, either partially or fully protonated, for example at the amino group to form an ammonium moiety, and/or either partially or fully dissociated, for example at the carboxyl group to form a carboxylate substituent or moiety. In certain such embodiments, with respect to an ammonium substituent or moiety, the counter ion can be a conjugate base of a protic acid. In certain such or other embodiments, with respect to a carboxylate substituent or moiety, the counter ion can be an alkaline, alkaline-earth or ammonium cation. Further, it will be understood by those skilled in the art that any one or more the compounds disclosed herein can be provided as part of a pharmaceutical composition comprising a pharmaceutically-acceptable carrier component for use in conjunction with a treatment method or medicament.

In certain embodiments, the disclosed methods are directed to a disease or disorder associated with hOAT activity and/or expression or overexpression, including cell proliferative diseases and disorders such as cancers associated with hOAT activity and/or expression or overexpression. Suitable diseases and disorders may include, but are not limited to cell proliferative diseases and disorders, which may include but are not limited to hepatocellular carcinoma (HCC), non-small cell lung cancer (NSCLC), and colorectal cancer in a human subject in need of such a treatment. In certain embodiments, such a compound can be provided as part of a pharmaceutical composition.

In certain embodiments, the disclosed methods are directed to reducing or modulating activity of an ornithine aminotransferase expressed by a cancer (e.g., hepatocellular carcinoma (HCC), non-small cell lung cancer (NSCLC)), and colorectal cancer. Such a method can comprise providing a compound of the sort discussed above or described elsewhere and contacting such a compound with a cellular medium comprising a cancer expressing a human ornithine aminotransferase with an amount of such a compound effective to reduce human ornithine aminotransferase activity. In certain embodiments, such a compound can be provided as part of a pharmaceutical composition. Regardless, such contact can be in vitro or in vivo.

More generally, the disclosed methods may be directed to inhibiting a human ornithine aminotransferase. Such a method can comprise providing a compound of the sort discussed above or described below, whether or not part of a pharmaceutical composition, and administering an effective amount of such a compound for contact with a human ornithine aminotransferase. Such contact can be, as would be understood in the art, for experimental and/or research purposes or as may be designed to simulate one or more in vivo or physiological conditions. Such compounds can include but are not limited to those illustrated by the following examples, referenced figures, incorporated references and/or accompanying synthetic schemes. In certain such embodiments, such a compound and/or combination thereof can be present in an amount at least partially sufficient to inhibit hOAT, cell proliferation and/or tumor growth.

The disclosed compounds preferably inhibit ornithine aminotransferase relative to other aminotransferases. In some embodiments, the disclosed compounds specifically inhibit ornithine aminotransferases (OATs) versus γ-aminobutyric acid aminotransferases (GABA-ATs). In some embodiments, a disclosed compound inhibits an OAT (e.g., hOAT) and has a $K_I$ which is at least 10, 20, 50, 100, 200, 500, or 1000× lower than the compound's $K_I$ for a GABA-AT.

BRIEF DESCRIPTION OF THE FIGURES

FIGS. 4A-4D. Localization of covalent modifications on hOAT. (FIG. 4A) Proposed structures and masses corresponding to hOAT adducts. HCD fragmentation maps for (FIG. 4B) unmodified hOAT (SEQ ID NO: 1), (FIG. 4C) hOAT-11b (SEQ ID NO: 1) and (FIG. 4A) hOAT-14 (SEQ ID NO: 1) with associated scoring metric[55] and modified residues colored for each adduct mass. Amino acid residues are numbered according to the full-length protein sequence (Uniprot P04181) used in crystallography studies and not to the recombinantly expressed version of hOAT. For clarity amino acid cleavage sites generating y199, y140 and y101 are shown in (FIG. 4B).

(FIG. 6A) MD simulation for 27 in the catalytic pocket of hOAT with intact salt bridge; (FIG. 6B) MD simulation for 27 in the catalytic pocket of hOAT with disrupted salt bridge; (FIG. 6C) MD simulation for 27' in the catalytic pocket of hOAT with disrupted salt bridge.

(FIG. 8A) Extracted ion chromatogram for 43 (+ESI, 170.04-170.08 m/z). (FIG. 8B) MS2 confirmation of metabolite 43

FIG. 9. Inhibitory activities of 14 against different aminotransferases. (A) hOAT. (B) GABA-AT. (C) Ala-AT and Asp-AT.

DETAILED DESCRIPTION

Figure 1:
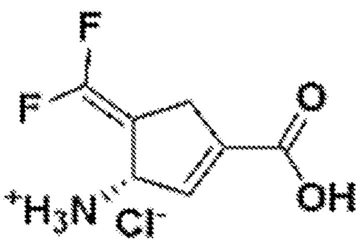
FIG. 1. Structures of analogs 9-15.
Figure 1:
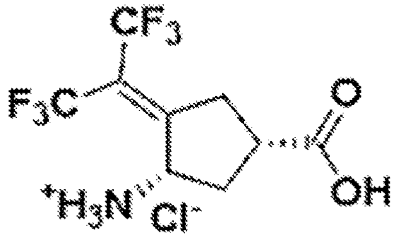
Figure 1:
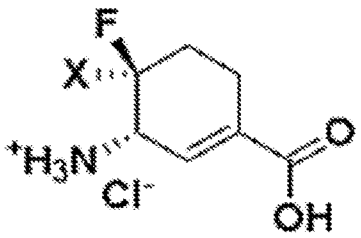
Figure 1:
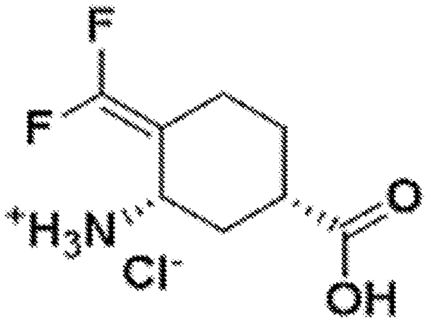
Figure 1:
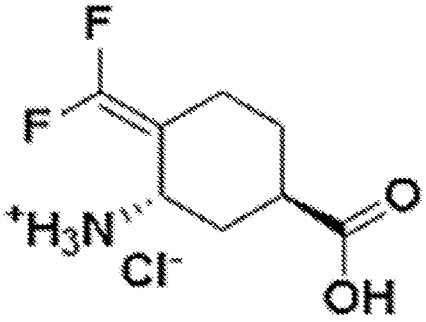
Figure 1:
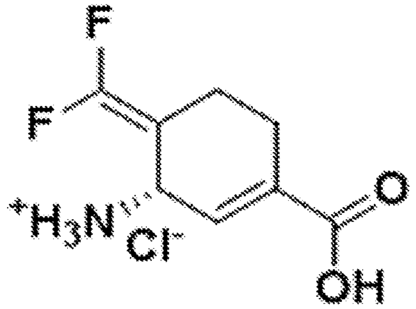
Figure 1:
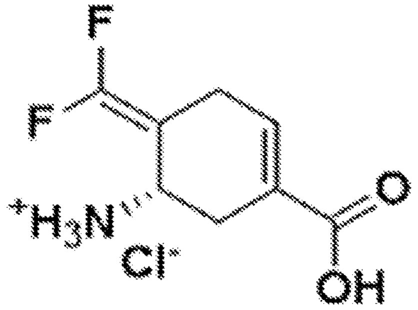

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the claimed subject matter and does not pose a limitation on the scope of the claimed subject matter.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, a "subject in need thereof" may include a human and/or non-human animal. A "subject in need thereof" may include a subject having a disease or disorder associated with ornithine aminotransferase (OAT) activity. A "subject in need thereof" may include a subject having a cell proliferative disease or disorder, which may include, but is not limited to hepatocellular carcinoma (HCC), lung cancer (non-small cell lung cancer (NSCLC)), and colorectal cancer.

Chemical Entities

New chemical entities and uses for chemical entities are disclosed herein. The chemical entities may be described using terminology known in the art and further discussed below.

As used herein, a dash "-" an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched $C_1$-C6 alkyl group). Exemplary alkylene groups include, but are not limited to $—CH_2—$, $—CH_2CH_2—$, $—CH_2CH_2CH_2—$, $—CH(CH_3)CH_2—$, $—CH_2CH(CH_3)CH_2—$, $—CH(CH_2CH_3)CH_2—$, and the like.

The term "halo" refers to a halogen substitution (e.g., —F, —Cl, —Br, or —I). The term "haloalkyl" refers to an alkyl group that is substituted with at least one halogen. For example, $—CH_2F$, $—CHF_2$, $—CF_3$, $—CH_2CF_3$, $—CF_2CF_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxyamido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic and/or heterocyclic aromatic group. Representative aryl groups include phenyl, naphthyl, anthracenyl, pyridinyl, quinolinyl, furanyl, thionyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxyamido, carboxylic acid, —C(O)alkyl, $—CO_2$alkyl, carbonyl, carboxyl, alkylthio, sulfonyl, sulfonamido, sulfonamide, ketone, aldehyde, ester, heterocyclyl, aryl or heteroaryl moieties, $—CF_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxy" or "carboxyl" as used herein refers to the radical —COOH or its corresponding salts, e.g. —COONa, etc. A carboxy alkyl ester refers to a compound having a moiety —C(O)O—R, where R is alkyl.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "amide" or "amido" or "amidyl" as used herein refers to a radical of the form $—R^1C(O)N(R^2)—$, $—R^1C(O)N(R^2)R^3—$, $—C(O)NR^2R^3$, or $—C(O)NH_2$, wherein $R^1$, $R^2$ and $R^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may be isomeric. In some embodiments, the disclosed compounds may be isomerically pure, wherein the compounds represent greater than about 99% of all compounds within an isomeric mixture of compounds. Also contemplated herein are compositions comprising, consisting essentially of, or consisting of an isomerically pure compound and/or compositions that are isomerically enriched, which compositions may comprise, consist essential of, or consist of at least about 50%, 60%, 70%, 80%, 90%, 95%, 96%, 97%, 98%, 99%, or 100% of a single isomer of a given compound.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the chiral or stereogenic carbon atom and or the optical rotation observed. The disclosed compounds encompass various stereo isomers and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound and/or compositions that are enantiomer enriched, which compositions may comprise, consist essential of, or consist of at least about 50%, 60%, 70%, 80%, 90%, 95%, 96%, 97%, 98%, 99%, or 100% of a single enantiomer of a given compound (e.g., at least about 95% of an R enantiomer of a given compound).

Various non-limiting embodiments of the disclosed compounds and methods of use can be considered with an understanding of a catalytic mechanism of hOAT and mechanism of inactivation of GABA-AT and hOAT. In a some embodiments, the disclosed subject matter relates to one or more hOAT inhibitors or inactivators, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable aqueous or nonaqueous solutions, dispersions, suspensions or emulsions, whether or not sterile. The resulting compositions can be, in conjunction with the various methods described herein, for administration or contact with a human ornithine aminotransferase. Whether or not in conjunction with a pharmaceutical composition, "contacting" means that a human ornithine aminotransferase and one or more inhibitor or inactivator compounds are brought together for purpose of binding and/or complexing such an inhibitor or inactivator compound to the enzyme. Amounts of a compound effective to inhibit or inactivate a human ornithine aminotransferase may be determined empirically, and making such determinations is within the skill in the art. Inhibition or otherwise affecting a human ornithine aminotransferase activity includes reduction, mitigation and/or modulation, as well as elimination of hOAT activity (i.e., inactivation), glutamate production, glutamine synthesis, cell proliferation and/or tumor growth.

It is understood by those skilled in the art that dosage amount will vary with the activity of a particular inhibitor or inactivator compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing an inhibitor or inactivator compound into association with a carrier and, optionally, one or more additional adjuvants or ingredients. For example, standard pharmaceutical formulation techniques can be employed, such as those described in Remington's Pharmaceutical Sciences, Mack Publishing Company, Easton, PA.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the disclosed compounds may be utilized as inhibitor or inactivator compounds for the manufacture of a medicament for therapeutic use in the treatment or prevention of a disease or disorder associated with hOAT activity, expression, or overexpression. Suitable diseases or disorders may include cell proliferative diseases or disorders, which may include but are not limited to hepatocellular carcinoma (HCC), non-small cell lung cancer (NSCLC), and colorectal cancer.

Generally, with respect to various embodiments, the disclosed subject matter can be directed to method(s) for the treatment of a pathologic proliferative disorder. As used herein, the term "disorder" refers to a condition in which there is a disturbance of normal functioning. A "disease" is any abnormal condition of the body or mind that causes discomfort, dysfunction, or distress to the person affected or those in contact with the person. Sometimes the term is used broadly to include injuries, disabilities, syndromes, symptoms, deviant behaviors, and atypical variations of structure and function, while in other contexts these may be considered distinguishable categories. It should be noted that the terms "disease", "disorder", "condition" and "illness", are equally used herein.

According to certain embodiments, the disclosed methods can be specifically applicable for the treatment of malignant proliferative disorders, including malignant proliferative disorders that express human ornithine aminotransferase (hOAT). As used herein, "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. Accordingly, the compounds, compositions, and methods disclosed herein may be used in the treatment of non-solid and solid tumors.

Malignancy, as contemplated herein, may be selected from the group consisting of melanomas, carcinomas, leukemias, lymphomas and sarcomas, which express hOAT. Malignancies that can be treated by the methods disclosed herein, including malignancies that express hOAT can comprise but are not limited to hematological malignancies (including leukemia, lymphoma and myeloproliferative disorders), hypoplastic and aplastic anemia (both virally induced and idiopathic), myelodysplastic syndromes, all types of paraneoplastic syndromes (both immune mediated and idiopathic) and solid tumors (including bladder, rectum, stomach, cervix, ovarian, renal, lung, liver, breast, colon, prostate, GI tract, pancreas and Karposi). More particularly, according to certain embodiments, the compounds and compositions used in conjunction can be used in methods for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma, retinoblastoma, carcinoma of the lacrimal gland, sarcoma of the orbit, brain, spinal cord, vascular system, hemangiosarcoma and Kaposi's sarcoma.

The compounds and compositions disclosed herein may be administered in methods of treatment as known in the art. Accordingly, various such compounds and compositions can be administered in conjunction with such a method in any suitable way. For example, administration may comprise oral, intravenous, intraarterial, intramuscular, subcutaneous, intraperitoneal, parenteral, transdermal, intravaginal, intranasal, mucosal, sublingual, topical, rectal or subcutaneous administration, or any combination thereof.

According to some embodiments, the treated subject may be a mammalian subject. Although the methods disclosed herein are particularly intended for the treatment of proliferative disorders in humans, other mammals are included. By way of non-limiting examples, mammalian subjects include monkeys, equines, cattle, canines, felines, mice, rats and pigs.

The terms "treat, treating, treatment" as used herein and in the claims mean ameliorating one or more clinical indicia of disease activity in a subject having a pathologic disorder. "Treatment" refers to therapeutic treatment. Those in need of treatment are mammalian subjects suffering from any pathologic disorder. By "patient" or "subject in need" is meant any mammal for which administration of a compound or any pharmaceutical composition of the sort described herein is desired, in order to prevent, overcome, modulate or slow down such infliction. To provide a "preventive treatment" or "prophylactic treatment" is acting in a protective manner, to defend against or prevent something, especially a condition or disease.

More generally, the disclosed methods may be directed to affecting, modulate, reducing, inhibiting and/or preventing the initiation, progression and/or metastasis (e.g., from the liver elsewhere or to the liver from any other organ or tissue) of a malignant pathologic proliferative disorder associated with hOAT activity. (See, e.g., Lucero O M, Dawson D W, Moon R T, et al. A re-evaluation of the "oncogenic" nature of Wnt/beta-catenin signaling in melanoma and other cancers. *Curr Oncol Rep* 2010, 12, 314-318; Liu Wei; Le Anne; Hancock Chad; Lane Andrew N; Dang Chi V; Fan Teresa W-M; Phang James M. Reprogramming of proline and glutamine metabolism contributes to the proliferative and metabolic responses regulated by oncogenic transcription factor c-MYC. *Proc. Natl. Acad. Sci. USA* 2012, 109(23), 8983-8988; and Tong, Xuemei; Zhao, Fangping; Thompson, Craig B. The molecular determinants of de novo nucleotide biosynthesis in cancer cells. *Curr. Opin. Genet. Devel.* 2009, 19(1), 32-37.)

EXAMPLES

The following Examples are illustrative and should not be interpreted to limit the scope of the claimed subject matter. The following non-limiting Examples and data illustrate various aspects and features relating to the disclosed compounds, compositions, and methods including the treatment of diseases and disorders associated with hOAT activity, expression, or overexpression, and/or reduction of human ornithine aminotransferase activity, such as cell proliferative diseases and disorders including, but not limited to hepatocellular carcinoma (HCC), non-small cell lung cancer (NSCLC), and colorectal cancer. While the utility of this invention is illustrated through the use of several compounds and compositions which can be used therewith, it will be understood by those skilled in the art that comparable results are obtainable with various other compound(s), as are commensurate with the scope of this invention.

Example 1—Unexpected Mechanism of (S)-3-Amino-4-(Difluoromethylene)-cyclohex-1-Ene-1-Carboxylic Acid as a Selective Inactivator of Human Ornithine Aminotransferase Human ornithine aminotransferase (hOAT) is a pyridoxal 5'-phosphate (PLP)-dependent enzyme, which was recently found to play an important role in the metabolic reprogramming of hepatocellular carcinoma (HCC) via proline and glutamine metabolic pathways. The selective inhibition of hOAT by compound 10 exhibited potent in vivo anti-tumor activity, along with dramatically reduced alpha-fetoprotein (AFP, a biomarker for HCC) levels. We rationally designed, synthesized, and evaluated a series of six-membered ring analogs. Among them, analog 14 was identified as a novel selective hOAT inhibitor and demonstrated 18.6 times more potent than 10. Three types of protein mass spectrometry and crystallography of hOAT-14 revealed the formation of the final adduct (28') in the catalytic pocket, which surprisingly establishes two covalent bonds with nearby residues. Later, molecular dynamics (MD) simulations and soaking crystallography studies were carried out to disclose the potential binding pose of active intermediate 27', leading to the initial reaction of the warhead with *Thr322 and the following nucleophilic attack of catalytic Lys292. Besides, the turnover mechanism of 14 by hOAT was also revealed via the mass spectrometry-based analysis of metabolites and fluoride ion release experiments.

Introduction

Hepatocellular carcinoma (HCC) is the most common liver cancer subtype and the second leading cause of cancer death worldwide.[1-4] The disease is highly malignant, radiotherapy-resistant, and refractory to the standard-of-care chemotherapy, sorafenib.[5-8] Recently, human ornithine aminotransferase (hOAT) was identified as a metabolic regulator of HCC progression via proline and glutamine metabolic pathways.[9-10] OAT (E.C. 2.6.1.13) is a pyridoxal 5'-phosphate (PLP)-dependent enzyme,[11] which is found in the mitochondrial matrix of most human and animal tissues.[12] Mechanically, two coupled half-reactions are required to complete one transamination cycle of OAT (Scheme 1).[13] In the first half-reaction, ornithine binds with cofactor PLP in the catalytic pocket of OAT to form Schiff base M1, followed by the tautomerization to intermediate M2; the subsequent hydrolysis of M2 generates pyridoxamine 5'-phosphate (PMP) and glutamate γ-semialdehyde (GyS) that spontaneously cyclizes to Δ1-pyrroline-5-carboxylate (PSC). In the second-half reaction, OAT catalyzes the conversion of α-ketoglutarate (α-KG) and PMP to L-glutamate (L-Glu) and PLP. Glutamate and glutamine metabolism have acknowledged roles in supporting the anabolic demands of tumor growth and it is increasingly clear that proline metabolism promotes liver cancer tumorigenesis.[14-17] Not only L-Glu and proline have direct effects on metabolic rewiring, but they also induce a hypoxia-inducible factor-1α (HIF1α) transcriptional program in HCC leading to sorafenib resistance and retained proliferative capacity under oxygen starvation.[18] hOAT is commonly overexpressed in HCC due to dysregulation and activation of the Wnt/β-catenin pathway.[19-20] The selective inhibition of hOAT exhibited potent in vivo anti-tumor activity in the HCC mouse model, along with dramatically reduced alpha-fetoprotein (AFP, a biomarker for HCC) levels.[10] Recently, upregulation of hOAT was found in non-small cell lung cancer (NSCLC) cells, which contributes to the promotion of proliferation, invasion, and migration, the inhibition of apoptosis, and the change of cell cycle.[21] The specific knockdown of hOAT in NSCLC inhibited the cell proliferation in vitro and suppressed the tumor growth in vivo.[21] Thus, hOAT can serve as a promising therapeutic target for the treatment of HCC and related cancers with similar underlying metabolic alterations.

Scheme 1. Catalytic Mechanism of OAT

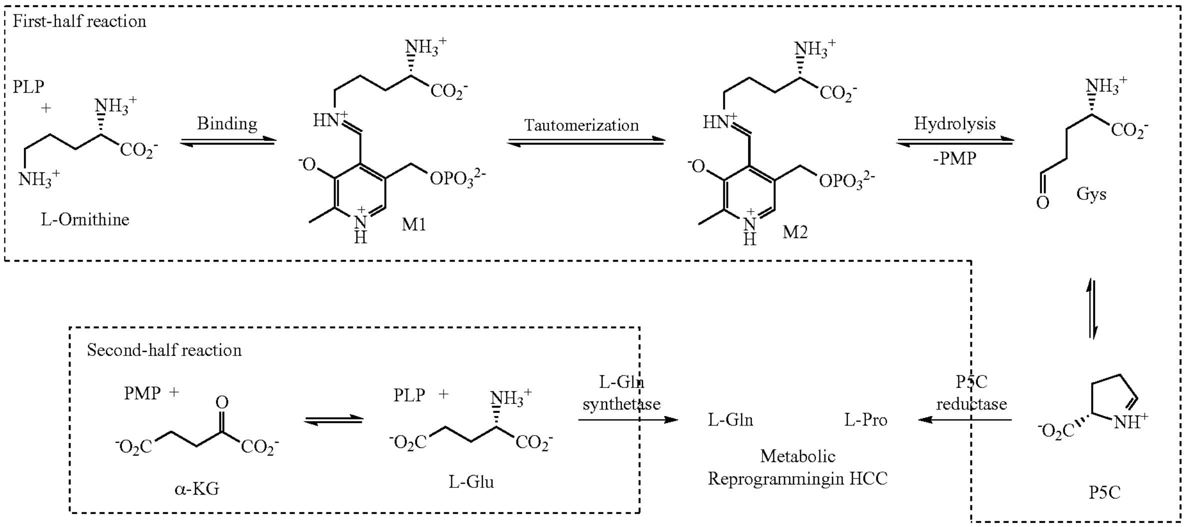

OAT belongs to the same enzyme subgroup[22] as γ-aminobutyric acid aminotransferase (GABA-AT, E.C. 2.6.1.19) that demonstrates a similar catalytic mechanism as OAT,[23] in which GABA is converted to succinic semialdehyde (SSA) in the first-half reaction.[24] In past decades, our laboratory has been devoting efforts to the rational design of mechanism-based inactivators (MBIs) of GABA-AT[25] for the potential treatment of epilepsies and addictions. MBIs usually act as native substrates initially and inhibit the target enzymes after the conversion to active intermediates in their catalytic sites,[25-28] which can demonstrate higher potency and reduced off-target effects when compared with traditional inhibitors.[10, 25, 29-30] For example, vigabatrin (1)[31], as an MBI of GABA-AT, is an FDA-approved drug for the treatment of infantile spasms and refractory complex partial seizures (Scheme 2).[32] Mechanism study[33] revealed that 1 initially forms Schiff base with PLP in the catalytic pocket of GABA-AT, followed by the tautomerization as the native substrates do, to afford intermediate 3. Catalytic residue Lys329 attacks at the Michael acceptor of 3 to form covalent adduct 4, which accounts for 70% of the inactivation pathway of 1 (Scheme 2).[33] Based on this mechanism, difluoro-substituted conformationally-rigid analog 5 was synthesized and exhibited 186 times more efficient as an inactivator than 1, determined by their $k_{inact}/K_I$ values (Scheme 2).[34-35] Analogue 5 was also found to generate Michael acceptor intermediate 7 via similar steps as shown in the mechanism pathway of 1.[36] Interestingly, highly electrophilic 7 reacts with water molecules existing in the pocket, instead of Lys329, leading to the formation of tight-binding adduct 8, in which the newly generated carboxylate forms the electrostatic interaction with Arg445 (Scheme 2).[36] Currently, 5 is investigated in clinical trial for the potential treatment of infantile spasms and cocaine dependency.[37-38] Later, cyclopentene analog 9 (FIG. 1) was afforded with improved potency for GABA-AT ($k_{inact}/K_I$=342 $mM^{-1}$ $min^{-1}$) and demonstrated a similar mechanism as 5, in which the nucleophilic attack of water molecules was potentially assisted by the catalytic lysine.[29] Because of the high similarity of catalytic pockets between these two aminotransferases, 9 also exhibited inhibitory activities against hOAT with relatively lower efficiency ($k_{inact}/K_I$=7.6 $mM^{-1}$ $min^{-1}$).[29]

proven to improve the potency and selectivity of hOAT inactivators, leading to the discovery of cyclohexene analogs 11a and 11b (FIG. 1).[40]

We aim to discover potent and selective hOAT inactivators for the treatment of HCC and reveal the underlying mechanism of inactivators for further improved rational design. Herein, we designed and synthesized six-membered ring analogs 12-15 based on GABA-AT inactivators 5 and 9 (FIG. 1). Among them, analog 14 is 18.6 times more efficient as an inactivator of hOAT than 10, along with excellent selectivity over other aminotransferases. We also revealed the inactivation mechanism for 14 through crystallography and mass spectrometry, with the identification of an unexpected covalent adduct surprisingly attached to two residues from two different chains in the hOAT pocket, while the turnover mechanism study detected the generation of an unusual aromatic metabolite.

Results and Discussion

Syntheses of Analogues 12-15

The synthetic route of 12-15 is shown in Scheme 3. Chirally-pure lactam 16[41] was prepared via a reported procedure. Intermediate 16 was treated with silver trifluoroacetate, followed by Dess-Martin oxidation, to afford ketones 17a and 17b. Intermediate 18 was obtained from 17b with the protection of PMB, followed by the treatment[34-35] of Scheme 2. Inactivation mechanism of GABA-AT by Vigabatrin (1) and CPP115 (5).

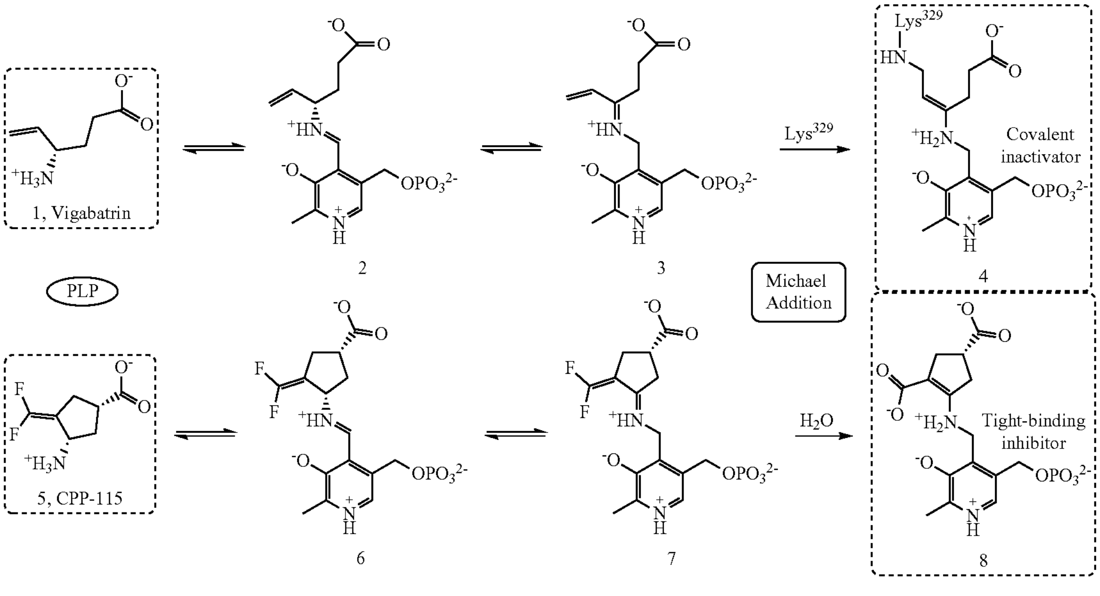

When comparing the catalytic pockets of hOAT and GABA-AT for differences, hOAT has a more flexible and larger catalytic pocket, resulting from the replacement of Phe351 and Ile72 in GABA-AT with Tyr55 and Tyr85 in hOAT, which can accommodate ornithine that is one carbon longer than GABA.[39] In 2015, relative bulky trifluoromethyl analog 10 (FIG. 1) was found to show improved selectivity for hOAT over GABA-AT.[10] Notably, administration of 10 at low doses (0.1 and 1.0 mg/kg) has been shown to effectively reduce AFP levels and suppress HCC tumor growth in vivo.[10] Very recently, the enlarge-ring strategy has been $CHF_2PO(OEt)_2$ and $^tBuLi$, to provide intermediate 19. Deprotection of PMB with CAN and the ring-opening reaction under acid conditions afforded the desired product 12. Chirally-pure ester 21 was prepared as reported,[40] which was treated[42] with 2-$PySO_2CF_2H$ and $^tBuOK$ in DMF to give difluoromethylene intermediate 22. Interestingly, the treatment of 22 with PhSeCl and KHMDS afforded bicyclic lactam 23 as the major product. The sequential Boc protection, ring-opening reaction, and oxidative elimination provided two isomers 24a and 24b. The desired products 13-15 were afforded from the corresponding esters under acid conditions, respectively.

Scheme 3. Syntheses of six-membered ring analogs 12-15
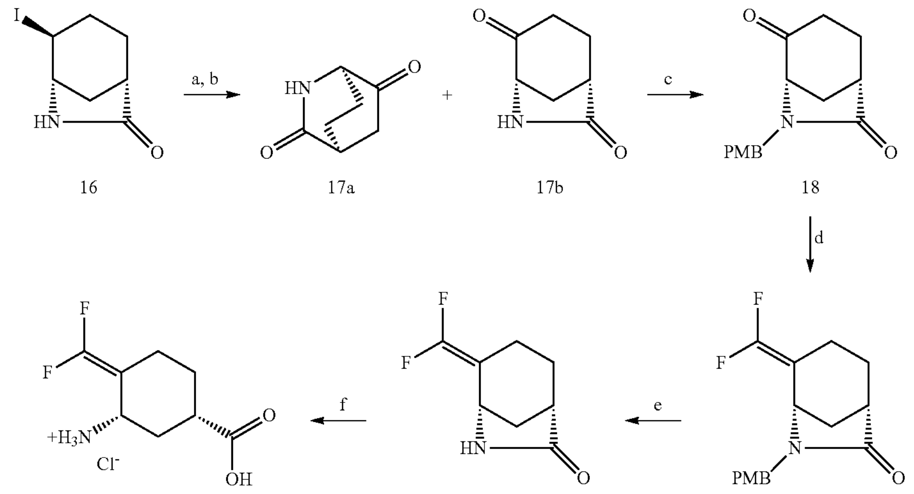
16 17a 17b 18
12 20 19
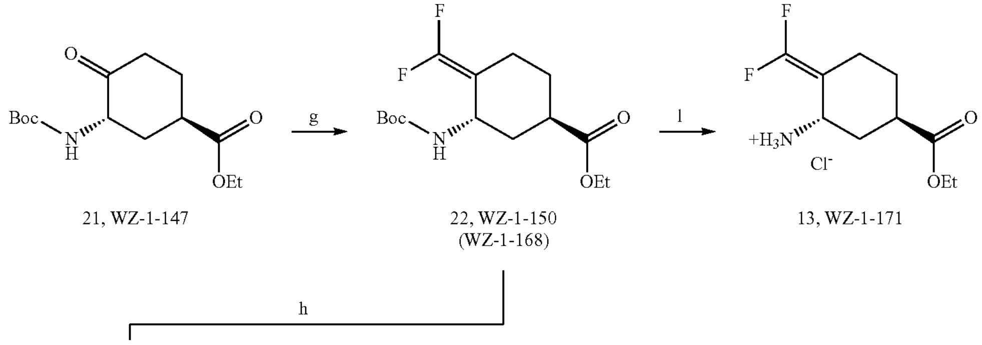
21, WZ-1-147
22, WZ-1-150
(WZ-1-168)
13, WZ-1-171

-continued

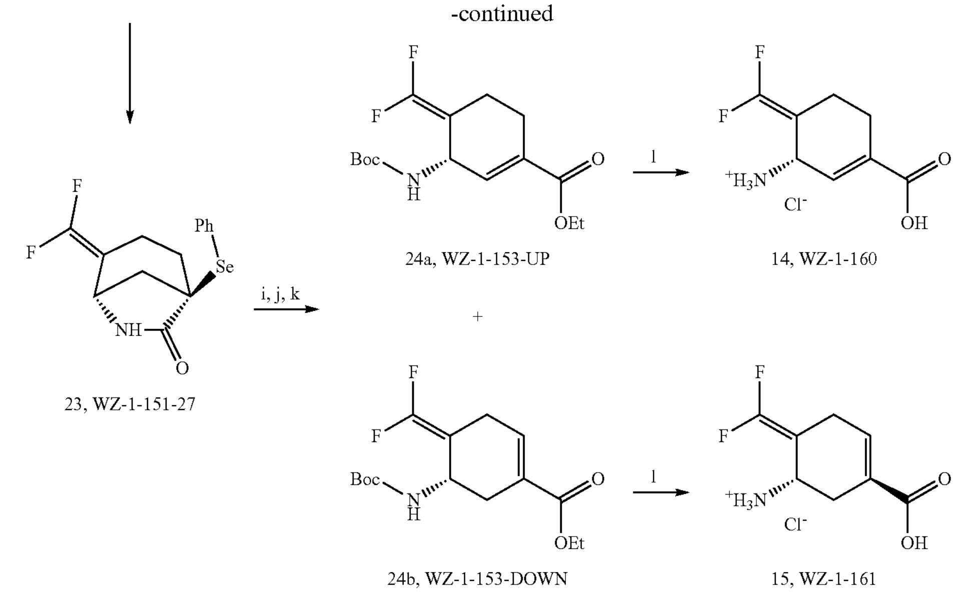

23, WZ-1-151-27

24a, WZ-1-153-UP

14, WZ-1-160

24b, WZ-1-153-DOWN

15, WZ-1-161

Reagents and conditions:
(a) $AgOC(O)CF_3$, $CH_3NO_2$, 0° C.-r.t., 16 h; then $NH_3$/MeOH, 1 h;
(b) DMP, $CH_3CN$, $NaHCO_3$ (b) NaH, DMF; PMBCl, 0° C.,-r.t., 16 h;
(c) $CHF_2PO(OEt)_2$, $^{t}$BuLi (1.7M in pentane), -100° C.,-r.t., 2 h; then reflux, 16 h;
(d) CAN, $CH_3CN$, $H_2O$, 0° C.-r.t., 10 h;
(e) HCl (aq. 4M), 75° C., 5 h.
(e) 2-$PySO_2CF_2H$, $^{t}$BuOK, DMF -60° C., then -40° C., $NH_4Cl$ (saturated aq.), HCl (3M);
(f) PhSeCl, KHMDS (1M in THF), -78° C.;
(g) $Boc_2O$, DIPEA, DMAP, DCM, r.t., overnight;
(h) $K_2CO_3$, EtOH, 0° C.-r.t. 4 h;
(i) m-CPBA, DCM, r.t., 2 h;
(j) HCl (aq. 4M), AcOH, 80° C., overnight.

Kinetic Studies Analogues 12-15

As shown in Table 1, six-membered ring analogs 12-15 exhibited a lower binding affinity to GABA-AT with much greater $K_I$ values than 5 or 9, which is well consistent with our initial design strategy. The enlarged ring could potentially obstruct the initial binding with GABA-AT,[40] which has a relatively small and rigid catalytic pocket.[39] Although cyclohexane analogs 12 and 13 showed enhanced selectivity for OAT, their potency was greatly decreased. The introduction of the double bond significantly increased their binding affinity with OAT, which may result from the reduced steric hindrance of cyclohexene.[40] α, β-unsaturated analog 14 is more potent than the other cyclohexene analog 15, possibly due to the reduced acidity of the γ-position, which is critical for the tautomerization step and further inactivation.[25]

Figure 9:
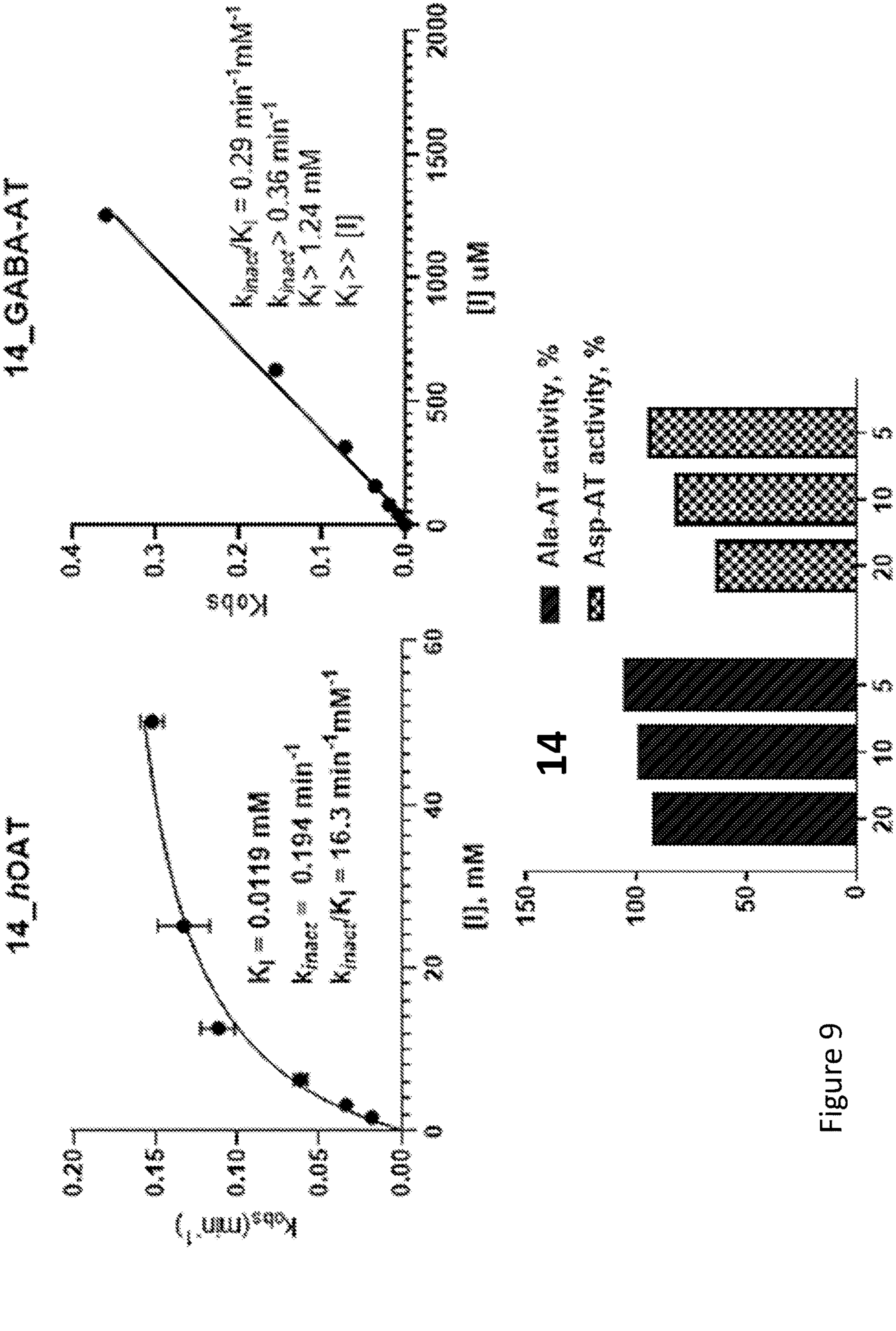

As the most potent analog, 14 is 18.6-fold more efficient as an inactivator of OAT than 7 ($k_{inact}/K_I$=0.87 $min^{-1}$ $mM^{-1}$) that significantly suppressed HCC tumor growth in vivo,[10] along with good selectivity over GABA-AT with lower efficiency constants ($k_{inact}/K_I$=0.29 $min^{-1}$ $mM^{-1}$). Besides, it demonstrated little or no inhibitory activities against alanine aminotransferase (Ala-AT) and aspartate aminotransferase (Asp-AT) at high concentrates (up to 20 mM, FIG. 9).

TABLE 1

Kinetic constants for the inactivation of hOAT and GABA-AT by 1, 9 and 12-15[a]

| | hOAT | | | GABA-AT | | |
|---|---|---|---|---|---|---|
| Comp. | $K_I$ (mM) | $k_{inact}$ ($min^{-1}$) | $k_{inact}/K_I$ ($mM^{-1}min^{-1}$) | $K_I$ (mM) | $k_{inact}$ ($min^{-1}$) | $k_{inact}/K_I$ ($mM^{-1}min^{-1}$) |
| 12 | 1.27 ± 0.20 | 0.116 ± 0.007 | 0.091 | 1.31 ± 0.40 | 0.025 ± 0.002 | 0.019 |
| 13 | 1.48 ± 0.21 | 0.090 ± 0.005 | 0.064 | >13.1 | >0.19 | 0.015 ± 0.001[b] |
| 14 | 0.012 ± 0.002 | 0.194 ± 0.015 | 16.2 | >1.24 | >0.36 | 0.29 ± 0.01[b] |
| 15 | 0.098 ± 0.014 | 0.054 ± 0.002 | 0.55 | >2.49 | >0.22 | 0.087 ± 0.003[b] |
| 9[40] | 0.065 ± 0.010 | 0.057 ± 0.003 | 0.87 | — | — | — |
| 1[40] | — | — | — | 0.29 ± 0.09 | 0.21 ± 0.03 | 0.72 |

[a]$k_{inact}$ and $K_I$ values were determined by the equation: $k_{obs}$ = $k_{inact}$*[I]/($K_I$ + [I]) and are presented as means and standard errors.
[b]ratio of $k_{inact}/K_I$ was determined by the slope of $k_{obs}$ = $k_{inact}$*[I]/($K_I$ + [I]).
$k_{inact}$ is greater than the maximum $k_{obs}$ determined in the time-dependent assay; $K_I$ is greater than $k_{obs}$(max)/ratio.

Cocrystal Structure for hOAT Inactivated by 9

Cyclopentene analog 9 was found to inactivate GABA-AT in a similar manner as cyclopentane analog 5 (Scheme 2), where a tight-binding adduct was formed via the nucleophilic attack of water molecules at Michael acceptor position.[29] Not surprisingly, 9 could also inactivate hOAT due to the high similarity of catalytic pockets between these two aminotransferases, but its inactivation mechanism with hOAT has not to be disclosed yet. Thus, we obtained the cocrystal structure of hOAT inactivated by 9, which provided us some clues for the inactivation study of its cyclohexene analog (14).

Cocrystal Structure for hOAT Inactivated by 9.

Figure 2:
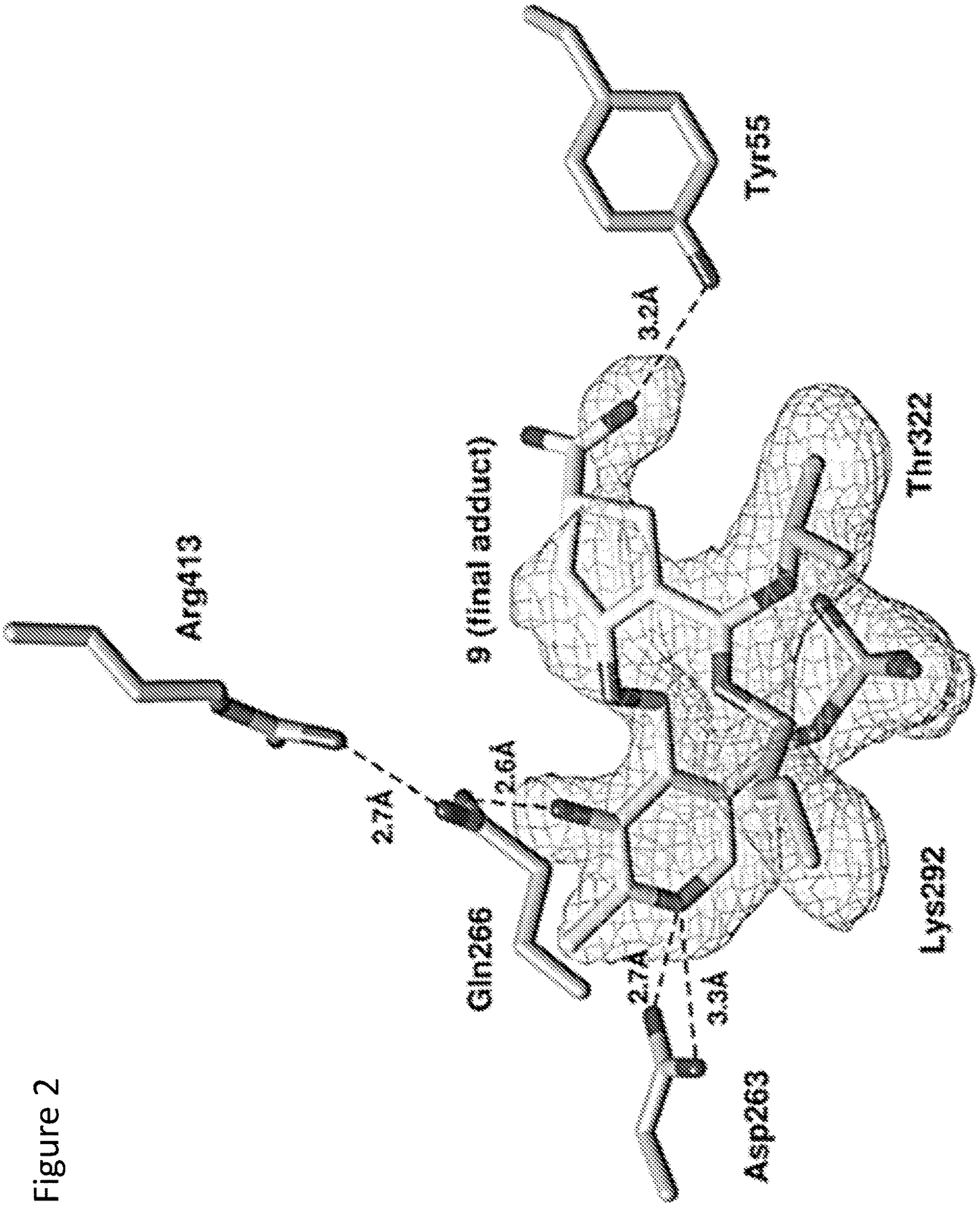
FIG. 2. $2F_o$-$F_c$ map (at 1.0σ) of hOAT-9 cocrystal structure (PDB: 7LNM). Dashed lines indicated hydrogen-bonds.
Figure 10:
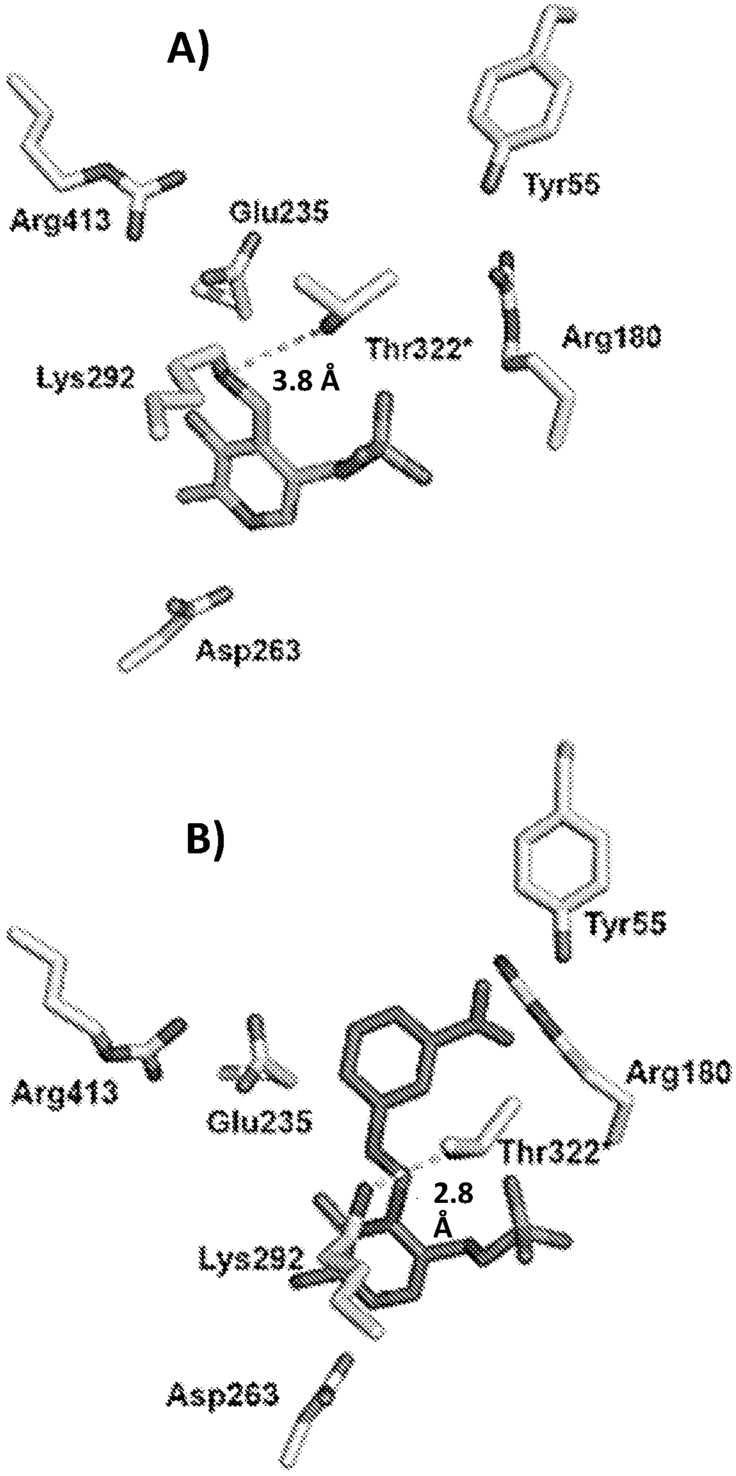
FIG. 10. Crystal structure of hOAT. (A) Native hOAT (PDB: 1OAT). (B) hOAT-gabaculine (PDB: 1GBN). (C) hOAT-canaline (PDB: 2CAN). (D) hOAT-10 (PDB: 6OIA).
Figure 10:
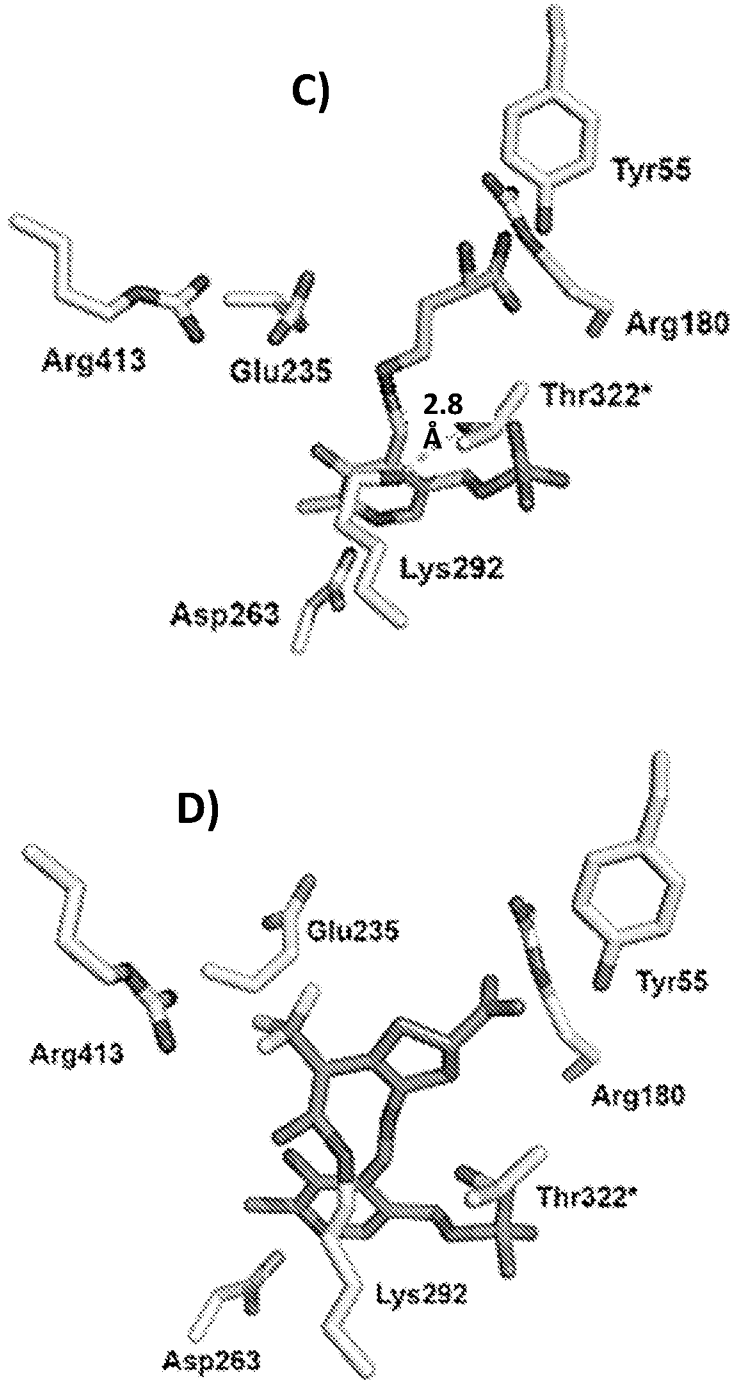

The structure of hOAT inactivated by 9 was solved by molecular replacement using a monomer from a previously reported structure of hOAT[43] (PDB code 1OAT), while water molecules and ligand atoms were deleted. As shown in FIG. 2, the adduct surprisingly forms two covalent bonds with nearby residues Lys292 and *Thr322, thus preventing the protein from normal functioning. Previously, several hOAT inactivators[40, 44-46] were found to form a covalent bond with the Lys292, but no inactivators so far were found to covalently interact with *Thr322 or other noncatalytic residues. Catalytic Lys292 plays an important role in the protein native reaction, which is covalently bonded to PLP and located close to (3.8 Å) *Thr322 as shown in the holoenzyme structure of hOAT (FIG. 10A). Interestingly, cocrystals[47] with gabaculine (PDB: 1GBN, FIG. 10B) and L-canaline (PDB: 2CAN, FIG. 10C) revealed a potential H-interaction between the free Lys292 and *Thr322 of the different protein subunit, indicating *Thr322 could be "activated" during the native reaction or inactivation process.

Although the formation of these two covalent bonds is quite clear as shown in this crystal structure, the electron density for the carboxylate group part is relatively weak and is completely missing in two out of six copies of the ligand in an asymmetric unit. This observation may result from the weak hydrogen bond interaction between the carboxylate group and nearby Tyr55. Aminotransferases inactivators usually are converted to active intermediates after binding with the cofactor PLP in the catalytic pocket, leading to the formation of various kinds of final adducts.[25] Thus, it would be difficult to determine the final adduct of MBI merely based on X-ray cocrystal, compared with the cases for traditional covalent inhibitors. However, this preliminary result provided us some new ideas for mechanism study, in which Lys292 or/and *Thr322 could be involved in the inactivation of hOAT by 14.

Inactivation Mechanism

MBIs of aminotransferases are reported to inactivate the enzymes through different mechanism pathways, along with the formation of covalent or tight-binding adducts occupying the catalytic pockets.[25] Based on previous reports (Scheme 2) and preliminary cocrystal results for hOAT-9 (FIG. 2), two possible mechanistic pathways (a and b) for the hOAT inactivation by 14 were proposed (Scheme 4). Initially, Schiff base 25 was formed from 14 and PLP similar to the native substrate (Scheme 1), followed by the deprotonation at the γ-position (26). Mechanistic pathway a is similar to the mechanism of 1 and 5 (Scheme 2), in which Michael acceptor intermediate 27 is generated with the protonation at the PLP-C4' position. The following nucleophilic attack of water molecules, Lys292 and/or *Thr322 could lead to the formation of double-covalent adduct 28 (a1, Lys Thr-addition), covalent adduct 30 (a2, Lys $H_2O$)-addition), covalent adduct 30 (a2, Thr $H_2O$)-addition) or tight-binding adduct 32 (a4, $H_2O$)-addition), respectively. Mechanistic pathway b was proposed base on the inactivation mechanism of hOAT by gabaculine (Scheme 7),[47-48] a naturally occurring neurotoxin.[49] Intermediate 33 can be formed with the protonation at the defluoromethylene position of intermediate 26, followed by several steps of tautomerization to afford tight-binding aromatic adduct 35 (b, aromatization). To further identify the mechanism for the inactivation of hOAT by 14, we carried out dialysis experiments and obtained three types of protein mass spectra and the cocrystal structure, which were further supported by the computational calculations and the soaking crystal structure.

Scheme 4. Possible inactivation mechanisms for 14.
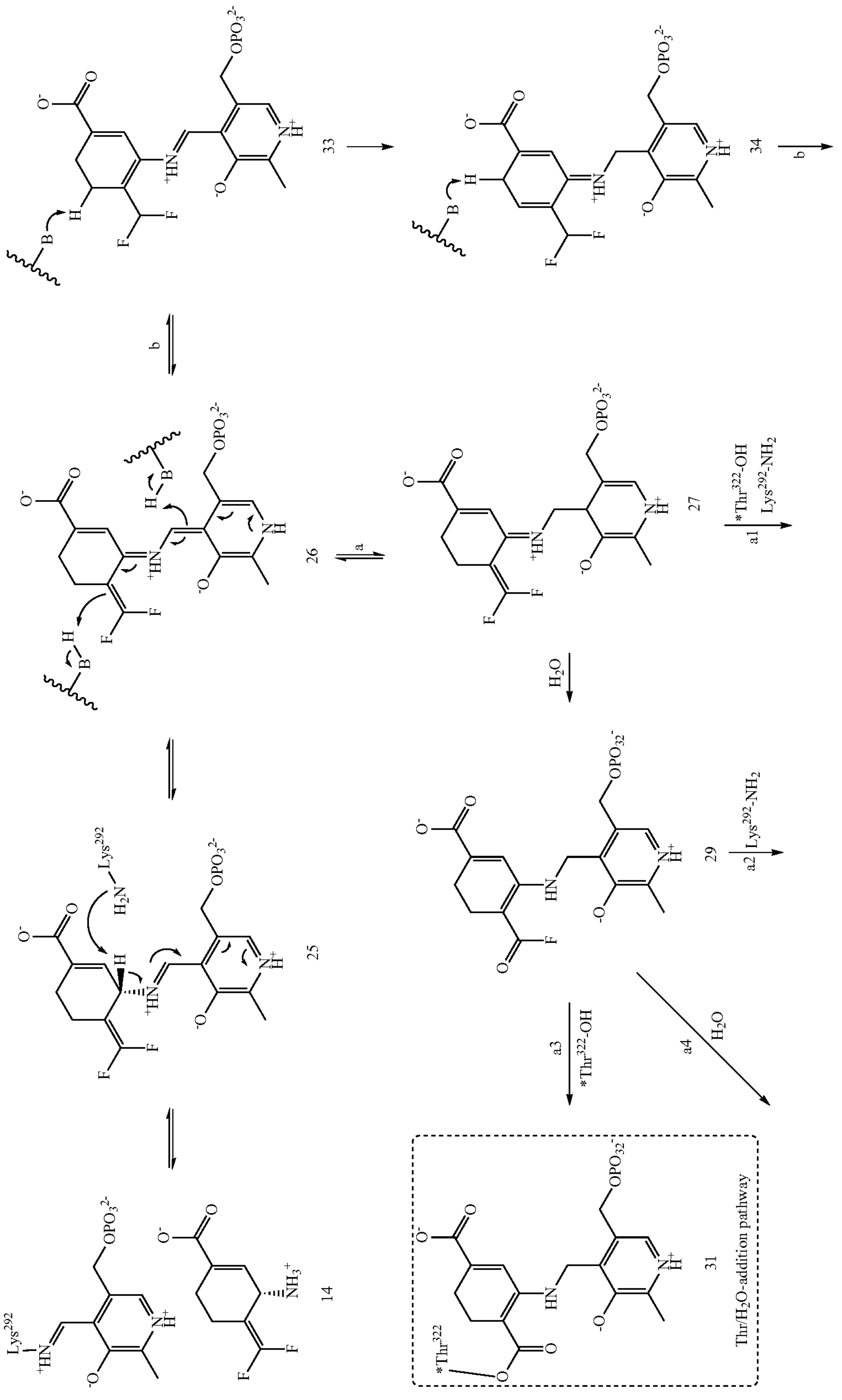

-continued
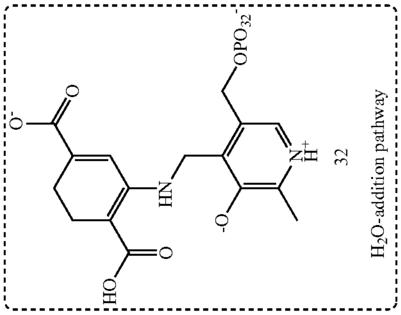
32
H$_2$O-addition pathway
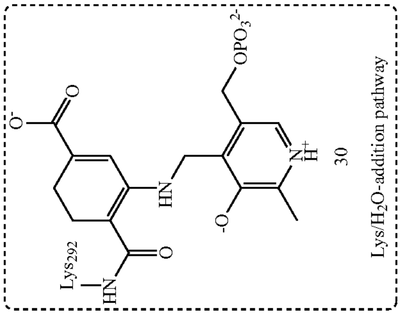
30
Lys/H$_2$O-addition pathway
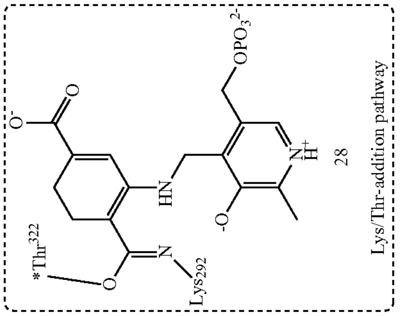
28
Lys/Thr-addition pathway
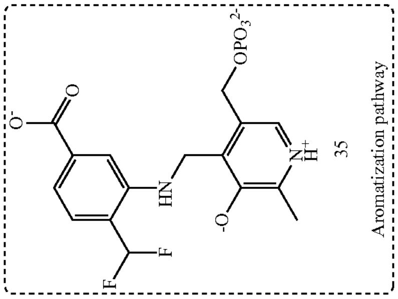
35
Aromatization pathway Dialysis.

Figure 11:
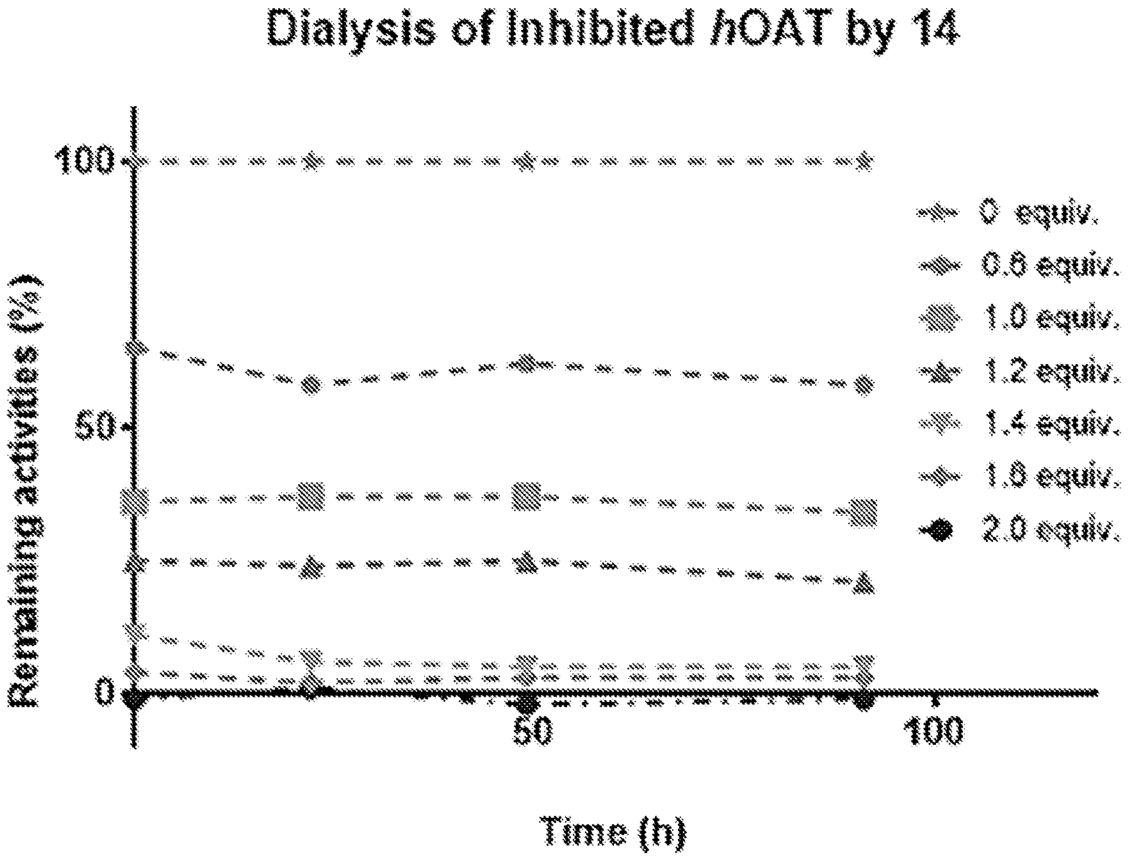
FIG. 11. Time-dependent dialysis of partially or fully inhibited hOAT by varying concentrations of 14 (top) and 9 (bottom).
Figure 11:
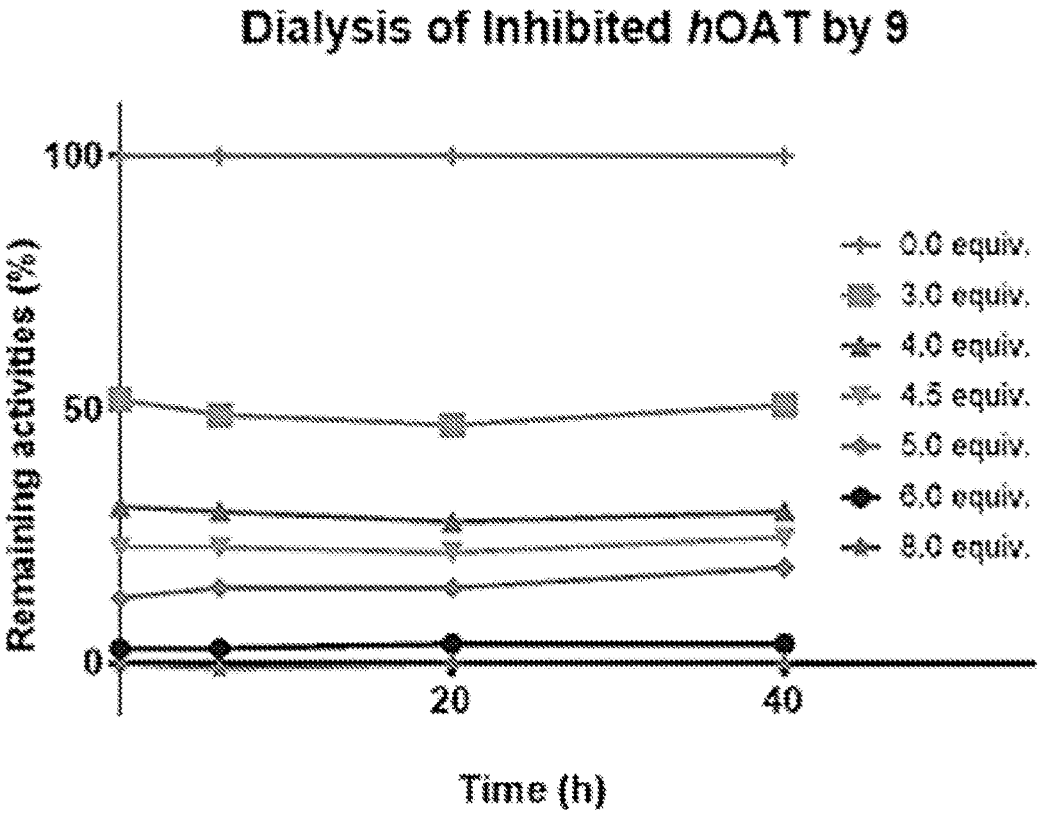

Previously, five-membered ring analogs 5 and 9 were identified as partially irreversible inhibitors of GABA-AT, with the formation of the tight-binding adducts.[29-30] Thus, time-dependent reactivation experiments of hOAT for cyclohexene analog 14 were carried out to determine if similar reversible components were also involved during the inactivation. After hOAT activity was partially or fully abolished by 0.6-2.0 equivalents of 14, aliquots at different time intervals were collected and assayed for the return of enzyme activity. No matter how many equivalents of 14 were used, no enzyme activity recovered, even after 91 h of dialysis (FIG. 11), suggesting its fully irreversible inhibitory activities against hOAT. Similarly, 5 was also demonstrated to be a fully irreversible inhibitor of hOAT in the dialysis experiment (FIG. 11), which was consistent with the observation in its cocrystal structure (FIG. 2).

Intact Protein Mass Spectrometry.

Figure 12:
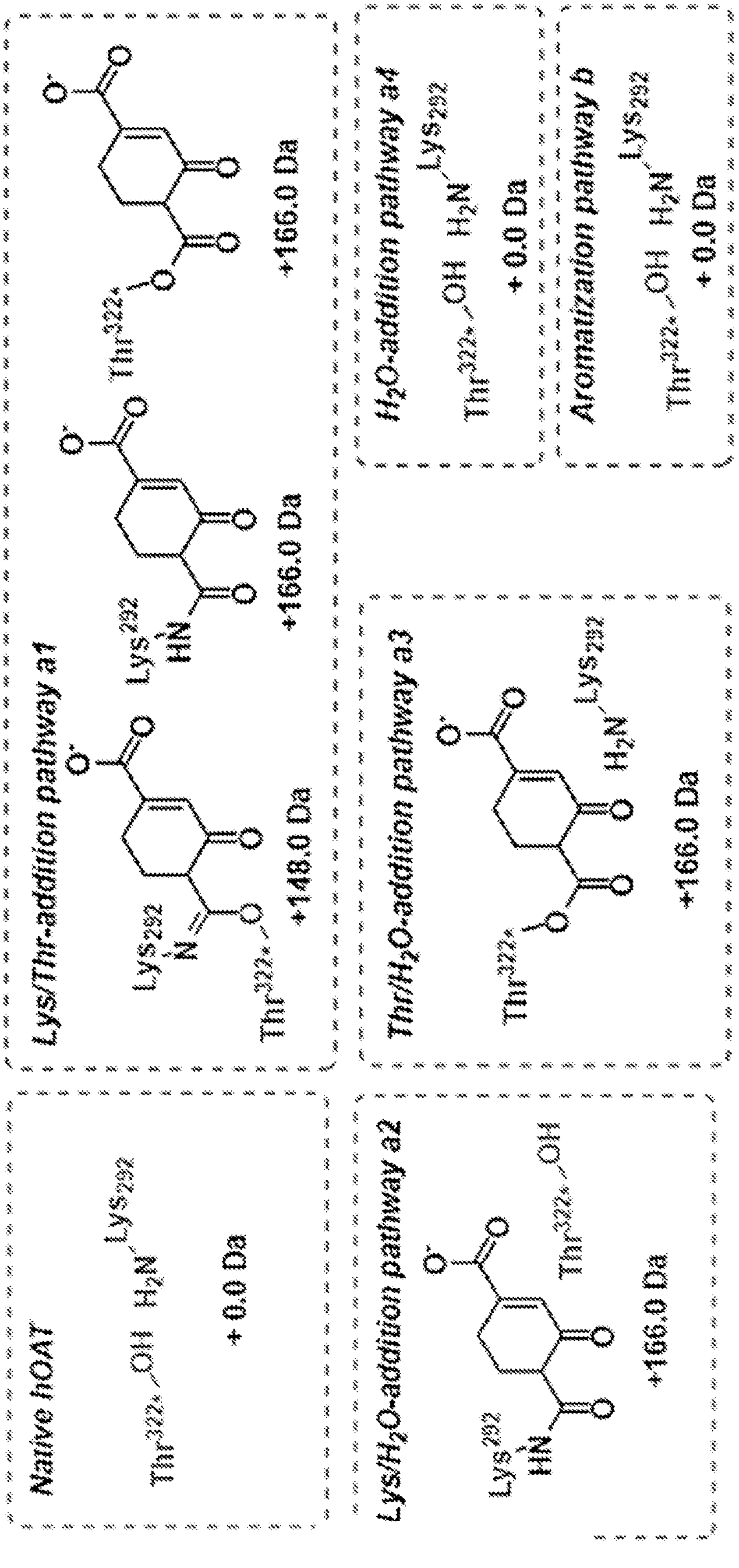
FIG. 12. Structures of possible adducts for hOAT-14 detected by intact protein mass spectrometry.
Figure 13A:
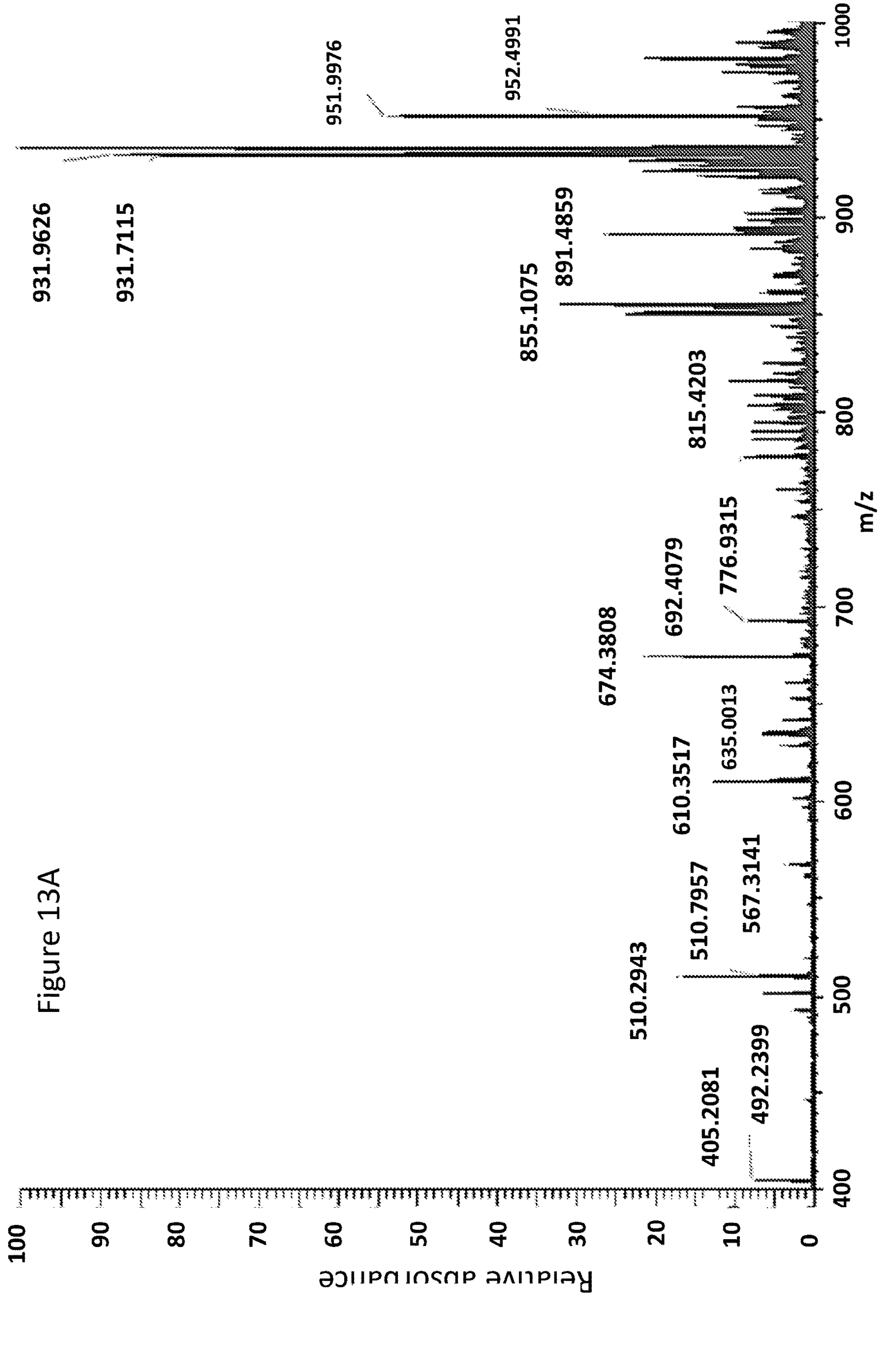
FIG. 13A-13B. ETD fragmentation spectra and matched sequence coverage for (FIG. 13A) unmodified control hOAT (SEQ ID NO: 1) and (FIG. 13B) hOAT-14 (SEQ ID NO: 1).
Figure 13A:
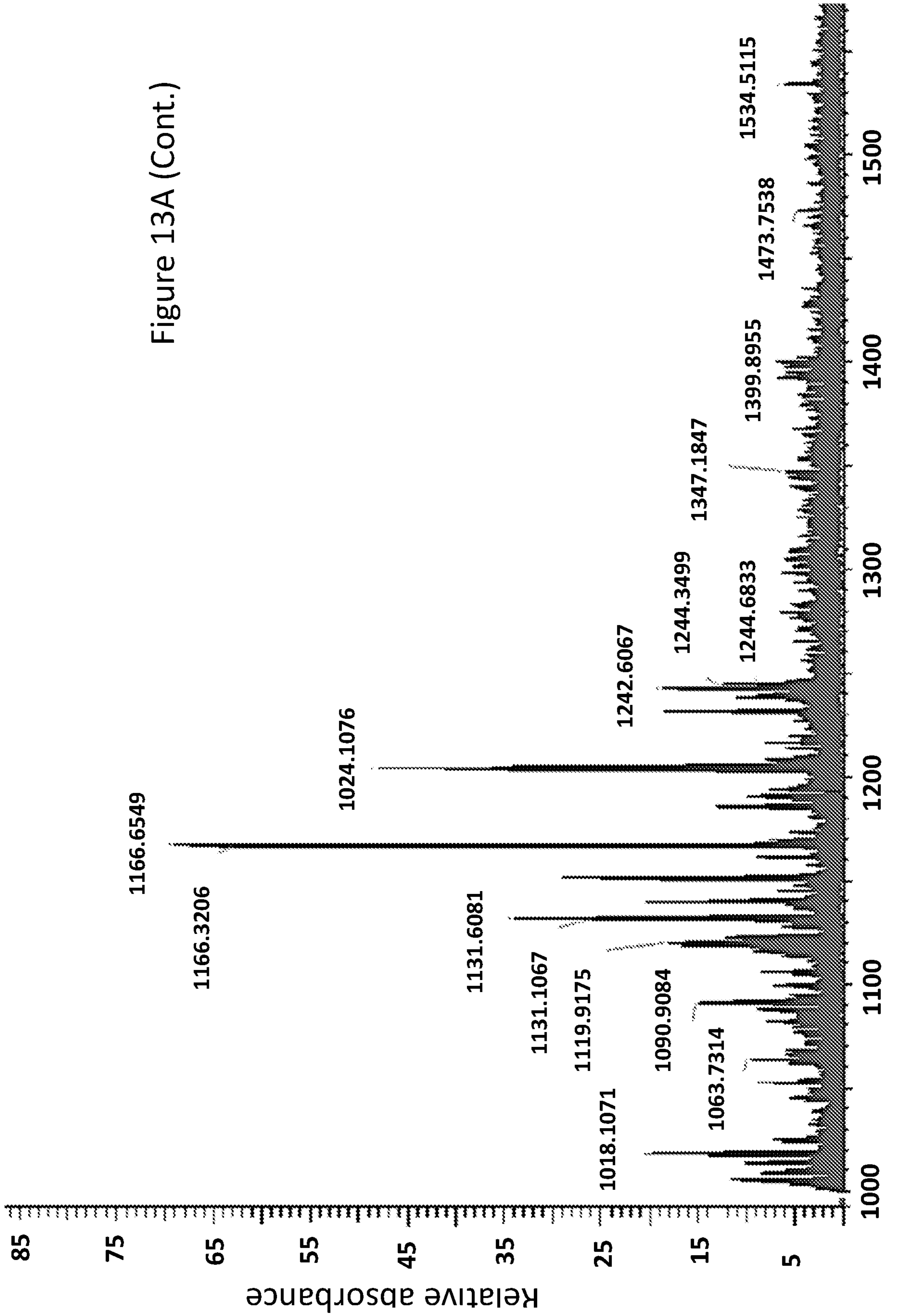
Figure 13B:
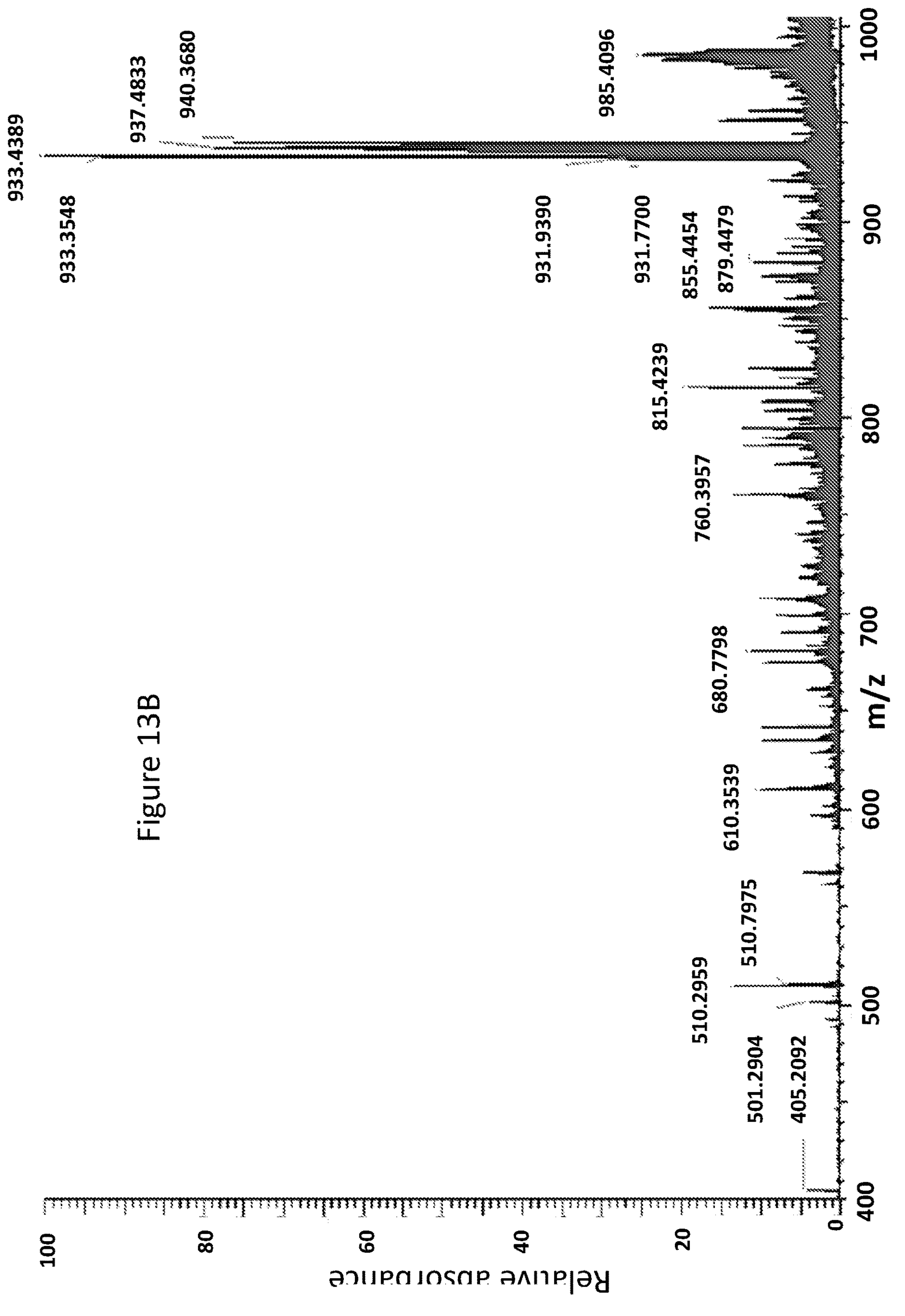
Figure 13B:
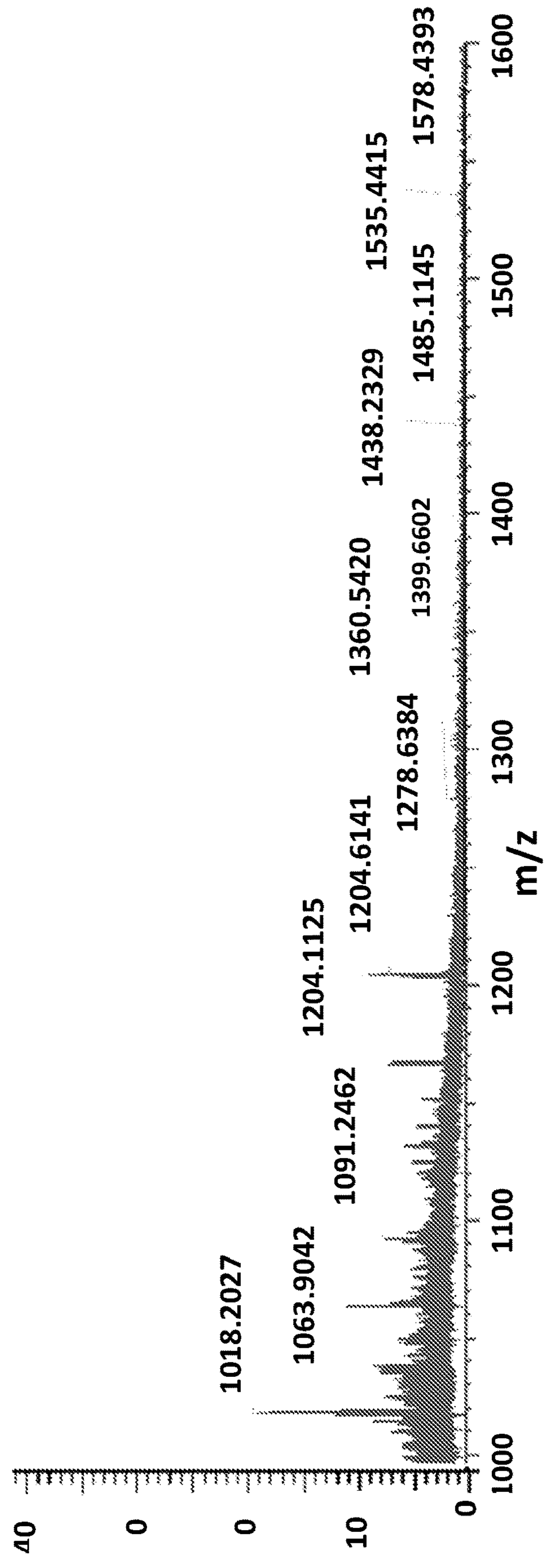

Intact protein mass spectrometry has served as an efficient tool for the identification of inactivation mechanisms for aminotransferases.[44, 50-51] The hydrolysis of unstable groups under acidic conditions, such as imine or enamine groups, has been observed with intact protein mass spectrometry to create masses that correspond to stable covalent adducts alone.[42] Accordingly, unstable adducts for 14 may suffer from similar hydrolysis and release PMP or result in cleavage of newly formed covalent bonds with Lys292/*Thr322. As shown in FIG. 12, adducts and corresponding theoretical mass differences for pathways a1-a4 and b were proposed with partial adduct loss. A range of mass shifts per monomer (148.0-166.0 Da) was proposed for pathway a1 due to different levels of hydrolysis for adduct 28. For the case of pathways a2 and a3, a mass shift of +166.0 Da was expected with the hydrolysis of PMP from adduct 30 or 31; no mass shift should be observed for tight-binding adduct 32 or 35 (pathways a4 and b).

Figure 3:
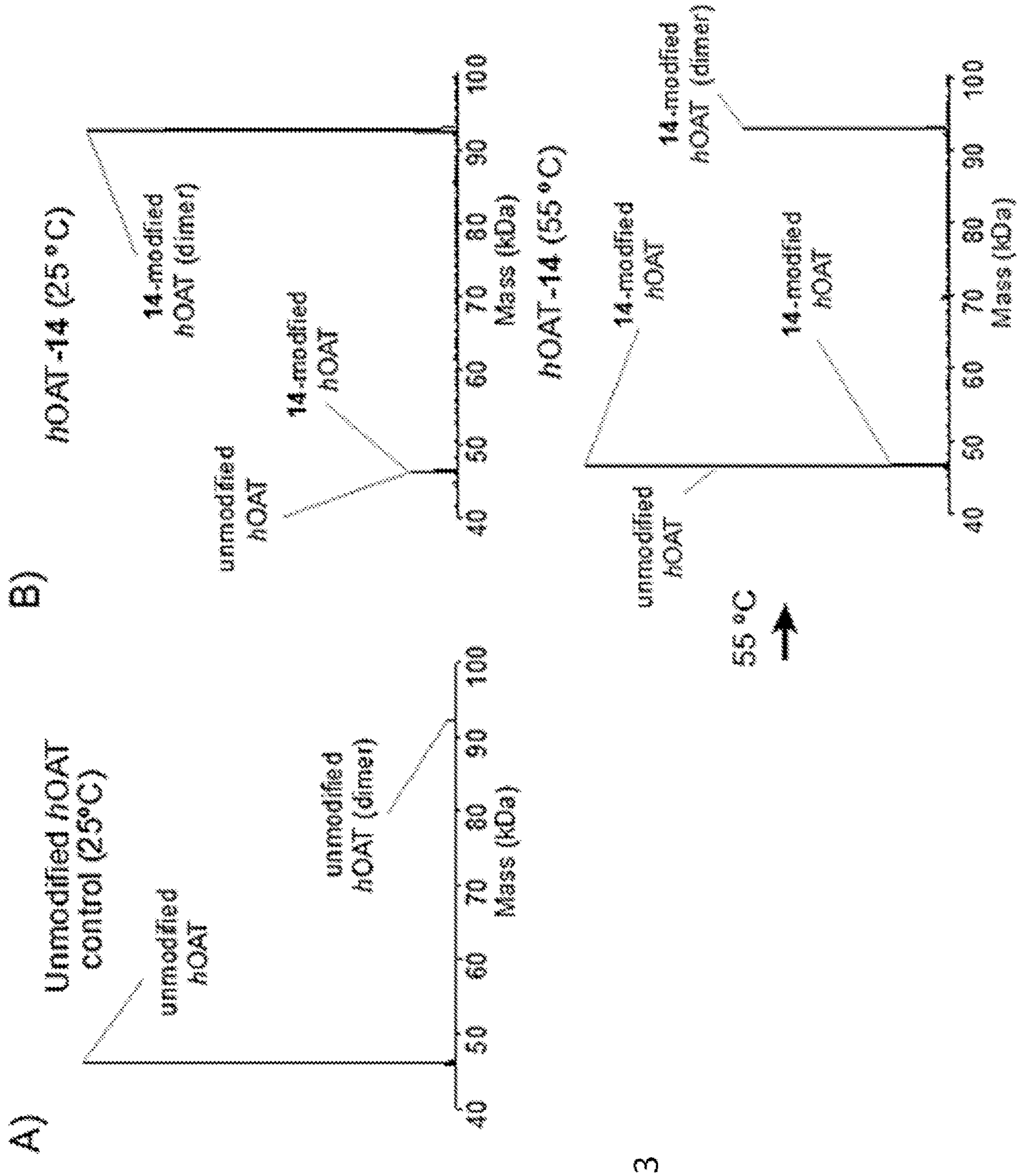
FIG. 3. Deconvoluted intact protein mass spectra for hOAT samples. (A) Unmodified hOAT. (B) hOAT-14 analyzed at 25° C. and hOAT-14 analyzed at 55° C. (C) The ratio of monomer and dimer in samples as a percent of the total protein signal. (D) Expanded view of unmodified hOAT and hOAT-14 at 25° C. from 92-93 kDa. (E) Expanded view of unmodified hOAT and hOAT-14 at 55° C. from 46-46.6 kDa.
Figure 3:
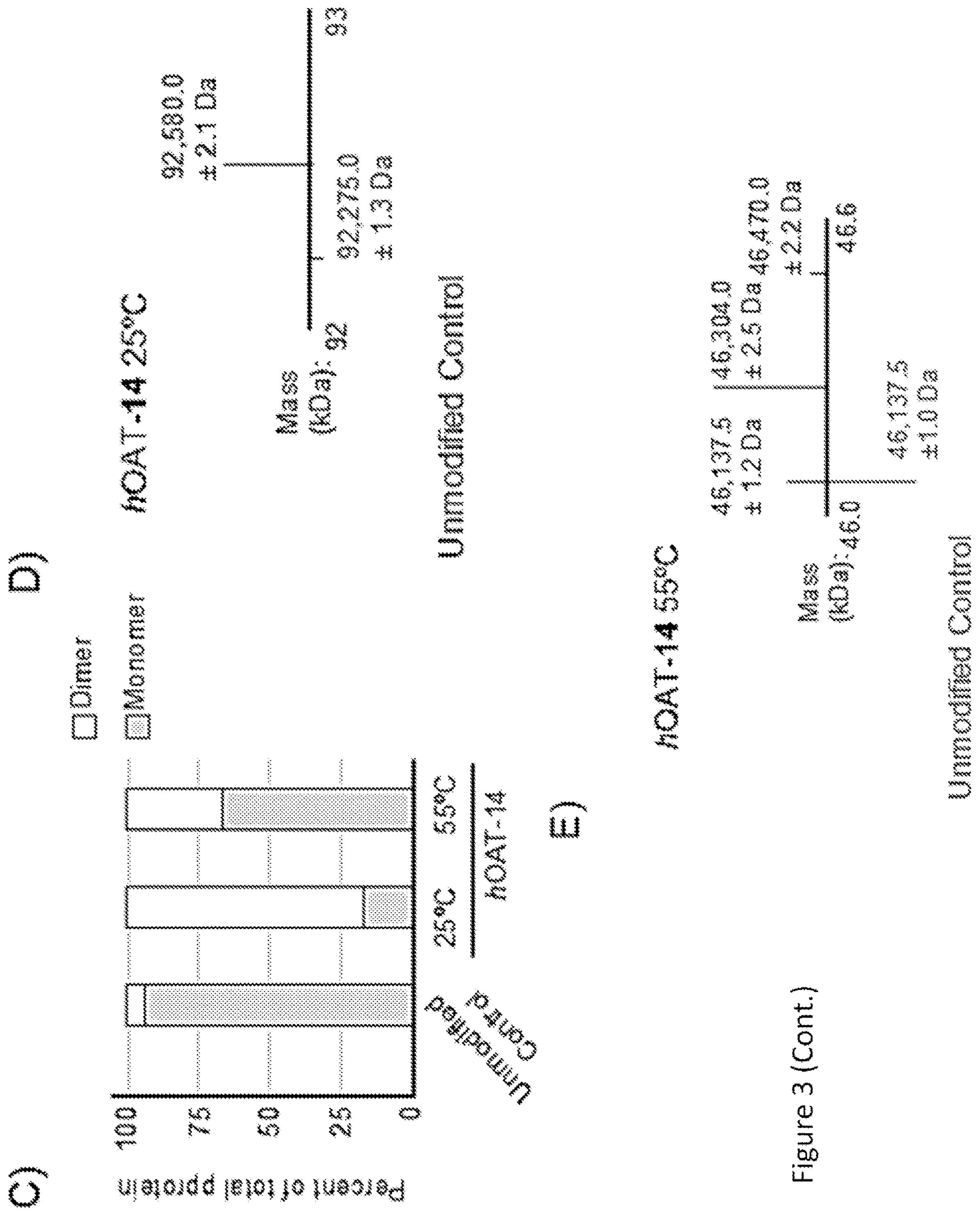

By intact protein mass spectrometry, unmodified, dimeric hOAT resolved almost entirely as monomeric protein due to acidic conditions and reverse-phase ultra-high performance liquid chromatography (FIG. 3A).[44, 50] However, under the same analytical conditions, analysis of hOAT-14 yielded a mass consistent with dimeric, cross-linked hOAT, accounting for 82% of the total protein abundance (FIG. 3B/C). Relative to the low abundance, unmodified dimer mass seen in the control (92275.0±1.3 Da), a 305.0 Da mass shift was observed for this hOAT-14 species (92580.0±2.1 Da) (FIG. 3D). The observed mass shift is not consistent with any single adduct but may result from a mixture of adducts (296.1-314.1 Da) in pathway a1 (FIG. 12). To determine if modified, monomeric hOAT could be rescued from the observed dimer, the analytical column temperature was increased from 25° C. to 55° C. Subsequent analysis of hOAT-14 at 55° C. reduced the dimer to 33% relative abundance and increased the abundance of unmodified hOAT and two additional monomeric forms of the protein (46137.5±1.0 Da; 46304.0±2.5 Da; 46470.0±2.2 Da) (FIG. 3C/E). Interestingly, the mass shifts of 166.5 Da and 332.5 Da observed for hOAT-14 monomer peaks may be explained by one (166.0 Da) and two adducts (2×166.0 Da, or 332.0 Da) each attached to a single chain (FIG. 3E), consistent with hydrolyzed adducts in pathways a1-a3 (FIG. 12).

Top-Down Proteomics.

Figure 4A:
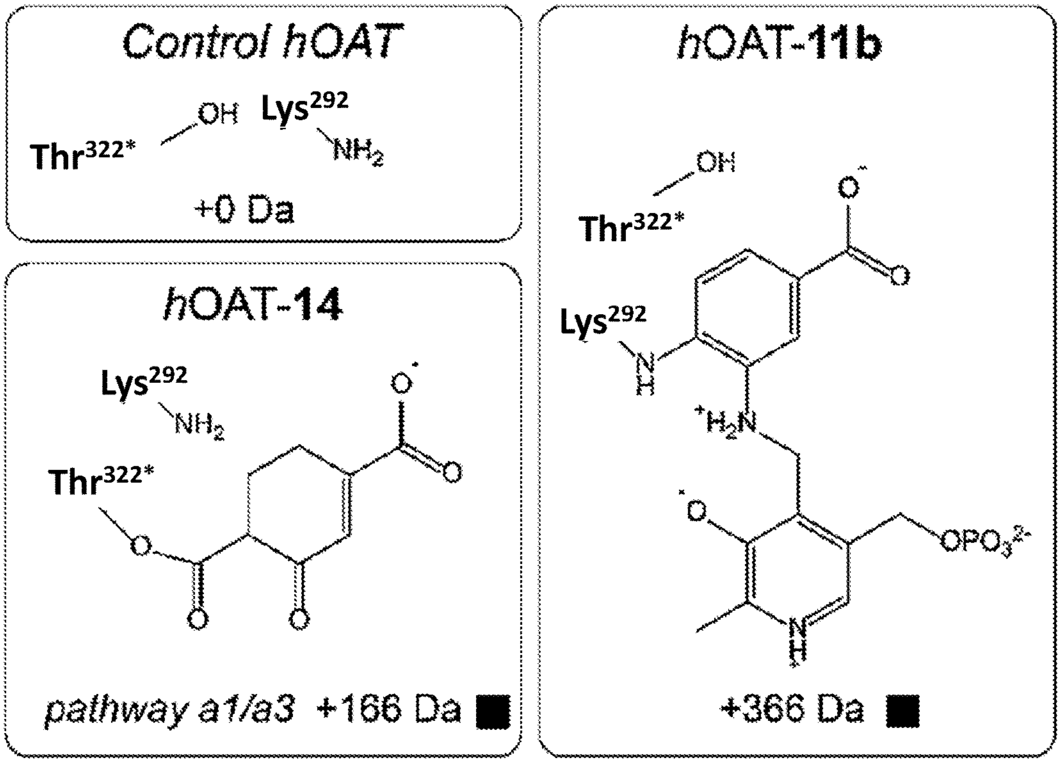
Figure 4B:
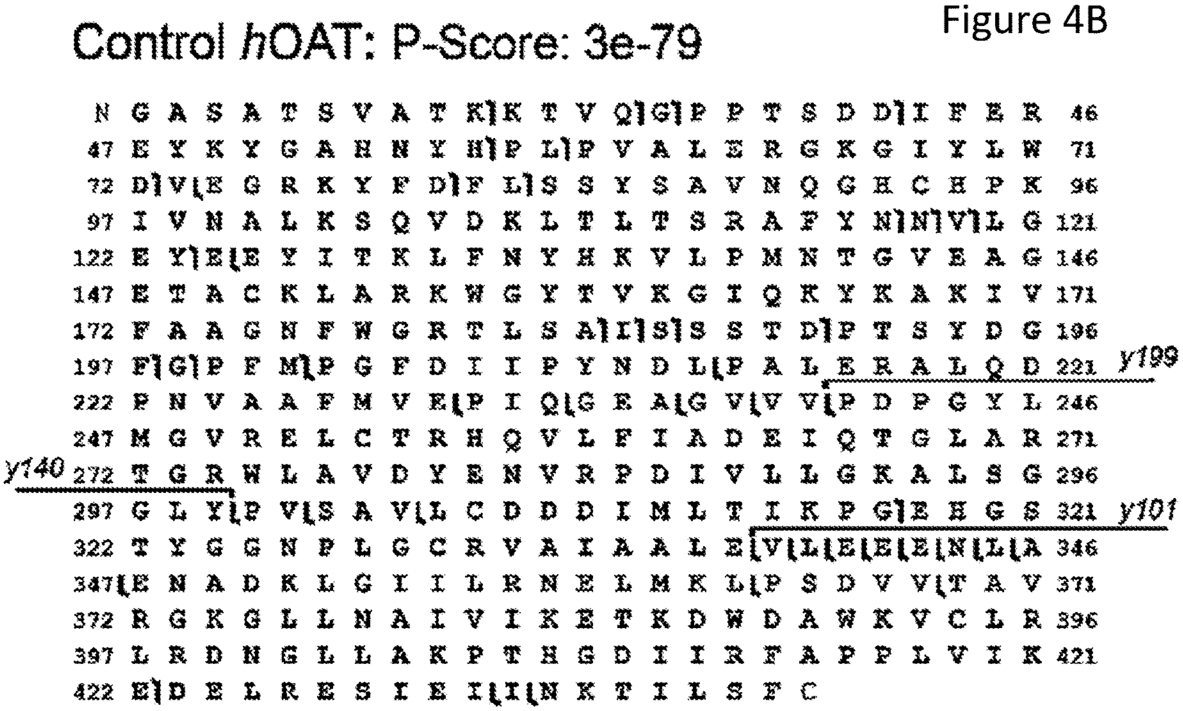
Figure 14A:
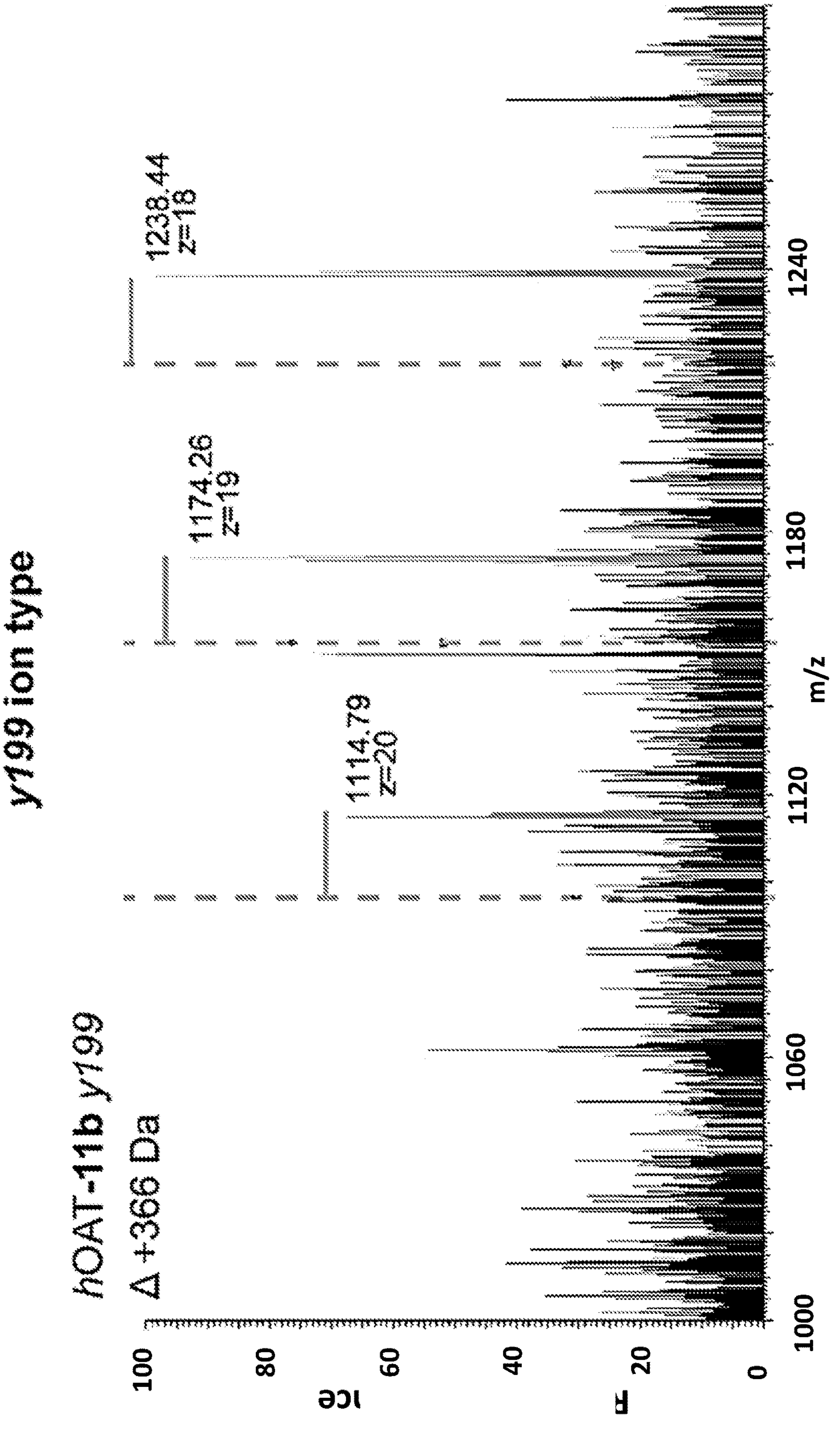
FIGS. 14A-14C. The y199 fragment ion series mass shifts for hOAT-11b and hOAT-14 adduct masses. HCD MS2 spectra insets are shown with the 20+, 19+ and 18+ charge states of y199 highlighted in blue for (A) hOAT-11b, (B) hOAT-14, and (C) unmodified control hOAT.
Figure 14B:
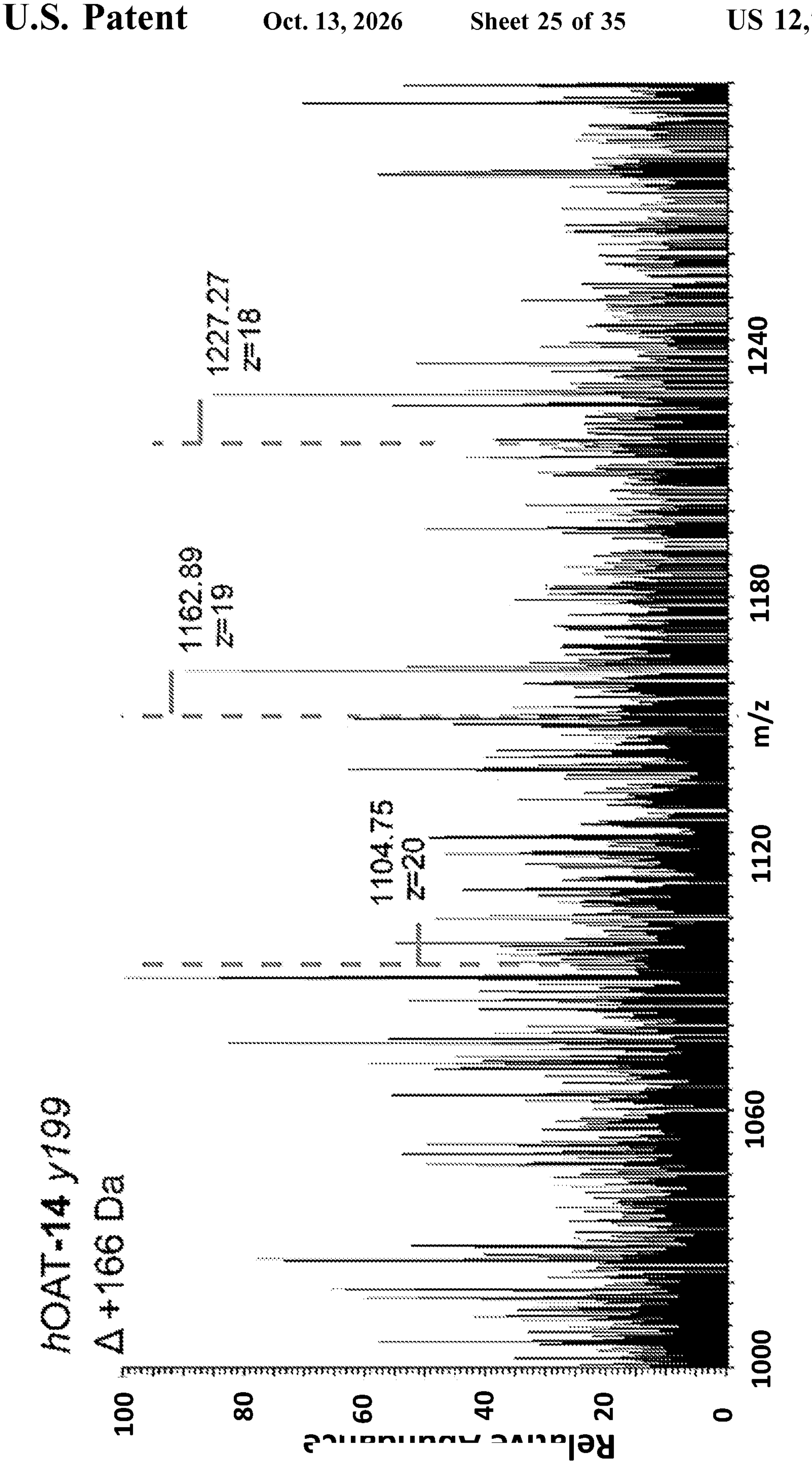
Figure 14C:
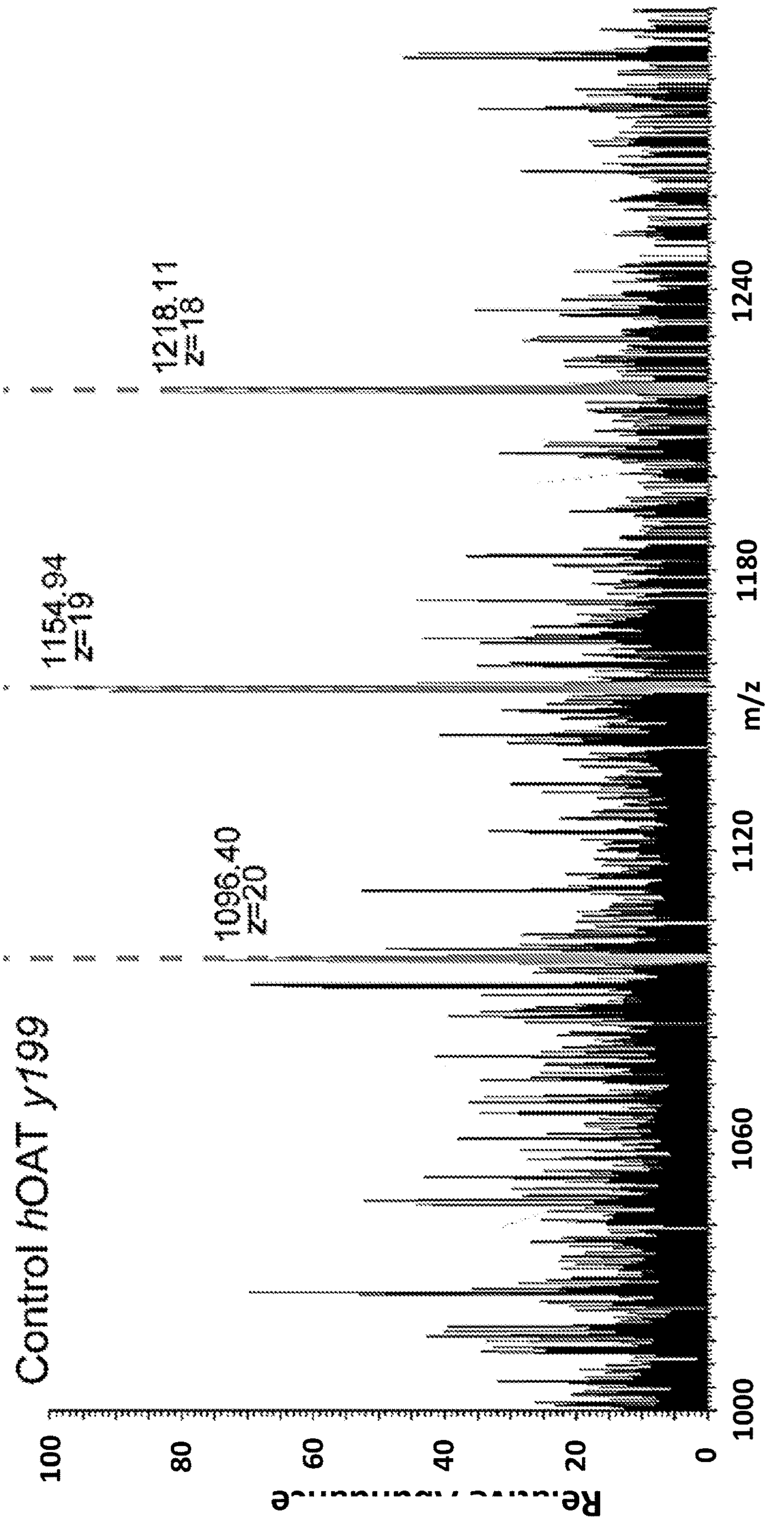
Figure 15A:
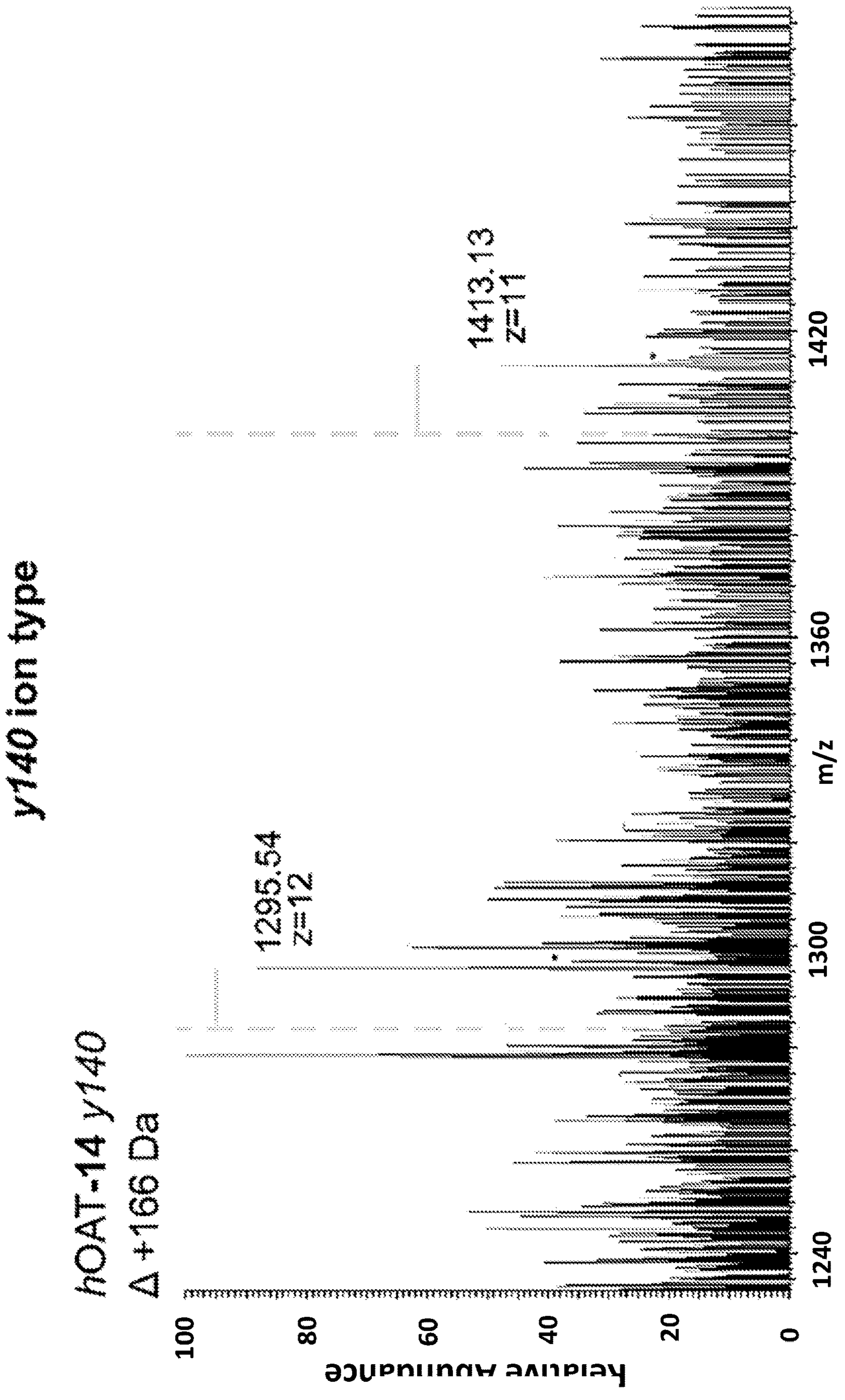
FIGS. 15A-15B. The y140 fragment ion mass shift of hOAT-14 relative to control hOAT. HCD MS2 spectra insets are shown with the $12^+$ and $11^+$ charge states of y140 highlighted in blue for (A) hOAT-14, and (B) unmodified control hOAT.
Figure 15B:
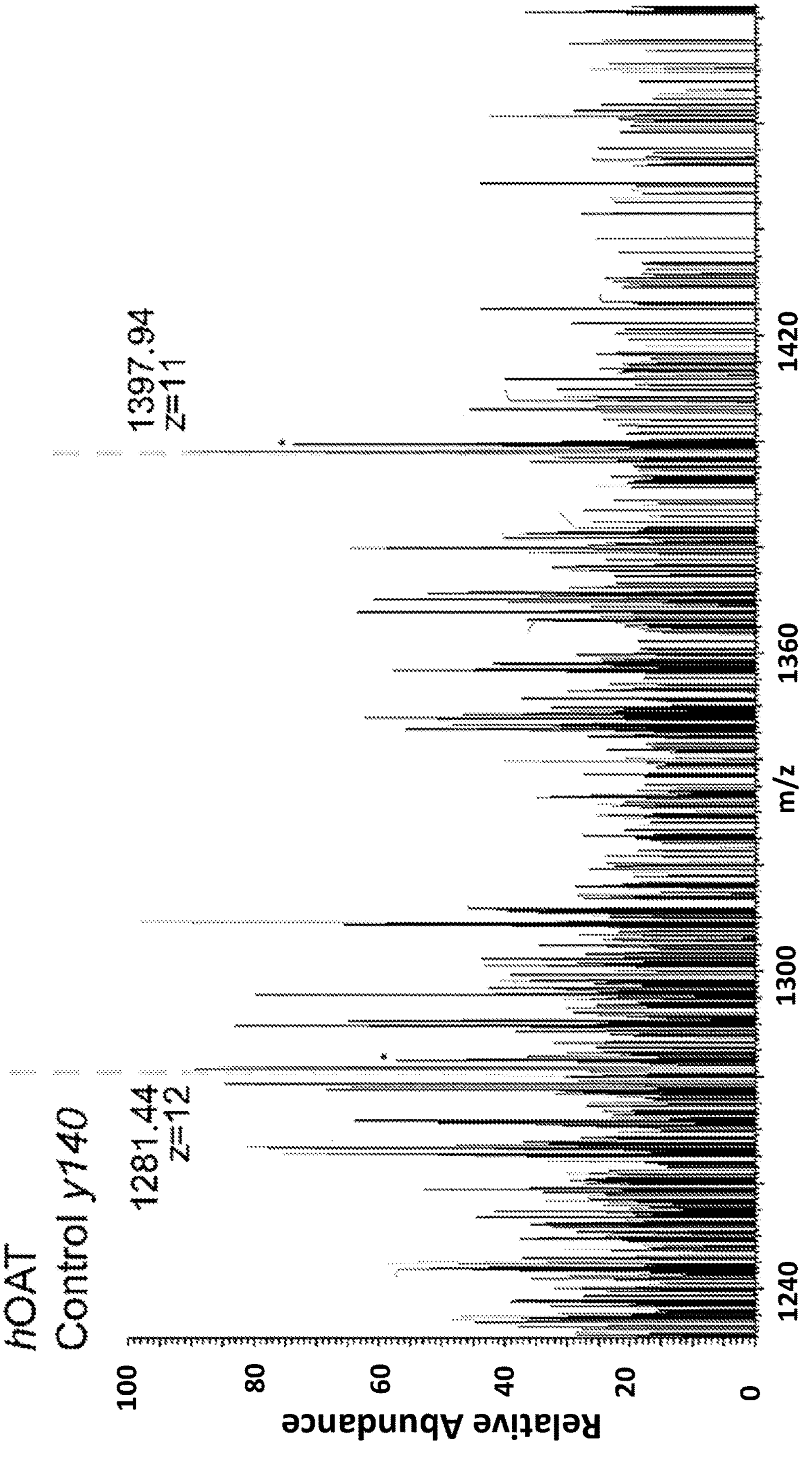

We next turned to top-down proteomics to localize the 14-induced adduct to the hOAT primary sequence. Fragmentation of hOAT-14 was first assessed using electron transfer dissociation (ETD) as this method preserves weaker covalent interactions and cross-linked peptides, and any further adduct loss was of primary concern to this study.[52-53] ETD fragmentation of hOAT-14 created a complex MS2 spectrum distinct to unmodified control hOAT and only 6 z-ions (compared to 54 z-ions for the control sample) could be mapped the protein C-terminus, all occurring after Thr322 (FIG. 13). ETD fragmentation of hOAT-14 is inconsistent with MS2 spectra for a single amino acid modification and suggests a more complex adduct. Therefore, as a complementary fragmentation method, higher-energy collisional dissociation (HCD)[54] was applied to fragment untreated control hOAT, hOAT-14, and of hOAT-11b[40] as a positive control (FIG. 4). HCD fragmentation of control hOAT generated y199 and y140 ions corresponding to the cleavage between Val239/Pro230 and Tyr298/Pro299. These ions are diagnostic and discriminant for Lys292 or Thr322 adduction (FIG. 4B, FIG. 14/15). For hOAT-11b, a +366 Da mass shift was observed for y199, consistent with the reported adduct mass (FIG. 4C).[40] Neither y140 nor any other y-ions corresponding to the cleavage between Lys292 and Thr322 were identified for hOAT-11b, possibly due to stabilizing interactions between 11b and active site residues. Nonetheless, fragmentation of hOAT-11b demonstrated method utility and adduct retention with HCD. For hOAT-14, a +166 Da mass shift was observed on both y199 and y140 (FIG. 4D, FIG. 14/15). Given the mass shift on y140 and not for the more C-terminal y101 nor subsequent y-type ions, 14-mediated adduction must occur between Tyr298 and Glu337 (FIG. 4D), consistent with Thr322 modification via pathway a1/a3 (FIG. 15).

Native Mass Spectrometry.

Figure 16:
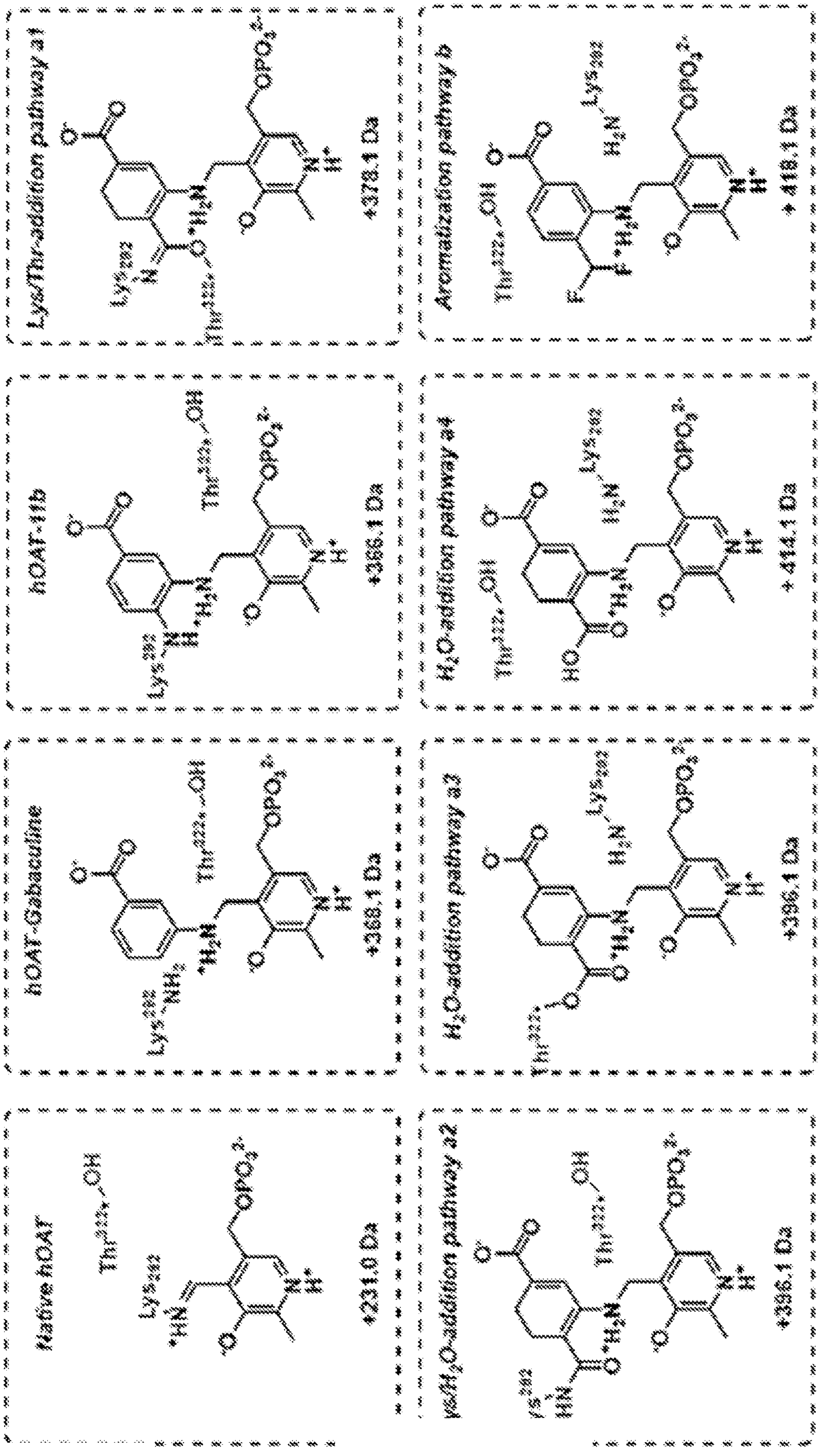
FIG. 16. Structures of proposed adducts for hOAT-11b, hOAT-Gabaculine and hOAT-14 detected by native protein mass spectrometry.
Figure 17:
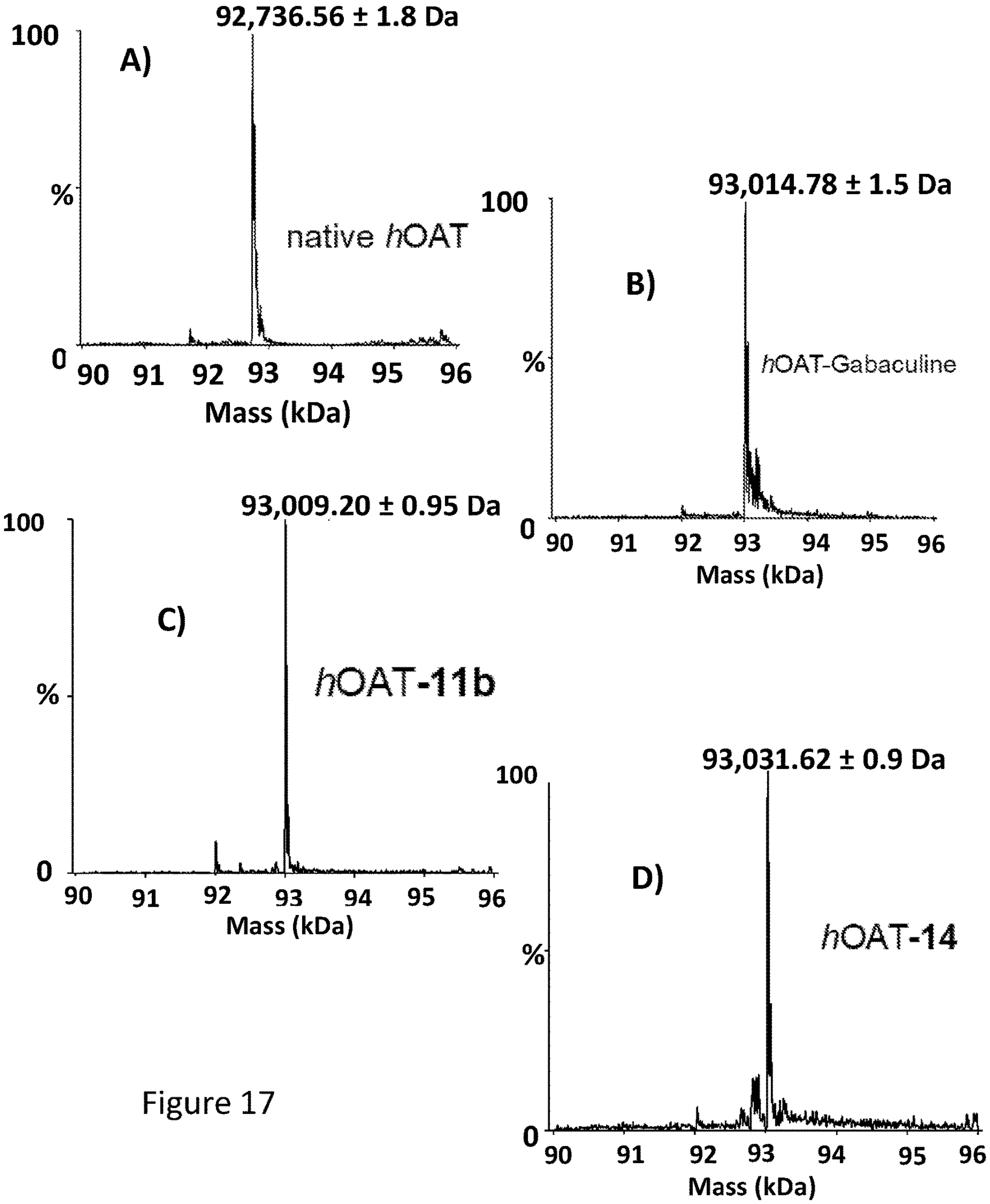
FIG. 17. Deconvoluted native mass spectra for A) untreated control hOAT, or hOAT treated with B) Gabaculine, C) 11b or D) 14.
Figure 18:
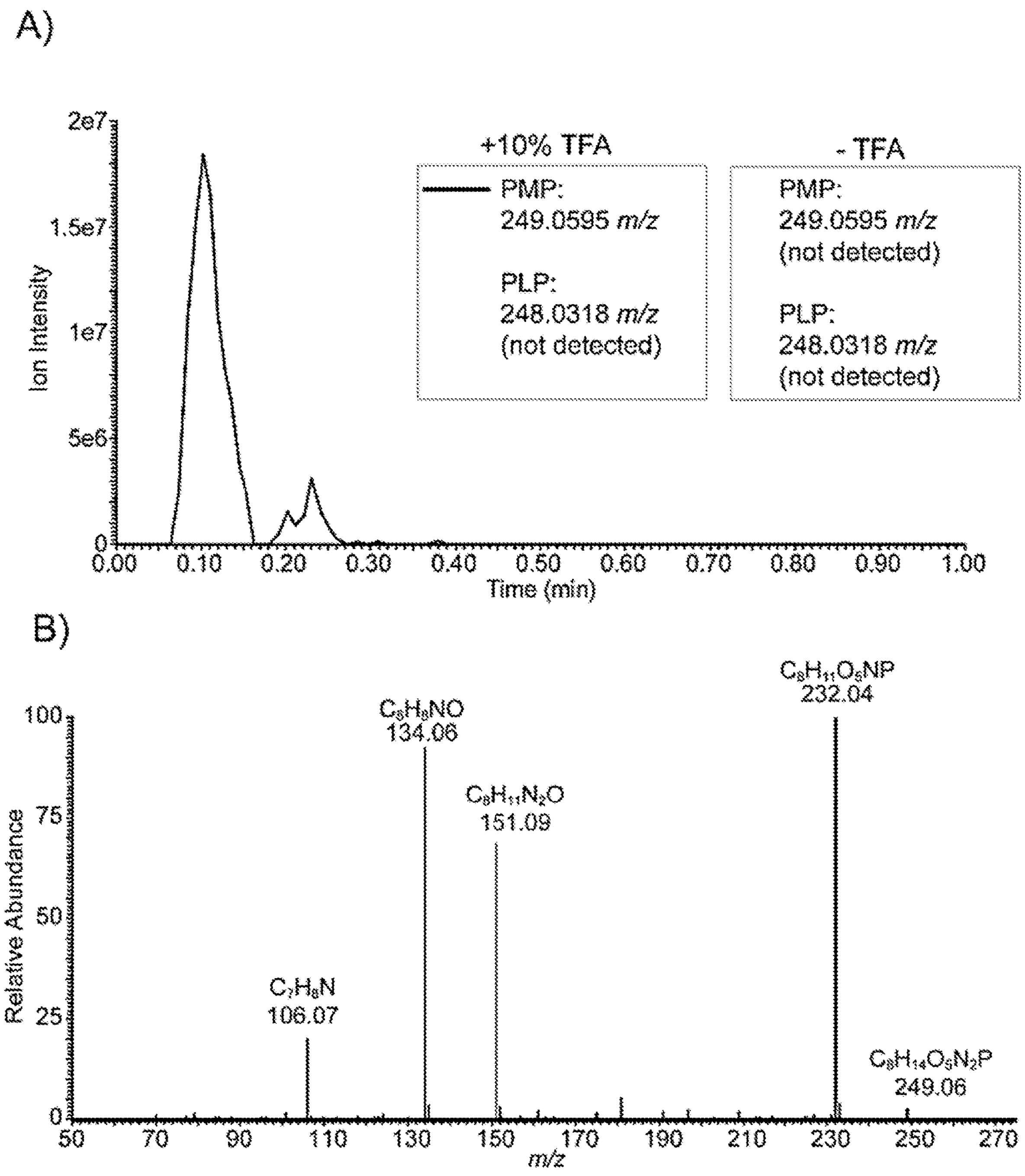
FIG. 18. Detection of PMP as the adduct cofactor for hOAT-14. (A) Extracted ion chromatogram for PLP (248.02-248.04 m/z) and PMP (249.04-249.06 m/z) with and without the addition of 10% trifluoroacetic acid (TFA). (B) MS2 confirmation of PMP.

Intact mass and complementary fragmentation studies support *Thr322 covalent modification and the crosslinking adduct 28 in pathway a1 (Scheme 4), but they cannot clearly explain the observed hOAT-14 dimer adduct mass nor the loss of adduct cofactor for hOAT-14. Therefore, to identify the adduct mass on dimeric hOAT-14, we turned to native mass spectrometry (nMS), which preserves non-covalent substrate binding and protein tertiary structure.[56] To evaluate the applicability of nMS for the study of MBIs, native untreated hOAT, hOAT-11b[40], and hOAT-Gabaculine[47] samples were first used as positive controls. In these cases, the catalytic pocket is occupied by an unstable covalent adduct, a stable covalent adduct, and a tight-binding adduct, respectively. Theoretical mass shifts for control samples were calculated based on known mechanisms; hOAT-14 mass shifts were calculated based on the proposed inactivation pathways a1-a4 and b (FIG. 16). Data were collected across protein dimer charge states and deconvoluted to average dimer masses (FIG. 17) and the experimental mass difference per monomer was calculated based on the observed average mass of the unmodified hOAT dimer (92275.0±1.3 Da, FIGS. 3A & 3D). As shown in Table 2, independent of the binding mechanism for control samples, the experimental adduct masses are consistent with their theoretical masses. Among the proposed adducts for hOAT-14, only adduct 28 from pathway a1 (Scheme 4) shows a matched mass shift (378.1 Da) with the experimental result (378.1 Da). Together, mass spectrometry-based studies support a pathway where hOAT inactivated by 14 creates a covalent, dimeric protein complex, with modification to *Thr322. Native mass spectrometry studies support hOAT-14 adduction between *Thr322 and Lys292 leading to adduct 28 within 1 Da mass accuracy for the protein dimer. This study also suggests that loss of the adduct cofactor occurs due to imine hydrolysis under the acidic conditions of intact protein MS. Indeed, using a technique we previously developed,[42] we could detect PMP as the adduct cofactor following untargeted metabolomics of the flowthrough from fully inactivated, previously desalted hOAT-14, treated with trifluoroacetic acid at 37° C. (FIG. 18). A similar loss of adduct cofactor was previously observed when an imine bond is present.[42] Together, native mass spectrometry and top-down proteomics serve as powerful tools for the future investigation of MBI characterization.

TABLE 2

The mass differences of proposed adducts between experimental and theoretical mass values of native/modified hOAT in nMS.

| Samples | Theoretical mass difference (per monomer, Da) | Experimental mass (dimer, Da) | Experimental mass difference (per monomer, Da) |
|---|---|---|---|
| Native hOAT | 231.0 | 92736.6 ± 1.8 | 230.8 |
| hOAT-Gabaculine | 368.1 | 93014.8 ± 1.5 | 369.9 |
| hOAT-11b | 366.1 | 93009.2 ± 1.0 | 367.1 |
| hOAT-14 | 378.1 (28 in pathways a1) | 93031.6 ± 0.9 | 378.3 |

X-ray Crystallography of hOAT Inactivated by 14.

Although mass spectrometry-based studies strongly indicated the formation of adduct 28 (pathway a1, Scheme 4) at the catalytic pocket of hOAT when inactivated by 14, top-down proteomics was unable to provide direct evidence for the covalent attachment to catalytic Lys292. Hence, protein crystallography of hOAT inactivated by 14 was conducted to interpret the adduct formed in the active site.

Figure 5:
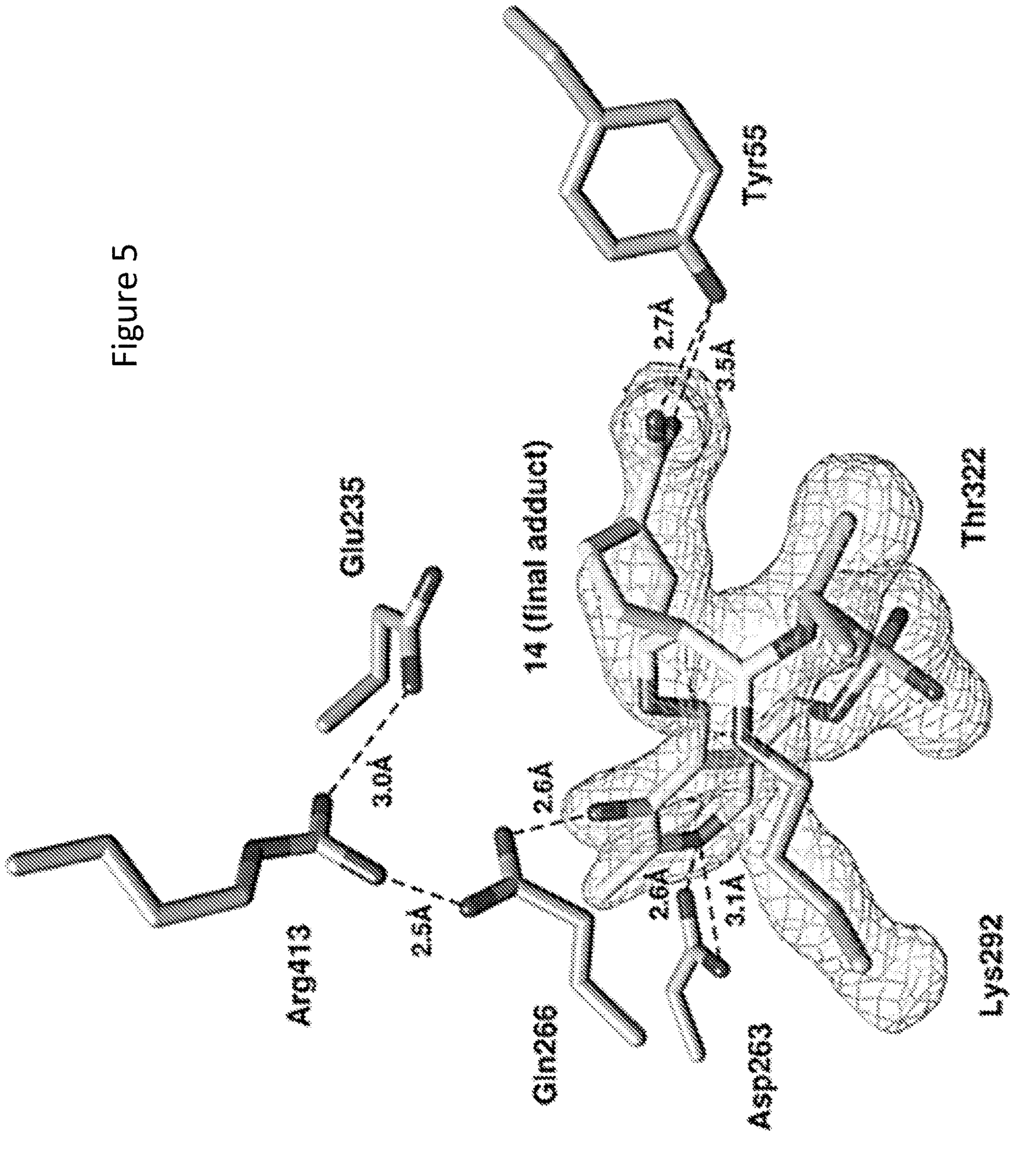
FIG. 5. $2F_o$-$F_c$ map (at 1.0σ) of hOAT-14 cocrystal structure (PDB: 7LON). Dashed lines indicated hydrogen-bonds.

The hOAT cocrystal with compound 14 was obtained and solved via a similar approach as compound 9. Similarly, two covalent bonds were formed with the adduct from Lys292 and *Thr322, which was consistent with mass spectrometry studies. Analog 14 possesses a six-member ring in its structure instead of a five-member ring as in 9, and the extra carbon provides enough length for the carboxylate group of the adduct to form hydrogen bonds with Tyr55. Because of this relatively stable interaction with the nearby residue, the intensity of electron density for the carboxylate group of adduct generated from 14 is much stronger than the adduct generated from 9 (FIG. 2). Considering the relative stability of the internal double bonds, adduct 28 was proposed initially, but it turned out that tautomer 28' (Scheme 8) with an external double bond was more suitable based on the electron density map (FIG. 5). Although the limited resolution of cocrystal (1.95 Å) does not allow us to draw a definitive conclusion on the enantiomeric form of 28', R-isomer was chosen to build into the model based on insignificantly lower Rfree factor and better fitting into the 2Fo-Fc map.

Intermediate 27 was proposed to be the active Michael acceptor for the inactivation process, whose warhead is positioned near the internal H-bond between protonated imine and oxygen anion (Scheme 4). Interestingly, the cocrystal structure for 14 demonstrated the newly formed covalent linkage is moved to the phosphate side (FIG. 5), indicating the potential imine isomerization[57-60] of the intermediate during the inactivation process. Usually, Arg413 is known to form a salt bridge with Glu235 as shown by the crystal structures of native hOAT (FIG. 10A) and inactivated hOAT (FIGS. 10B & 10C). The disruption of the salt bridges in aminotransferases was observed previously when the final adduct forms another H-bond with the arginine residue[29, 36] or there is a full occupation at the active site by a bulky adduct (FIG. 10D)[44]. Interestingly, the Arg413-Glu235 salt bridge in hOAT-14 is found to be disrupted, leading to the interaction of Arg413 with both Gln266 and Glu235. One of the oxygens in the carboxylate group of Glu235 is located 3.6 Å away from the amino group of the side chain of Gln266 and potentially could also form a hydrogen bond with this residue. However, neither Arg413 nor Glu235 forms an H-bond with the final adduct and the space close to these residues is not occupied by a bulky group, which indicates that the stable salt bridge might be broken during the inactivation process.

Molecular Docking and Molecular Dynamics (MD) Simulations.

Although the structure of the final adduct for hOAT-14 is well asserted with mass spectrometry and crystallography studies, the inactivation process is not quite clear. Two covalent bonds were formed with catalytic Lys292 and *Thr322 from the other chain, which potentially resulted from two times nucleophilic attacks at the Michael acceptor intermediate (Scheme 4), but it is hard to conclude which covalent bond is formed first. No doubt, catalytic Lys292 is more nucleophilic than *Thr322, which was found to react with active intermediates previously. However, the highly electrophilic difluoro Michael acceptor was previously disclosed to react with water molecules in the active site of the aminotransferase (Scheme 2),[29, 36] suggesting its possibility to react with *Thr322 initially. Fortunately, the cocrystal structure of hOAT inactivated by 14 (FIG. 5) provides some clues for further elucidation of the inactivation process. Imine isomerization was observed between the final adduct 28' and proposed intermediate 27, which might happen after nucleophilic attacks from the residues or result from the tautomerization of adduct 28. However, we cannot exclude the possibility of the generation of imine isomer 27' during the process, potentially due to the steric hindrance between the fluorine of the warhead and the internal H-bond (Scheme 8). The salt-bridge between Arg413 and Glu235 is disrupted as shown in the cocrystal structure (FIG. 5), which might play an important role during the inactivation process. To evaluate the potential and priority for the nucleophilic addition steps (Lys292 vs. * Thr322), molecular docking and molecular dynamics (MD) simulations of intermediates were conducted in the catalytic pockets of hOAT with salt bridge maintained and disrupted, respectively.

Figure 6A:
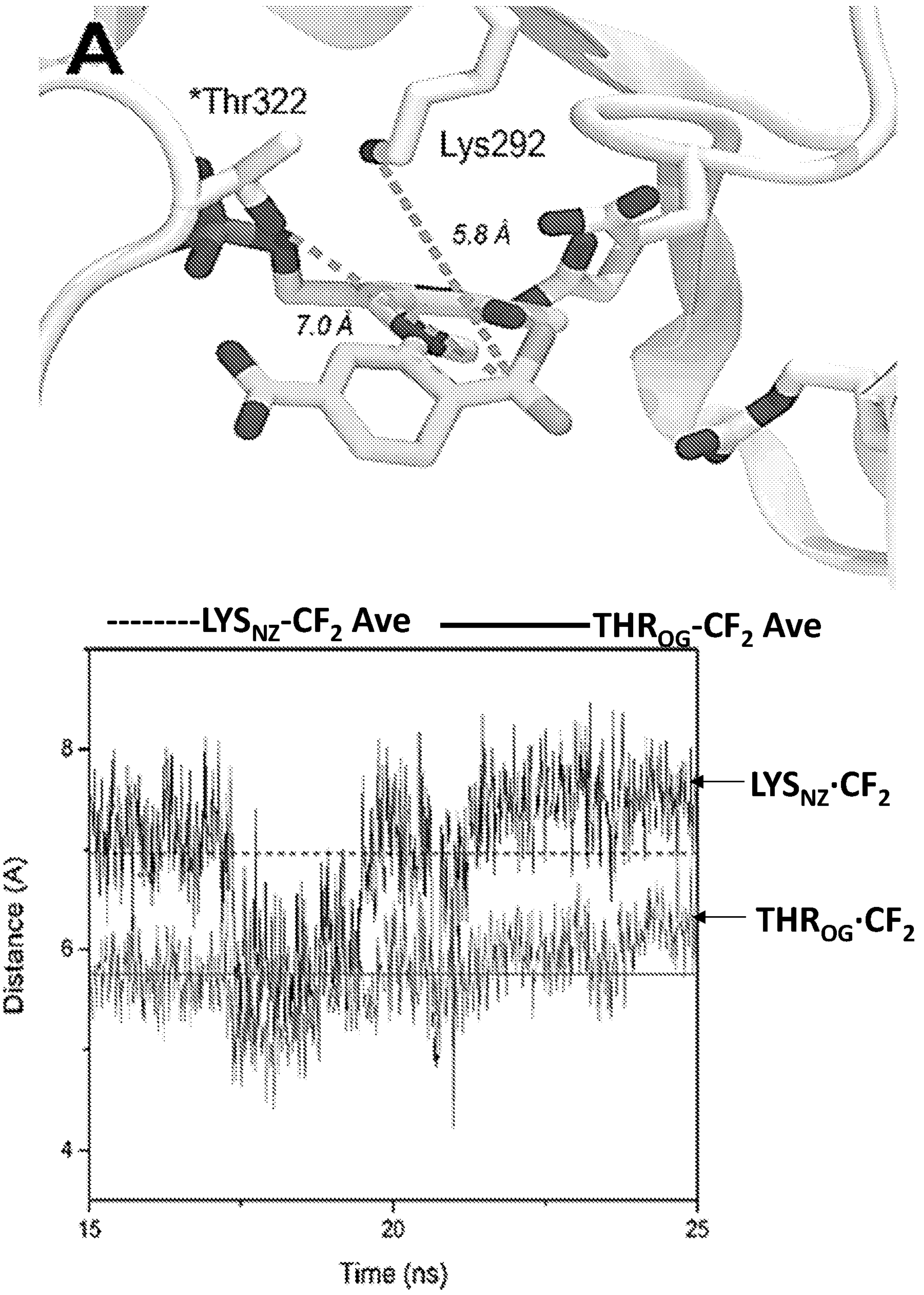
FIGS. 6A-6C. Final binding poses and average distances for the nucleophilic additions for 27 and 27' after 25 ns of MD Simulations.
Figure 20:
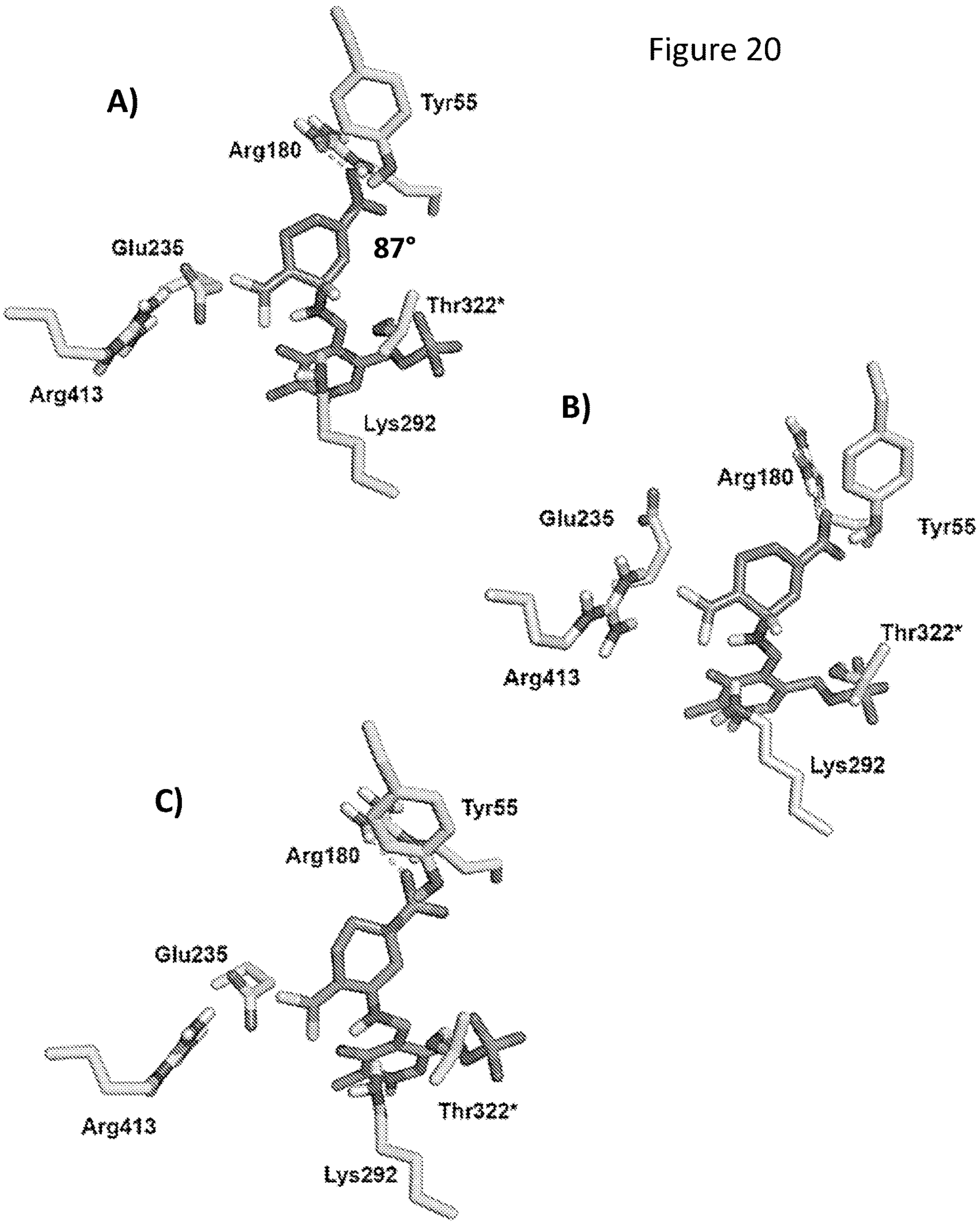
FIG. 20. Molecular docking studies. (A) Molecular docking binding pose of the 26 in the catalytic site of hOAT with salt bridge maintained (B) Molecular docking binding pose of the 26 in the catalytic site of hOAT with salt bridge disrupted. (C) Molecular docking binding pose of the 27 in the catalytic site of hOAT with salt bridge maintained. (D) Molecular docking binding pose of the 27 in the catalytic site of hOAT with salt bridge disrupted. (E) Molecular docking binding pose of the 27' in the catalytic site of hOAT with salt bridge disrupted.
Figure 20:
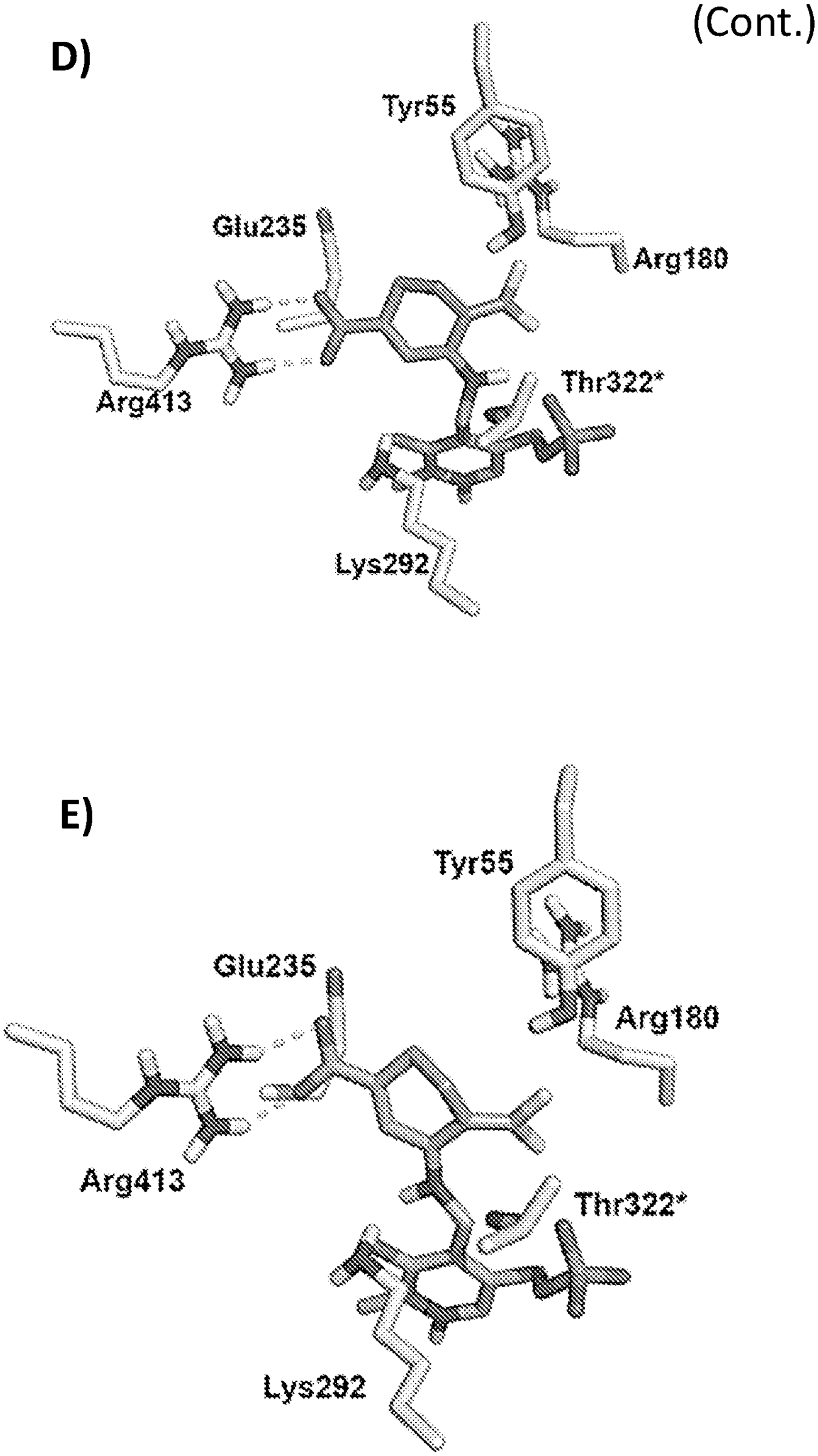

Intermediate 25 showed similar docking poses in the catalytic pockets of hOAT with the salt bridge maintained (FIG. 20A) and disrupted (FIG. 20B), in which the γ-proton is positioned close to catalytic Lys292, facilitating the following deprotonation step. Interestingly, the salt bridge status demonstrated a significant effect on the docking poses of intermediates 27 and 27'. For the case of the salt bridge maintained, carboxylate of intermediate 27 establishes hydrogen bonds with Arg180 and Tyr55, in which the warhead is located close to Lys292, Arg413, and Glu235 (FIG. 20C). No significant change was observed after 25 ns of MD simulations (FIG. 6A), whereas $C_F$ is slightly closer to the Lys292 (5.8±0.4 Å) than the *Thr322(7.0±0.8 Å), with an average difference of 1.2 Å (FIG. 6A). Considering the higher nucleophilicity of the amine group, Lys292 is prone to react with the warhead initially if this binding pose is presented in the pocket (FIG. 6A). On the other hand, isomer intermediate 27' could not fit well when the salt bridge maintained, whose PLP moiety slipped away from its original position.

When the salt bridge of hOAT is disrupted, strong interaction between Arg413 and the carboxylate of intermediate 27 was observed in the docking studies, which forced the warhead to move to the other side near Tyr55 and *Thr322

Figure 6B:
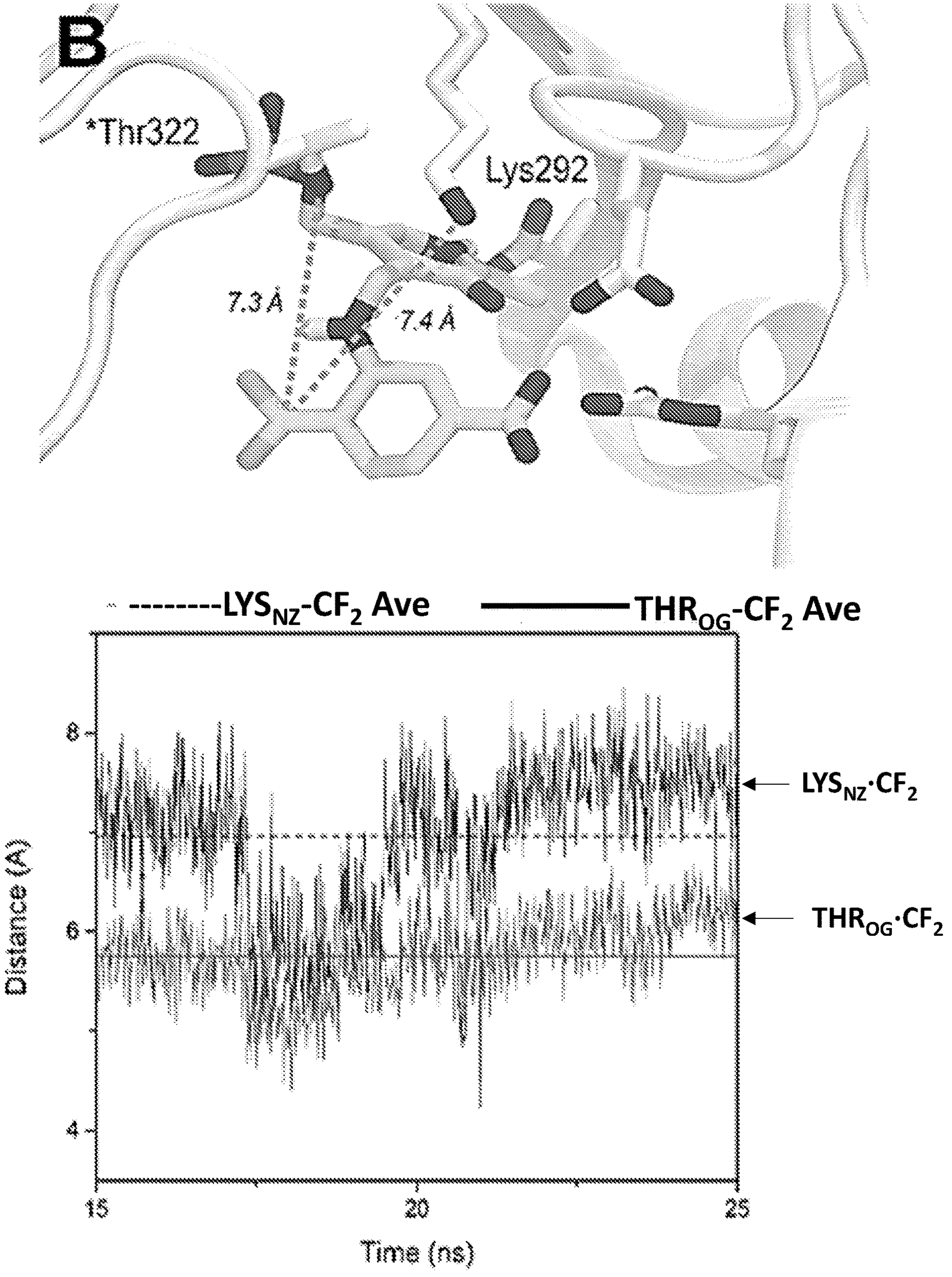
Figure 6C:
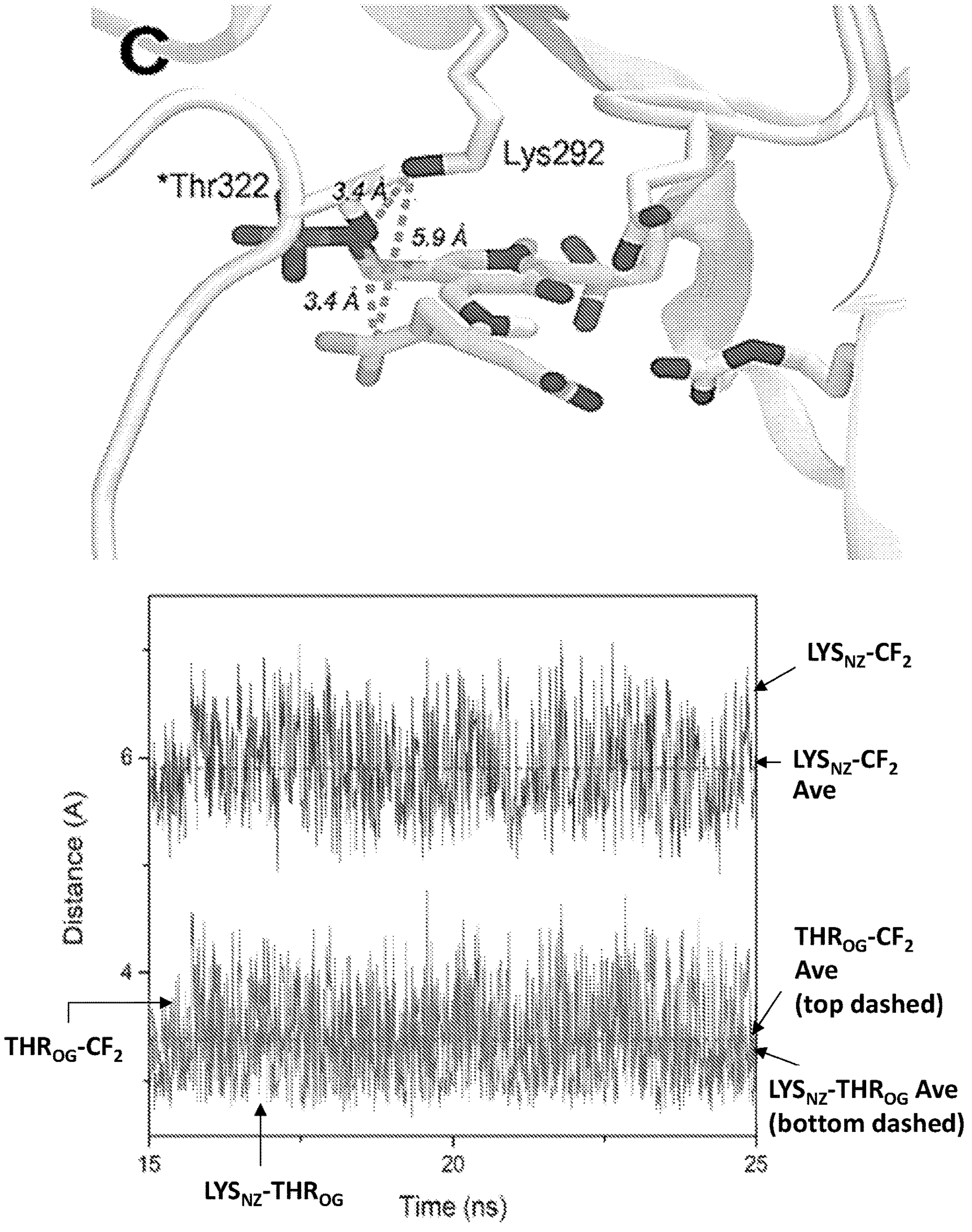

(FIG. 20D). However, the MD simulation studies showed that it failed to maintain these interactions and the warhead group was staying away from both Lys292 (7.4±0.3 Å) and *Thr322 (7.3±0.7 Å), indicating the inactivation couldn't be achieved with this binding pose (FIG. 6B). Interestingly, molecular docking results of isomer intermediate 27 showed that its carboxylate formed similar interaction with Arg413, along with its internal H-bond maintained, in the catalytic pocket of hOAT with the salt bridge disrupted (FIG. 20E). MD simulation studies confirmed the stable interaction between 27' and surrounding residues, maintaining its warhead moiety positioned much closer to *Thr322 (3.4±0.3 Å) than Lys292 (5.9±0.4 Å), which favors the reaction with the threonine residue (FIG. 6C). Notably, Lys292 is positoned nearby *Thr322 with an average distance of 3.4±0.5 Å (FIG. 6C), which is similar to the observation in the cocrystal structure of hOAT with tight-binding adducts (FIGS. 10B & 10C). Thus, we hypothesized that final adduct 28' could be generated either from intermediate 36 or 49, determined by the order of nucleophilic additions (Scheme 8).

X-ray Crystallography of hOAT Resulting From 14 Soaking.

As indicated in the above molecular docking and MD simulation studies, the order for the nucleophilic addition of two residues could be potentially determined by different binding poses of 27 (FIG. 6A) and 27' (FIG. 6C), whose carboxylate interacts with either Arg180 or Arg413 based on the different status of the salt bridge. Previously, we successfully obtained the active intermediate for hOAT inactivated by 10 via soaking experiments.[61] To distinguish which binding pose is more dominant, the soaking experiments of hOAT with 14 were performed. Holoenzyme hOAT crystals were obtained within four days and then soaked with 5 mM compound 14 (1 μL added to a 4 μL hanging drop) for different time frames from 17 to 44 minutes. After soaking the crystals were transferred to a cryo-protectant solution and flash-frozen in liquid nitrogen. The crystal soaked for 44 minutes diffracted to the resolution of 2.1 Å, its structure was solved using molecular replacement and then compared to the hOAT-14 cocrystal structure.

Figure 19:
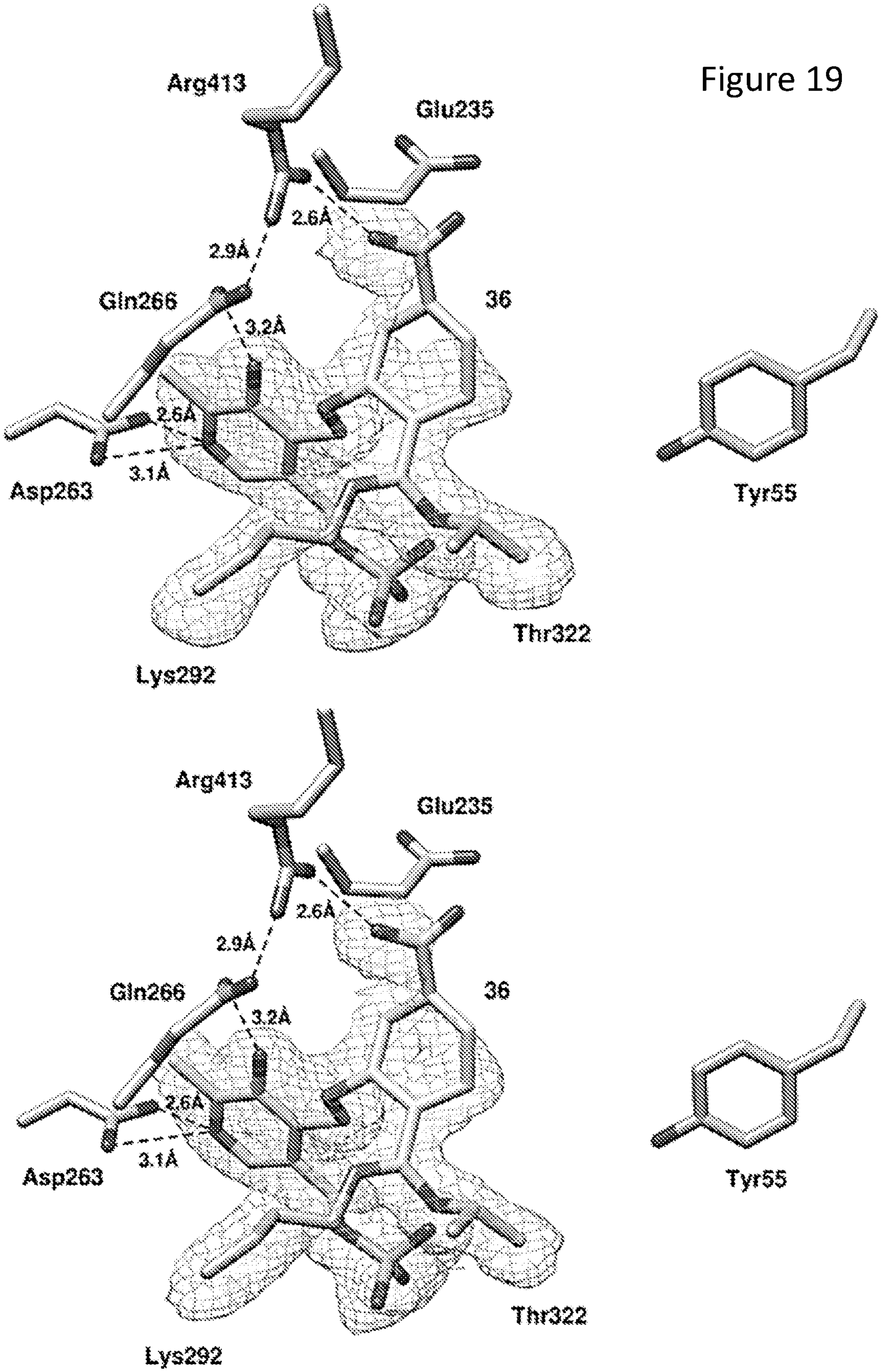
FIG. 19. $2F_o$-Fc map (at 1.0σ) of hOAT-14 soaking structure (top). Polder map (at 3.0σ) of hOAT-14 soaking structure (bottom). Dashed lines indicate hydrogen-bonds.

Intermediate 36 (Scheme 8) was trapped in the soaking study of hOAT and 14 (FIG. 7), as indicated in one out of three copies in the asymmetric unit, in which the electron density demonstrates the connection of the warhead and *Thr322. Relatively weak electron density for the covalent bonding of Lys292 and the warhead can be still observed in two other protein copies (FIG. 19), suggesting some proportion of Lys292 has already reacted with the warhead of 36. Importantly, the Arg413-Glu235 salt bridge is disrupted and the "free" arginine residue establishes a stable H-bond with the carboxylate of 36, which can well explain the broken salt bridge in the cocrystal structure of hOAT inactivated by 14 (FIG. 5). Overall, the soaking structure is quite similar to the docking pose of active intermediate 27' (FIG. 20E), whose warhead is positioned close to *Thr322 with an internal H-bond maintained. Encouraged by the above experiments, adduct 36 was proposed to be formed by the nucleophilic attack of *Thr322 on the warhead of intermediate 27', followed by the reaction with Lys292 to afford final adduct 28'.

Turnover Mechanism.

MBIs act as native substrates to bind at the catalytic pockets of target enzymes initially, thus it is common that certain amounts of MBIs will be converted to corresponding metabolites during the inactivation process.[25] Based on the reported turnover mechanism for 1 and 5 with GABA-AT,[33, 36] two possible turnover pathways for 14 by hOAT are proposed with the release of PMP or PLP, respectively. The Lys292-assisted deprotonation of Schiff base 25 affords intermediate 26, followed by the protonation at different positions to give intermediate 27' (pathway a) or 33 (pathway b). Intermediate 27 could be further hydrolyzed with the release of PMP and metabolite 37 (pathway a1) or 38 (pathway a2), which is similar to the degradation of ornithine by hOAT (Scheme 1). On the other hand, the reaction of intermediate 33 with Lys292 could afford intermediate 39, followed by the release of PLP and metabolite 40 (pathway b1) or 42 (pathway b2). Enamine 40 could be hydrolyzed to give ketone 41; imine 42 could undergo aromatization to generate metabolite 43 or 45. To identify which above-mentioned turnover pathway is involved, partition ratio and fluoride ion release experiments and the mass spectrometric analysis of metabolites were carried out.

Scheme 5. Possible turnover mechanisms for 14 by hOAT.
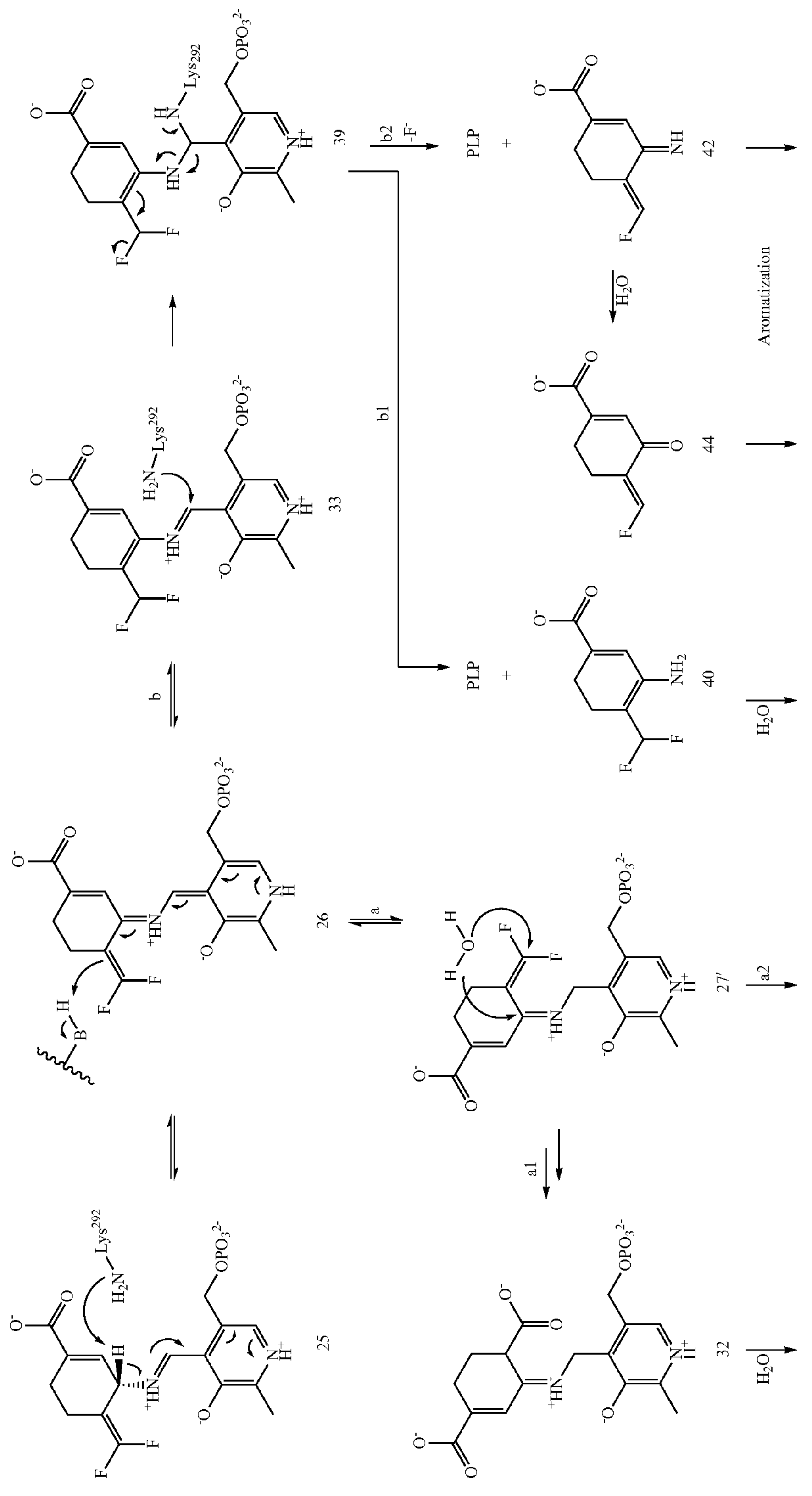
25 26 27' 32 33 39 40 42 44

-continued
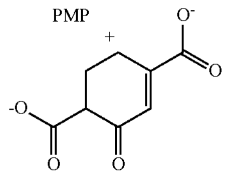
37
PMP-acid turnover
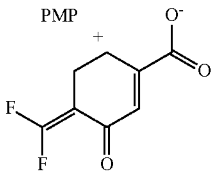
38
PMP-difluo turnover
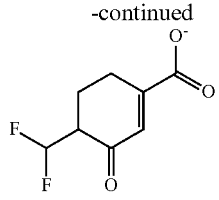
41
PLP-ketone turnover
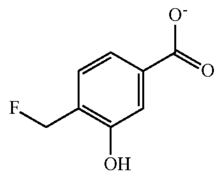
45
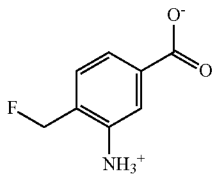
43
PLP-aromatic tunorver Partition Ratio and Fluoride Release.

Figure 21:
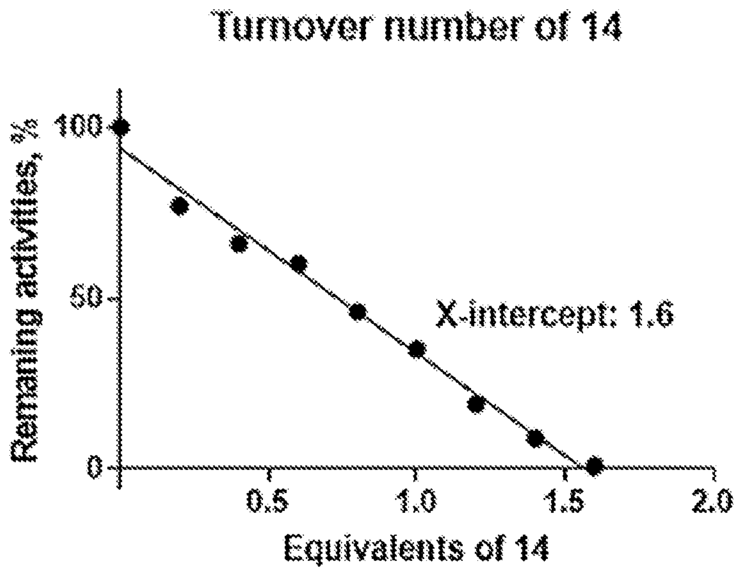
FIG. 21. Titration of an enzyme with a mechanism-based enzyme inactivator. The loss of enzyme activity is measured as a function of the ratio of inactivation to enzyme concentration. Linear regression was used on the linear portion of the curves to obtain the X-intercept, which is the turnover number (partition ratio=turnover number−1). Determination of the turnover number for 14 (Left). Determination of the turnover number for 9 (Right).
Figure 21:
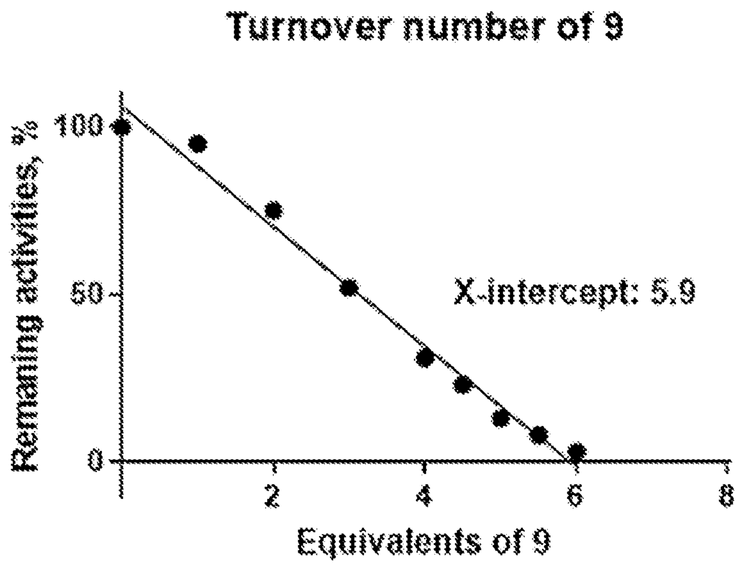

Usually, the partition ratio is used to determine the ratio of degradation and inactivation, calculated by titrating the enzyme with varying equivalents of inactivator. Ideally, a linear relationship (between enzyme activity remaining and equivalents of compounds) can be extrapolated to yield the exact equivalents (the intercept with the x-axis, turnover number) required to inactivate the enzyme completely. Since this obtained number includes the one molecule of inactivator required to inactivate one enzyme monomer, the partition ratio is the turnover number minus one. Therefore, the partition ratios of 5 and 14 were determined by titrating hOAT with varying equivalents of inactivators (FIG. 21). From this, we determined the partition ratio of 5 to be 4.9 and the partition ratio of 14 to be 0.6. The enlarged ring not only enhances the potency and selectivity against hOAT but also improves the efficiency of the inactivation.

Different equivalents of fluoride ions can be released in PLP and PMP turnover pathways. If PMP is formed in the turnover mechanism, it cannot be converted back to PLP in the absence of α-KG, which results in at most two equivalents of fluoride ion released (pathway a); more equivalents of fluoride ion would be released in the presence of α-KG if PMP is formed after the fluoride ion release step (pathway a1). If PLP is regenerated during the turnover mechanism, at least two equivalents of fluoride ions will be released in the absence of α-KG (pathway b), which should be close to the equivalents in the presence of α-KG. Based on the partition ratio and the confirmed inactivation mechanism for 14, the theoretical equivalents of fluoride ions, which are released per enzyme active site in different turnover pathways, can be calculated in the presence/absence of α-KG (Table 3). The concentration of released fluoride ions can be monitored by a fluoride ion-selective electrode. When OAT was inactivated with an excess of 14, 2.95 equivalents of fluoride ions were released in the presence of α-KG and 2.66 equivalents of fluoride ions were released in the absence of α-KG (Table 3). These results indicate the regeneration of PLP is involved in the turnover mechanism for 14, in which the experimental fluoride ions released are close to the theoretical calculation result in turnover pathway b2.

TABLE 3

Fluoride release in different turnover pathways with/without the presence of α-KG.

| Conditions | Pathway a1 | Pathway a2 | Pathway b1 | Pathway b2 | Experimental |
|---|---|---|---|---|---|
| With α-KG | 3.2 equiv | 2.0 equiv | 2.0 equiv | 2.6 equiv | 2.95 equiv |
| Without α-KG | 2.0 equiv | 1.3 equiv | 2.0 equiv | 2.6 equiv | 2.66 equiv |

Mass Spectrometry-Based Analysis of Turnover Metabolites.

Figure 8A:
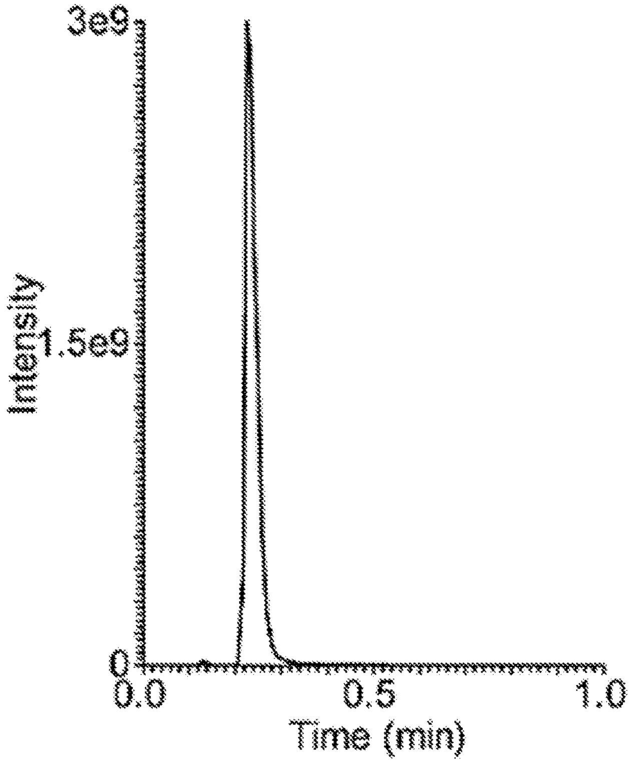
FIGS. 8A-8B. Detection of metabolite 43 as turnover metabolites for hOAT-14.
Figure 8B:
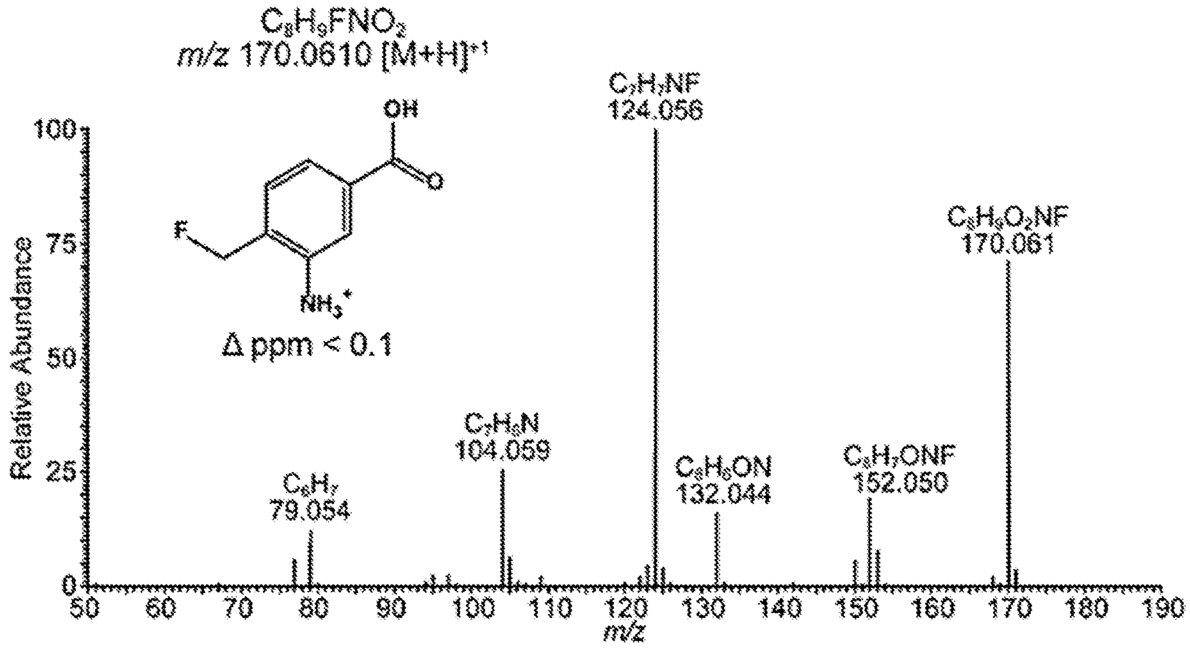

To identify the potential metabolites generated during the inactivation process of OAT by 14, inactivated OAT sample was filtered through a 10 kDa MWCO filter, followed by the untargeted metabolomics (+/−ESI HRMS) analysis of the obtained filtrate. Among the possible metabolites proposed in Scheme 5, only metabolite 43 (observed: 170.0610 m/z, $[M+H]^+$; theoretical: 170.0612 m/z) in pathway b2 was detected, followed by the confirmation of its fragmentation spectrum (FIG. 8). Notably, metabolite 45 in pathway b2 was not observed by MS, indicating the aromatization step was much faster than the hydrolysis step. Precursor 42 was generated in the catalytic pocket that is not filled with "free" water molecules as the outside. Thus, we believe 42 probably has been converted to amine 43 before it's transported out of the pocket, which didn't allow further hydrolysis. Taken together, both the metabolomic result and the fluoride ion release experiments indicate that 14 undergo turnover pathway b2 with the regeneration of PLP and the release of metabolite 43 (Scheme 5).

Plausible Mechanism for 14 With hOAT.

Figure 7:
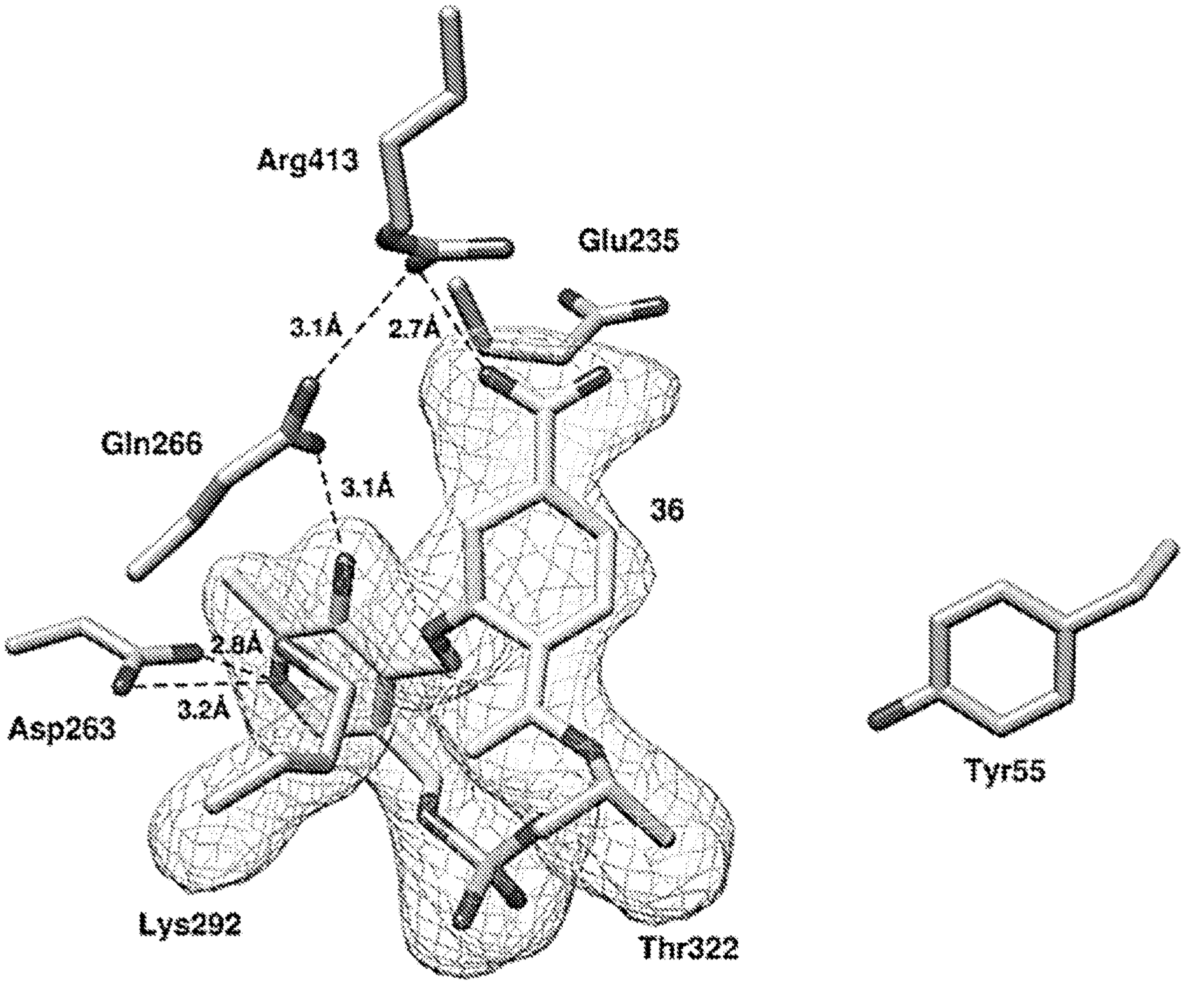
FIG. 7. $2F_o$-$F_c$ map (at 1.0σ) of intermediate 36 and Lys292 within the active site of hOAT (PDB: 7LOM). Dashed lines indicated hydrogen-bonds.

Based on the above inactivation and turnover mechanism studies, a modified pathway for 14 with hOAT is proposed in Scheme 6. Initially, Schiff base 25 was generated from 14 and PLP, followed by the deprotonation at the γ-position. According to the partition ratio (0.6) of 14 (FIG. 13), 63% of 26 is converted to active intermediate 27' with the protonation at the PLP-C4' position, in which the steric effects between the fluorine substitute and the internal H-bond potentially resulted in the imine isomerization. Molecular docking and MD simulation studies suggest the carboxylate of 27' forms stable interaction with Arg413 (FIG. 20E) when the original salt bridge is disrupted. This binding pose allows the warhead to be positioned close to *Thr322 from the other chain (FIG. 6C), leading to the formation of 36 which was trapped in the soaking crystal structure (FIG. 7). Considering the short distance (3.4 Å) between Lys292 and *Thr322 observed in the MD simulation studies of 27', Lys292 might play a role in activating *Thr322 for this nucleophilic attack, which is similar to the activation of water molecules for the case of 5/9 and GABA-AT (Scheme 2). The connection with *Thr322 pulls the warhead closer to Lys292, followed by a second nucleophilic attack (46). Finally, adduct 28' (FIG. 5) is formed to release the potential strain from two covalent attachments, while its carboxylate stays away from Arg413 and forms an H-bond with Tyr55 instead. Interestingly, Arg413 and Glu235 do not form a salt bridge later but interacts with nearby Gln266, respectively (FIG. 5). Notably, cyclopentene analog 9 is presumed to form a similar adduct, but its carboxylate fails to form a strong interaction with Tyr55 due to the short length and ring strain, resulting in a corresponding weak electron density in the cocrystal structure (FIG. 2). The formation of the double-covalent adduct (28') in the active site of hOAT-14 is supported by three types of protein MS and X-ray crystallography. On the other side, 37% of intermediate 26 is converted to intermediate 33 with the protonation at the difluoromethylene position, followed by the regeneration of PLP and the release of 43 as the final metabolite. Among the proposed metabolites (Scheme 5), only 43 were detected by MS, followed by the confirmation with its fragmentation spectrum (FIG. 8). Also, this proposed mechanism matches well with the result of fluoride ion release experiments (Table 3).

Scheme 6. Plausible mechanism for 14 with hOAT.
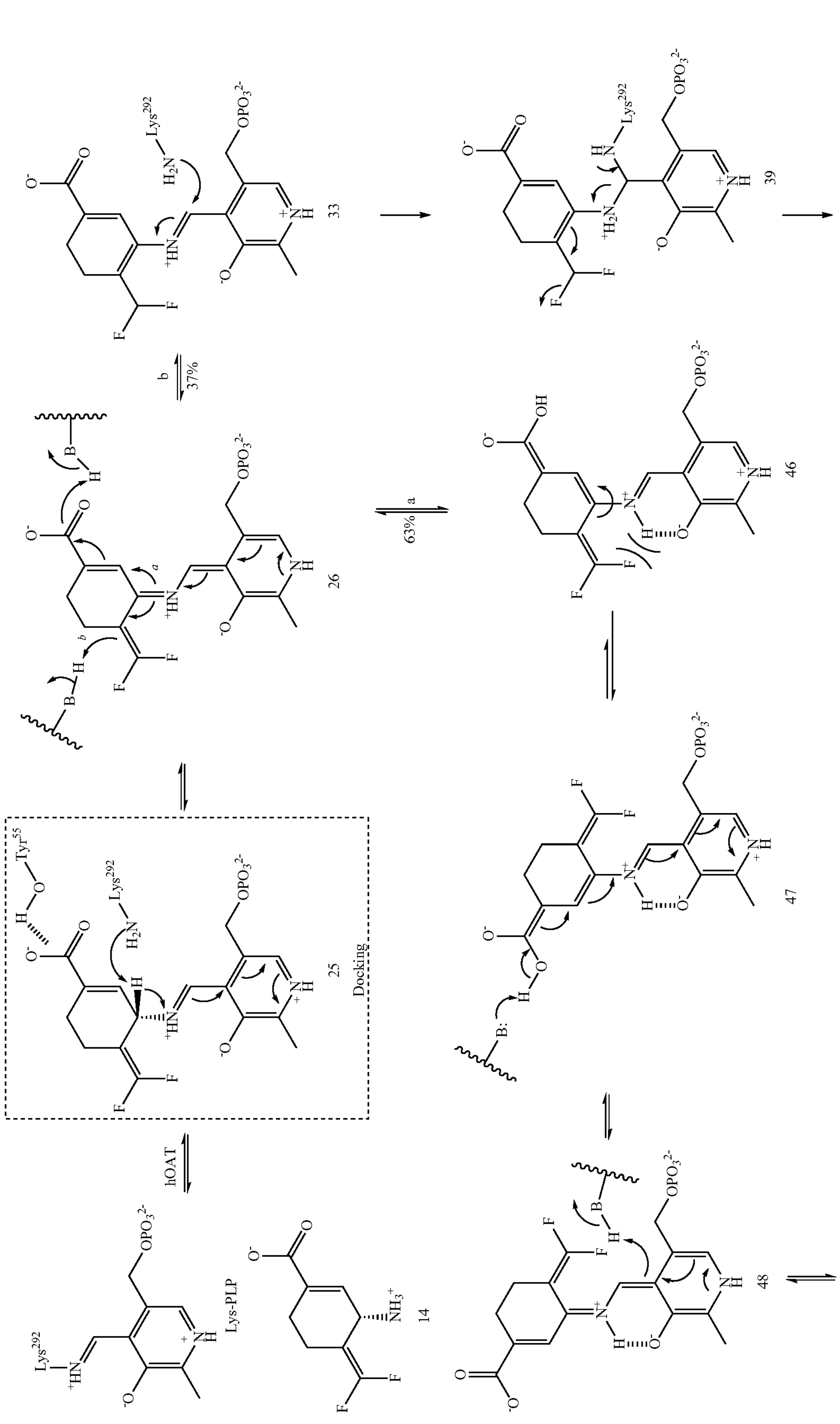
14
25
26
33
39
46
47
48

-continued
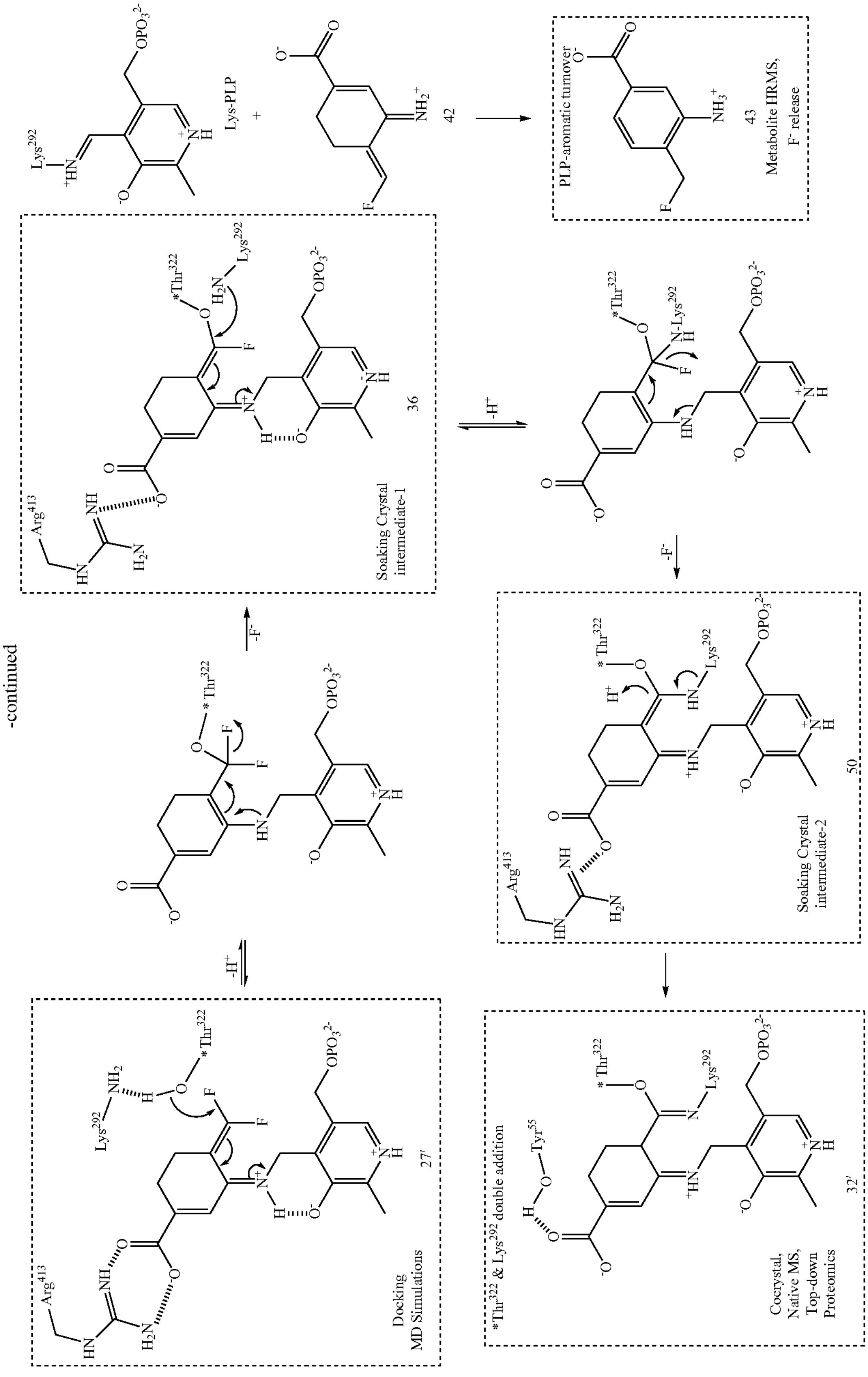
42 43 36 27′ 50 32′

Conclusions

Recently, selective pharmacological inhibition of human ornithine aminotransferase (hOAT) has been shown as a potential therapeutic approach for hepatocellular carcinoma (HCC) and other related cancers. A novel series of six-membered ring analogs (12-15) was rationally designed and chirally synthesized based on the difference in the catalytic pockets of aminotransferases. Among them, analog 14 was identified as a selective hOAT inhibitor and 18.6 times more potent than analog 10 that has demonstrated good in vivo anti-cancer activities. A plausible mechanism for 14 with hOAT was proposed (Scheme 6) based on four distinct applications of mass spectrometry, two types of protein crystallography, and molecular dynamics (MD) simulations with the aid of a dialysis experiment, total turnover, and measurement of fluoride ion release. Notably, this is the first time to successfully apply native mass spectrometry and top-down proteomics to the mechanistic study of aminotransferase inactivators. Surprisingly, double-covalent adduct 28' was formed in the catalytic pocket of hOAT via sequential nucleophilic attacks of *Thr322 and Lys292 at the warhead of active intermediate 27'. This is the first example of one single adduct forming two covalent bonds with two residues in the catalytic pocket of an enzyme, indicating a non-catalytic residue of the aminotransferase could be covalently modified by an MBI. Moreover, an interesting turnover mechanism is also demonstrated, in which aromatic metabolite 43 was generated along with the re-generation of cofactor PLP. Interestingly, no water molecule was involved in the inactivation mechanism of hOAT for 14 and its cyclopentene analog 9, while water molecules played an important role in the mechanism of 5/9 and GABA-AT (Scheme 2). We believe this mechanistic difference might derive from the enzymatic machinery of these two aminotransferases with GABA analogs, which could contribute to the further rational design of selective inactivators.

Abbreviations

DMP, Dess-martin periodinane; PMB, p-methoxybenzyl; CAN, cerium (IV) ammonium nitrate; Boc, tert-butyloxycarbonyl; KHMDS, potassium bis(trimethylsilyl)amide; DIPEA, N,N-diisopropylethylamine; Boc2O, di-tert-butyl decarbonate; m-CPBA, meta-chloroperoxybenzoic acid; $^t$BuOK, potassium tert-butoxide; DMAP, 4-dimethylaminopyridine; DMF, dimethylformamide; DCM, dichloromethane.

References

1. Sayiner, M.; Golabi, P.; Younossi, Z. M., Disease Burden of Hepatocellular Carcinoma: A Global Perspective. *Digest Dis Sci* 2019, 64 (4), 910-917.
2. Personeni, N.; Rimassa, L., Hepatocellular Carcinoma: A Global Disease in Need of Individualized Treatment Strategies. *J Oncol Pract* 2017, 13 (6), 368-370.
3. Sherman, M.; Bruix, J.; Porayko, M.; Tran, T.; Comm, A. P. G., Screening for hepatocellular carcinoma: The rationale for the American Association for the Study of Liver Diseases recommendations. *Hepatology* 2012, 56 (3), 793-796.
4. Yang, J. D.; Roberts, L. R., Hepatocellular carcinoma: a global view. *Nat Rev Gastro Hepat* 2010, 7 (8), 448-458.
5. Leathers, J. S.; Balderramo, D.; Prieto, J.; Diehl, F.; Gonzalez-Ballerga, E.; Ferreiro, M. R.; Carrera, E.; Barreyro, F.; Diaz-Ferrer, J.; Singh, D.; Mattos, A. Z.; Carrilho, F.; Debes, J. D., Sorafenib for Treatment of Hepatocellular Carcinoma A Survival Analysis From the South American Liver Research Network. *J Clin Gastroenterol* 2019, 53 (6), 464-469.
6. de Rosamel, L.; Blanc, J. F., Emerging tyrosine kinase inhibitors for the treatment of hepatocellular carcinoma. *Expert Opin Emerg Dr* 2017, 22 (2), 175-190.
7. Milgrom, D. P.; Maluccio, M. A.; Koniaris, L. G., Management of Hepatocellular Carcinoma (HCC). *Curr Surg Rep* 2016, 4 (6).
8. de Lope, C. R.; Tremosini, S.; Forner, A.; Reig, M.; Bruix, J., Management of HCC. *J Hepatol* 2012, 56, S75-S87.
9. Ginguay, A.; Cynober, L.; Curis, E.; Nicolis, I., Ornithine Aminotransferase, an Important Glutamate-Metabolizing Enzyme at the Crossroads of Multiple Metabolic Pathways. *Biology* (*Basel*) 2017, 6 (1).
10. Zigmond, E.; Ben Ya'acov, A.; Lee, H.; Lichtenstein, Y.; Shalev, Z.; Smith, Y.; Zolotarov, L.; Ziv, E.; Kalman, R.; Le, H. V.; Lu, H. J.; Silverman, R. B.; Ilant, Y., Suppression of Hepatocellular Carcinoma by Inhibition of Overexpressed Ornithine Aminotransferase. *Acs Med Chem Lett* 2015, 6 (8), 840-844.
11. Herzfeld, A.; Knox, W. E., Properties Developmental Formation and Estrogen Induction of Ornithine Aminotransferase in Rat Tissues. *J Biol Chem* 1968, 243 (12), 3327-&.
12. Herzfeld, A.; Knox, W. E., The properties, developmental formation, and estrogen induction of ornithine aminotransferase in rat tissues. *J Biol Chem* 1968, 243 (12), 3327-32.
13. Peraino, C.; Bunville, L. G.; Tahmisia.Tn, Chemical Physical and Morphological Properties of Ornithine Aminotransferase from Rat Liver. *J Biol Chem* 1969, 244 (9), 2241-&.
14. Ding, Z.; Ericksen, R. E.; Escande-Beillard, N.; Lee, Q. Y.; Loh, A.; Denil, S.; Steckel, M.; Haegebarth, A.; Wai Ho, T. S.; Chow, P.; Toh, H. C.; Reversade, B.; Gruenewald, S.; Han, W., Metabolic pathway analyses identify proline biosynthesis pathway as a promoter of liver tumorigenesis. *J Hepatol* 2020, 72 (4), 725-735.
15. Altman, B. J.; Stine, Z. E.; Dang, C. V., From Krebs to clinic: glutamine metabolism to cancer therapy. *Nat Rev Cancer* 2016, 16 (10), 619-34.
16. Phang, J. M.; Liu, W.; Hancock, C. N.; Fischer, J. W., Proline metabolism and cancer: emerging links to glutamine and collagen. *Curr Opin Clin Nutr Metab Care* 2015, 18 (1), 71-7.
17. Phang, J. M.; Liu, W.; Zabirnyk, O., Proline metabolism and microenvironmental stress. *Annu Rev Nutr* 2010, 30, 441-63.
18. Tang, L.; Zeng, J.; Geng, P.; Fang, C.; Wang, Y.; Sun, M.; Wang, C.; Wang, J.; Yin, P.; Hu, C.; Guo, L.; Yu, J.; Gao, P.; Li, E.; Zhuang, Z.; Xu, G.; Liu, Y., Global Metabolic Profiling Identifies a Pivotal Role of Proline and Hydroxyproline Metabolism in Supporting Hypoxic Response in Hepatocellular Carcinoma. *Clin Cancer Res* 2018, 24 (2), 474-485.
19. Cadoret, A.; Ovejero, C.; Terris, B.; Souil, E.; Levy, L.; Lamers, W. H.; Kitajewski, J.; Kahn, A.; Perret, C., New targets of beta-catenin signaling in the liver are involved in the glutamine metabolism. *Oncogene* 2002, 21 (54), 8293-8301.
20. Colnot, S.; Decaens, T.; Niwa-Kawakita, M.; Godard, C.; Hamard, G.; Kahn, A.; Giovannini, M.; Perret, C., Liver-targeted disruption of Apc in mice activates beta-catenin signaling and leads to hepatocellular carcinomas. *P Natl Acad Sci USA* 2004, 101 (49), 17216-17221.

21. Liu, Y. F.; Wu, L.; Li, K.; Liu, F. R.; Wang, L.; Zhang, D. L.; Zhou, J.; Ma, X.; Wang, S. Y.; Yang, S. Y., Ornithine aminotransferase promoted the proliferation and metastasis of non-small cell lung cancer via upregulation of miR-21. *J Cell Physiol* 2019, 234 (8), 12828-12838.
22. Markova, M.; Peneff, C.; Hewlins, M. J. E.; Schirmer, T.; John, R. A., Determinants of substrate specificity in omega-aminotransferases. *J Biol Chem* 2005, 280 (43), 36409-36416.
23. Mehta, P. K.; Hale, T. I.; Christen, P., Evolutionary Relationships among Aminotransferases-Tyrosine Aminotransferase, Histidinol-Phosphate Aminotransferase, and Aspartate-Aminotransferase Are Homologous Proteins. *Eur J Biochem* 1989, 186 (1-2), 249-253.
24. Cooper, A. J. L., Glutamate-Gamma-Aminobutyrate Transaminase. *Methods in Enzymology* 1985, 113, 80-82.
25. Silverman, R. B., Design and Mechanism of GABA Aminotransferase Inactivators. Treatments for Epilepsies and Addictions. *Chemical Reviews* 2018, 118 (7), 4037-4070.
26. Silverman, R. B., Mechanism-Based Enzyme Inactivators. *Method Enzymol* 1995, 249, 240-283.
27. Rando, R. R., Mechanism-Based Enzyme Inactivators. *Pharmacol Rev* 1984, 36 (2), 111-142.
28. Walsh, C. T., Suicide Substrates, Mechanism Based Enzyme Inactivators—Recent Developments. *Annu Rev Biochem* 1984, 53, 493-535.
29. Juncosa, J. I.; Takaya, K.; Le, H. V.; Moschitto, M. J.; Weerawarna, P. M.; Mascarenhas, R.; Liu, D. L.; Dewey, S. L.; Silverman, R. B., Design and Mechanism of (S)-3-Amino-4-(difluoromethylenyl)cyclopent-1-ene-1-carboxylic Acid, a Highly Potent gamma-Aminobutyric Acid Aminotransferase Inactivator for the Treatment of Addiction. *J Am Chem Soc* 2018, 140 (6), 2151-2164.
30. Pan, Y.; Gerasimov, M. R.; Kvist, T.; Wellendorph, P.; Madsen, K. K.; Pera, E.; Lee, H.; Schousboe, A.; Chebib, M.; Brauner-Osborne, H.; Craft, C. M.; Brodie, J. D.; Schiffer, W. K.; Dewey, S. L.; Miller, S. R.; Silverman, R. B., (1S, 3S)-3-Amino-4-difluoromethylenyl-1-cyclopentanoic Acid (CPP-115), a Potent gamma-Aminobutyric Acid Aminotransferase Inactivator for the Treatment of Cocaine Addiction. *J Med Chem* 2012, 55 (1), 357-366.
31. Sivenius, M. R.; Ylinen, A.; Murros, K.; Matilainen, R.; Riekkinen, P., Double-blind dose reduction study of vigabatrin in complex partial epilepsy. *Epilepsia* 1987, 28 (6), 688-92.
32. Wheless, J. W.; Ramsay, R. E.; Collins, S. D., Vigabatrin. *Neurotherapeutics* 2007, 4 (1), 163-172.
33. Nanavati, S. M.; Silverman, R. B., Mechanisms of Inactivation of Gamma-Aminobutyric-Acid Aminotransferase by the Antiepilepsy Drug Gamma-Vinyl Gaba (Vigabatrin). *J Am Chem Soc* 1991, 113 (24), 9341-9349.
34. Silverman, R., CPP-115: A novel GABA aminotransferase inactivator and potential new treatment for epilepsy, addiction, and hepatocellular carcinoma. *Abstr Pap Am Chem S* 2016, 252.
35. Pan, Y.; Qiu, J.; Silverman, R. B., Design, synthesis, and biological activity of a difluoro-substituted, conformationally rigid vigabatrin analogue as a potent gamma-aminobutyric acid aminotransferase inhibitor. *J Med Chem* 2003, 46 (25), 5292-5293.
36. Lee, H.; Doud, E. H.; Wu, R.; Sanishvili, R.; Juncosa, J. I.; Liu, D. L.; Kelleher, N. L.; Silverman, R. B., Mechanism of Inactivation of gamma-Aminobutyric Acid Aminotransferase by (1S,3S)-3-Amino-4-difluoromethylene-1-cyclopentanoic Acid (CPP-115). *J Am Chem Soc* 2015, 137 (7), 2628-2640.
37. Briggs, S. W.; Mowrey, W.; Hall, C. B.; Galanopoulou, A. S., CPP-115, a vigabatrin analogue, decreases spasms in the multiple-hit rat model of infantile spasms. *Epilepsia* 2014, 55 (1), 94-102.
38. Doumlele, K.; Conway, E.; Hedlund, J.; Tolete, P.; Devinsky, O., A case report on the efficacy of vigabatrin analogue (1S, 3S)-3-amino-4-difluoromethylenyl-1-cyclopentanoic acid (CPP-115) in a patient with infantile spasms. *Epilepsy Behav Case* 2016, 6, 67-69.
39. Lee, H.; Juncosa, J. I.; Silverman, R. B., Ornithine Aminotransferase versus GABA Aminotransferase: Implications for the Design of New Anticancer Drugs. *Med Res Rev* 2015, 35 (2), 286-305.
40. Zhu, W.; Doubleday, P. F.; Catlin, D. S.; Weerawarna, P. M.; Butrin, A.; Shen, S.; Wawrzak, Z.; Kelleher, N. L.; Liu, D.; Silverman, R. B., A Remarkable Difference That One Fluorine Atom Confers on the Mechanisms of Inactivation of Human Ornithine Aminotransferase by Two Cyclohexene Analogues of gamma-Aminobutyric Acid. *J Am Chem Soc* 2020, 142 (10), 4892-4903.
41. Yeung, Y. Y.; Hong, S.; Corey, E. J., A short enantioselective pathway for the synthesis of the anti-influenza neuramidase inhibitor oseltamivir from 1,3-butadiene and acrylic acid. *J Am Chem Soc* 2006, 128 (19), 6310-1.
42. Moschitto, M. J.; Silverman, R. B., Synthesis of (S)-3-Amino-4-(difluoromethylenyl)-cyclopent-1-ene-1-carboxylic Acid (OV329), a Potent Inactivator of gamma-Aminobutyric Acid Aminotransferase. *Org Lett* 2018, 20 (15), 4589-4592.
43. Shen, B. W.; Hennig, M.; Hohenester, E.; Jansonius, J. N.; Schirmer, T., Crystal structure of human recombinant ornithine aminotransferase. *J Mol Biol* 1998, 277 (1), 81-102.
44. Moschitto, M. J.; Doubleday, P. F.; Catlin, D. S.; Kelleher, N. L.; Liu, D. L.; Silverman, R. B., Mechanism of Inactivation of Ornithine Aminotransferase by (1S,3S)-3-Amino-4-(hexafluoropropan-2-ylidenyl)cyclopentane-1-carboxylic Acid. *J Am Chem Soc* 2019, 141 (27), 10711-10721.
45. Mascarenhas, R.; Le, H. V.; Clevenger, K. D.; Lehrer, H. J.; Ringe, D.; Kelleher, N. L.; Silverman, R. B.; Liu, D., Selective Targeting by a Mechanism-Based Inactivator against Pyridoxal 5'-Phosphate-Dependent Enzymes: MechanismS of Inactivation and Alternative Turnover. *Biochemistry-Us* 2017, 56 (37), 4951-4961.
46. Storici, P.; Capitani, G.; Muller, R.; Schirmer, T.; Jansonius, J. N., Crystal structure of human ornithine aminotransferase complexed with the highly specific and potent inhibitor 5-fluoromethylornithine. *J Mol Biol* 1999, 285 (1), 297-309.
47. Shah, S. A.; Shen, B. W.; Brunger, A. T., Human ornithine aminotransferase complexed with L-canaline and gabaculine: structural basis for substrate recognition. *Structure* 1997, 5 (8), 1067-1075.
48. Rando, R. R., Mechanism of Irreversible Inhibition of Gamma-Aminobutyric Acid-Alpha-Ketoglutaric Acid Transaminase by Neurotoxin Gabaculine. *Biochemistry-Us* 1977, 16 (21), 4604-4610.
49. Kobayashi, K.; Miyazawa, S.; Endo, A., Isolation and Inhibitory Activity of Gabaculine, a New Potent Inhibitor of Gamma-Aminobutyrate Aminotransferase Produced by a Streptomyces. *Febs Lett* 1977, 76 (2), 207-210.
50. Zhu, W.; Doubleday, P. F.; Catlin, D. S.; Weerawarna, P. M.; Butrin, A.; Shen, S. D.; Wawrzak, Z.; Kelleher, N. L.;

Liu, D. L.; Silverman, R. B., A Remarkable Difference That One Fluorine Atom Confers on the Mechanisms of Inactivation of Human Ornithine Aminotransferase by Two Cyclohexene Analogues of gamma-Aminobutyric Acid. *J Am Chem Soc* 2020, 142 (10), 4892-4903.

51. Shen, S. D.; Doubleday, P. F.; Weerawarna, P. M.; Zhu, W.; Kelleher, N. L.; Silverman, R. B., Mechanism-Based Design of 3-Amino-4-Halocyclopentenecarboxylic Acids as Inactivators of GABA Aminotransferase. *Acs Med Chem Lett* 2020, 11 (10), 1949-1955.

52. Zubarev, R. A.; Horn, D. M.; Fridriksson, E. K.; Kelleher, N. L.; Kruger, N. A.; Lewis, M. A.; Carpenter, B. K.; McLafferty, F. W., Electron capture dissociation for structural characterization of multiply charged protein cations. *Anal Chem* 2000, 72 (3), 563-73.

53. Liu, F.; Lossl, P.; Scheltema, R.; Viner, R.; Heck, A. J. R., Optimized fragmentation schemes and data analysis strategies for proteome-wide cross-link identification. *Nat Commun* 2017, 8, 15473.

54. Olsen, J. V.; Macek, B.; Lange, O.; Makarov, A.; Horning, S.; Mann, M., Higher-energy C-trap dissociation for peptide modification analysis. *Nat Methods* 2007, 4 (9), 709-12.

55. DeHart, C. J.; Fellers, R. T.; Fornelli, L.; Kelleher, N. L.; Thomas, P. M., Bioinformatics Analysis of Top-Down Mass Spectrometry Data with ProSight Lite. *Methods Mol Biol* 2017, 1558, 381-394.

56. Skinner, O. S.; Haverland, N. A.; Fornelli, L.; Melani, R. D.; Do Vale, L. H. F.; Seckler, H. S.; Doubleday, P. F.; Schachner, L. F.; Srzentic, K.; Kelleher, N. L.; Compton, P. D., Top-down characterization of endogenous protein complexes with native proteomics. *Nat Chem Biol* 2018, 14 (1), 36-41.

57. Layer, R. W., The Chemistry of Imines. *Chem Rev* 1963, 63 (5), 489-510.

58. Johnson, J. E.; Morales, N. M.; Gorczyca, A. M.; Dolliver, D. D.; McAllister, M. A., Mechanisms of acid-catalyzed Z/E isomerization of imines. *J Org Chem* 2001, 66 (24), 7979-7985.

59. Galvez, J.; Guirado, A., A theoretical study of topomerization of imine systems: inversion, rotation or mixed mechanisms? *J Comput Chem* 2010, 31 (3), 520-31.

60. Traven', V. F.; Ivanov, I. V.; Panov, A. V.; Safronova, O. B.; Chibisova, T. A., Solvent-induced E/Z(C═N)-isomerization of imines of some hydroxy-substituted formylcoumarins. *Russian Chemical Bulletin* 2008, 57 (9), 1989-1995.

61. Butrin, A.; Beaupre, B. A.; Kadamandla, N.; Zhao, P.; Shen, S.; Silverman, R. B.; Moran, G. R.; Liu, D., Structural and Kinetic Analyses Reveal the Dual Inhibition Modes of Ornithine Aminotransferase (1S,3S)-3-Amino-4-(hexafluoropropan-2-ylidenyl)-cyclopentane-1-carboxylic Acid (BCF3). *Acs Chem Biol* 2021, 16 (1), 67-75.

Example 2—Supplemental Material for Example 1

Scheme 7. Proposed inactivation mechanism for Gabaculine.

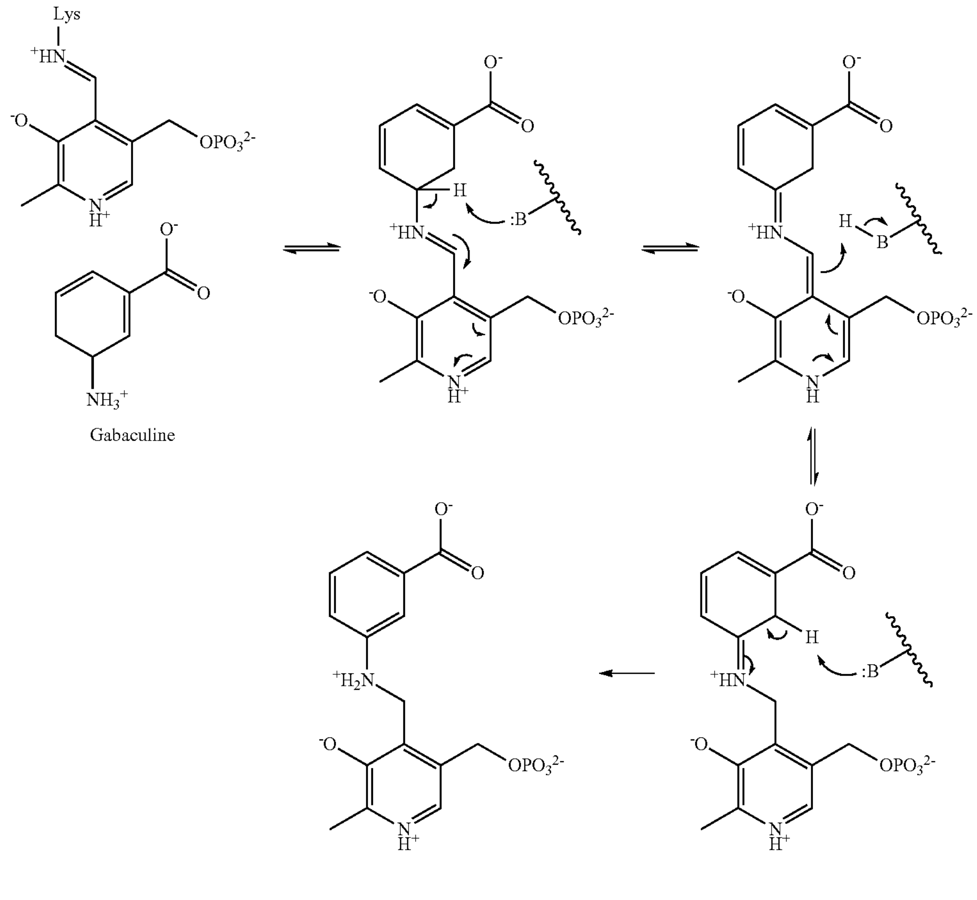

Gabaculine

Scheme 8. Possible mechanisms for the formation of final adduct 28¢.
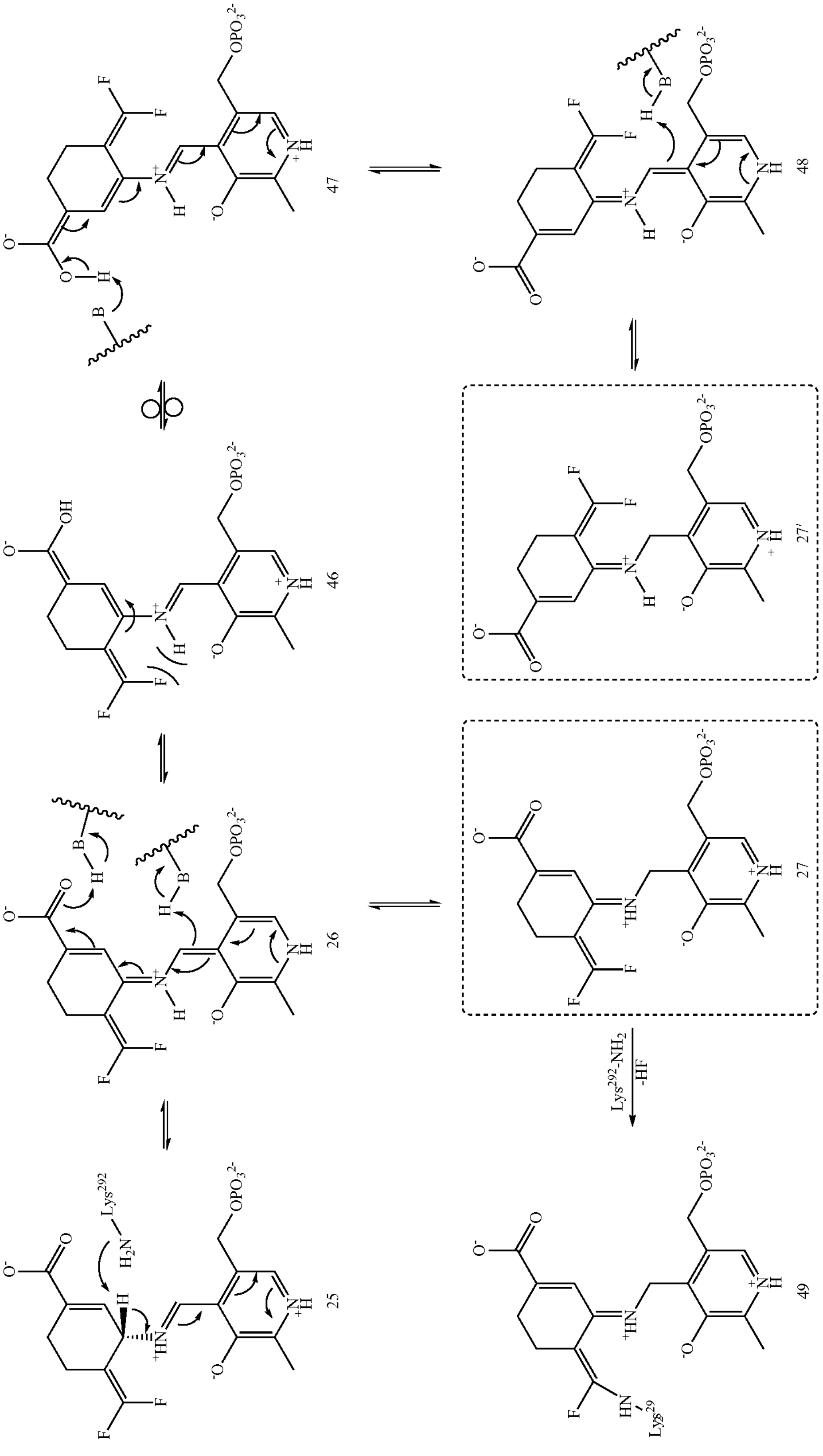
25 26 46 47 48 27' 27 49

-continued
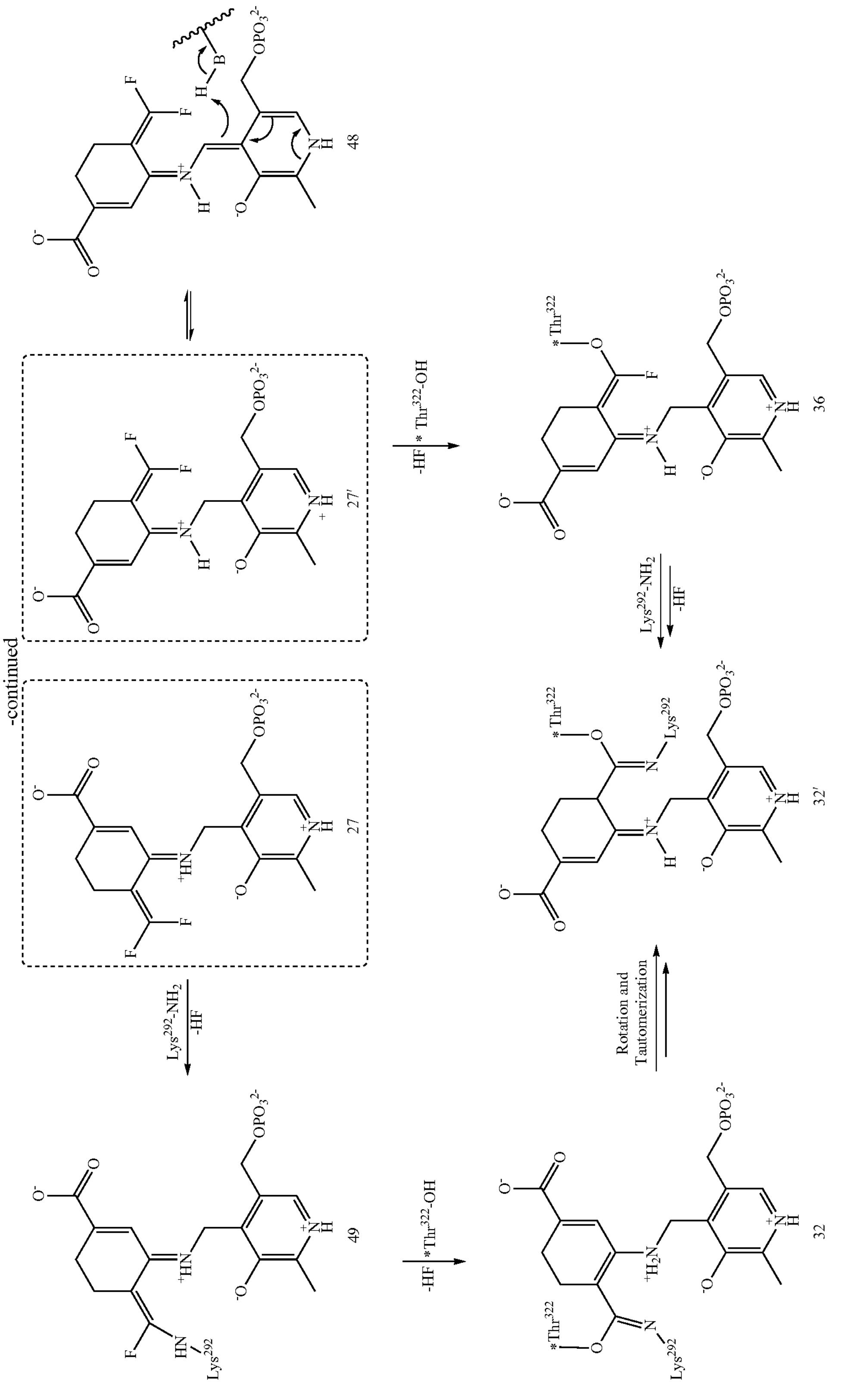
48
27'
27
36
32'
49
32

Synthesis of Inactivators 12-15

General Synthetic Methods. All chemicals were purchased from Sigma Aldrich, Acros Organics, or Combi-block and used without further purification. Anhydrous solvents (THF, $CH_3CN$, DMF) were purified before use by passing through a column composed of activated alumina and a supported copper redox catalyst. Yields refer to chromatographically homogeneous materials. Analytical thin-layer chromatography (TLC) was performed using Merck Silica Gel 60 Å F-254 precoated plates (0.25 mm thickness), and components were visualized by ultraviolet light (254 nm) and/or ceric ammonium molybdate stain and/or ninhydrin stain. Flash column chromatography was performed on a Teledyne Combiflash Rf Plus automated flash purification system with various Taledyne cartridges (4-80 g, 40-63 μm, 60 Å). Purifications were performed with hexanes and ethyl acetate unless otherwise noted. $^1H$ and $^{13}C$ NMR spectra were recorded on a Bruker Avance-III NMR spectrometer at 500 MHz and 126 MHz, respectively, in CDC13, $CD_3OD$ or DMSO-$d_6$. Chemical shifts were reported in ppm; multiplicities are indicated by s=singlet, brs=broad singlet, d=doublet, t=triplet, q=quartet, dd=doublet of doublet, dt=doublet of triplet, dq=doublet of quartet, m=multiplet resonance. Coupling constants 'J' were reported in Hz. High-resolution mass spectral data were obtained on an Agilent 6210 LC-TOF spectrometer in the positive ion mode using electrospray ionization with an Agilent G1312A HPLC pump and an Agilent G1367B autoinjector at the Integrated Molecular Structure Education and Research Center (IMSERC), Northwestern University. Analytical HPLC was performed using a reversed-phase Agilent Infinity 1260 HPLC with a Phenomenex Kintex C-18 column (50×2.1 mm, 2.6 μm), detecting with UV absorbance at 254 nm.

(1R,4S)-2-azabicyclo[2.2.2]octane-3,6-dione (17a) & (1S,5S)-6-azabicyclo[3.2.1]octane-4,7-dione (17b). To a stirred solution of solution of the lactam 16[1] (3.79 g, 15.1 mmol, 1.0 equiv) in nitromethane (40 mL) was added silver(I) trifluoroacetate (5.00 g, 22.6 mmol, 1.5 equiv) at 0° C. (the flask was wrapped with aluminum foil). The reaction was warmed to r.t. and stirred for 16 h. The reaction was diluted with Et2O and filtered through a pad of Celite. The filtrate was concentrated in vacuo, followed by the addition of ammonia solution (7 N in methanol, 29 mL). After the reaction was stirred at r.t. for 1 h, it was filtered through a cotton plug and the obtained filtrate was concentrated in vacuo. To a solution of the obtained crude in dry $CH_3CN$ (60 mL) was added $NaHCO_3$ (6.34 g, 75.5 mmol, 5.0 equiv) and Dess-Martin periodinane (7.68 g, 18.1 mmol, 1.2 equiv). After the suspension was stirred at r.t. for 1 h, it was diluted with EtOAc and then filtered. The filtrate was concentrated and purified by silica gel chromatography (15% to 45% EtOAc in hexane) to afford a white solid (17a, 420 mg, 20%) $^1H$ NMR (500 MHz, $CDCl_3$): δ 7.80-7.60 (brs, N—H, 1H), 3.77 (ddd, J=5.3, 4.2, 1.6 Hz, H1, 1H), 2.86-2.82 (m, H4, 1H), 2.58 (ddd, J=19.0, 2.8, 2.8 Hz, 1H), 2.33 (dd, J=19.0, 2.8 Hz, 1H), 2.16-1.78 (m, 4H); $^{13}C$ NMR (126 MHz, $CDCl_3$): δ=206.5, 176.5, 58.6, 39.7, 39.1, 25.3, 22.3; HRMS-ESI (m/z) $[M+H]^+$ calc'd for $C_7H_{10}NO_2$=140.0706, found=140.0711. and a white solid (17b, 420 mg, 20%). $^1H$ NMR (500 MHz, $CDCl_3$): δ 7.10-6.80 (brs, 1H), 3.78 (dd, J=6.0, 1.0 Hz, 1H), 2.80 (ddd, J=16.7, 11.05, 9.6 Hz, 1H), 2.67 (dddd, J=12.1, 6.1, 5.6, 3.1 Hz, 1H), 2.61-2.57 (m, H1, 1H), 2.43 (ddd, J=16.7, 7.2, 7.2 Hz, H3/H3', 1H), 2.21 (dddd, J=13.5, 9.5, 3.1, 3.1 Hz, 1H), 2.02-1.93 (m, 1H), 1.89 (dddd, J=13.5, 7.4, 7.2, 3.1 Hz, 1H); $^{13}C$ NMR (126 MHz, $CDCl_3$): δ=207.8, 179.5, 61.8, 39.2, 37.5, 34.4, 25.4.

(1S,5S)-6-(4-methoxybenzyl)-6-azabicyclo[3.2.1]octane-4,7-dione (18). To a stirred solution of 17 (19.1 mg, 0.137 mmol, 1.0 equiv) in DMF (0.14 mL) at 0° C. was added sodium hydride (60 wt. % dispersion in mineral oil, 6.6 mg, 0.165 mmol, 1.2 equiv). After 1 h, p-methoxybenzyl chloride (20.1 μL, 0.151 mmol, 1.1 equiv) was added via syringe. The reaction mixture was stirred for 16 h before quenching with a 1:1 saturated solution of aq. sodium bicarbonate and water. The solution was partitioned with a 1:1 mixture of ethyl acetate and hexanes. The organic layer was removed, and the aqueous layer was further extracted with the ethyl acetate hexanes mixture (7×). The combined organic layer was concentrated in vacuo and purified by silica gel chromatography (10% to 100% EtOAc in hexane) to afford a colorless oil (18, 23.5 mg, 66%). $^1H$ NMR (500 MHz, $CDCl_3$): δ 7.18 (d, J=8.6 Hz, 2H), 6.83 (d, J=8.6 Hz, 2H), 4.56 (d, J=14.6 Hz, 1H), 4.17 (d, J=14.6 Hz, 1H), 3.78 (s, 3H), 3.65 (d, J=5.9 Hz, 1H), 2.73-2.68 (m, 1H), 2.53 (dddd, J=11.5, 6.0, 5.4, 2.9 Hz, 1H), 2.40-2.20 (m, 3H), 1.91-1.82 (m, 2H). $^{13}C$ NMR (126 MHz, $CDCl_3$): δ 207.5, 176.2, 159.4, 130.2, 127.6, 114.2, 65.5, 55.3, 53.4, 45.2, 39.9, 35.6, 34.6, 26.4. HRMS-ESI (m/z) $[M+Na]^+$ calc'd for $C_{15}H_{17}NNaO_3$: 282.1101, found: 282.1100.

(1S,5S)-4-(difluoromethylene)-6-(4-methoxybenzyl)-6-azabicyclo[3.2.1]octan-7-one (19). To a stirred solution of diethyl (difluoromethyl)phosphonate (128 mg, 0.678 mmol, 1.2 equiv) in THF (12 mL) at −100° C. was added 1-Butyllithium (1.7 M in pentanes, 0.38 mL, 0.649 mmol, 1.1 equiv). After 10 min, a solution of 18 (153 mg, 0.590 mmol, 1.0 equiv) in THF (2 mL) was added rapidly via syringe. The reaction mixture was stirred 2 h before being warm to r.t. The reaction was heated and refluxed for 16 h. The reaction was cooled to r.t. and quenched with aqueous $NH_4Cl$ solution. The solution was partitioned with diethyl ether, and the aqueous layer was separated and further extracted with $Et_2O$ (4×). The combined organic layer was concentrated in vacuo and purified by silica gel chromatography (50% EtOAc in hexane) to afford a colorless oil (19, 95 mg, 55%). $^1H$ NMR (500 MHz, $CDCl_3$): δ 7.18 (d, J=8.5 Hz, 2H), 6.86 (d, J=8.5 Hz, 2H), 4.76 (d, J=14.6 Hz, 1H), 4.10 (dd, J=3.8, 3.4 Hz, 1H), 3.80 (d, J=14.6 Hz, 1H), 3.80 (s, 3H), 2.65-2.60 (m, 1H), 2.38 (d, J=15.6, 6.6 Hz, 1H), 2.26-2.20 (m, 1H), 2.05-1.97 (m, 1H), 1.97-1.85 (m, 1H), 1.66-1.58 (m, 1H), 1.61 (d, J=11.3 Hz, 1H). $^{13}C$ NMR (126 MHz, $CDCl_3$): δ=176.5, 159.2, 151.1 (dd, J=287.2, 284.4 Hz), 129.7, 128.3, 114.0, 85.2 (dd, J=17.8, 17.8 Hz), 55.3, 53.2 (dd, J=4.5, 1.6 Hz), 43.8, 40.4, 36.6 (d, J=2.3 Hz), 25.0, 17.7. HRMS-ESI (m/z) $[M+H]^+$ calc'd for $C_{16}H_{18}F_2NO_2$: 294.1300, found: 294.1295.

(1S,5S)-4-(difluoromethylene)-6-azabicyclo[3.2.1]octan-7-one (20). To a stirred solution of lactam 19 (68.0 mg, 0.232 mmol, 1.0 equiv) in acetonitrile (2.32 mL) was added a solution of cerium (IV) ammonium nitrate (318.0 mg, 0.580 mmol, 2.5 equiv) in water (0.23 mL) at 0° C. (the flask was wrapped with aluminum foil). The reaction was warmed to r.t. and stirred for 10 h. The solution was partitioned with EtOAc and the aqueous layer was further extracted with EtOAc (4×). The combined organic solution was concentrated in vacuo and purified by silica gel chromatography (40% EtOAc in hexane to 100% EtOAc) to afford a white solid (20, 32 mg, 80%). $^1H$ NMR (500 MHz, $CDCl_3$): δ 6.40-6.00 (brs, 1H), 4.39-4.35 (m, 1H), 2.53-2.47 (m, 1H), 2.48-2.32 (m, 2H), 2.30-2.18 (m, 1H), 2.00-1.90 (m, 1H), 1.70 (d, J=11.0 Hz, 1H), 1.68-1.56 (m, 1H). $^{13}C$ NMR (126 MHz, $CDCl_3$): δ 180.1, 150.1 (dd, J=286.3, 283.8 Hz), 87.0

(dd, J=18.0, 18.0 Hz), 50.2 (dd, 4.6, 1.4 Hz), 39.9, 38.8, 24.6, 17.7. HRMS-ESI (m/z) $[M+H]^+$ calc'd for $C_8H_{10}F_2NO$: 174.0725, found: 174.0724.

(1S,3S)-3-amino-4-(difluoromethylene)cyclohexane-1-carboxylic acid (12). A suspension of lactam 20 (31.0 mg, 0.179 mmol, 1.0 equiv) in aqueous HCl (4N, 5 mL) was heated to 75° C. and stirred for 5 h. The reaction mixture was concentrated to dryness in vacuo. The white solid was redissolved in a small quantity of water and the mixture was once again concentrated to dryness. The crude residue was concentrated and purified by C-18 chromatography (0-10% $CH_3CN$ in $H_2O$) to give a white solid (20, 33.0 mg, 96%). $^1H$ NMR (500 MHz, $D_2O$): δ 4.16 (dd, J=5.5, 1.4 Hz, 1H), 2.78-2.70 (m, 1H), 2.30-2.20 (m, 2H), 2.12-1.94 (m, 2H), 1.90-1.80 (m, 2H); $^{13}C$ NMR (126 MHz, $D_2O$): δ=182.4, 151.8 (dd, J=286.0, 286.0 Hz), 85.5 (dd, J=23.1, 13.6 Hz), 44.3 (d, J=4.0 Hz), 41.2, 30.2, 27.4, 18.9; HRMS-ESI (m/z) $[M+H]^+$ calc'd for $C_8H_{12}F_2NO_2$: 192.0831, found: 192.0830.

Ethyl (1R,3S)-3-((tert-butoxycarbonyl)amino)-4-(difluoromethylene)cyclohexane-1-carboxylate (22). To a stirred solution of 21[2] (2.9 g, 10.16 mmol, 1.0 equiv) and $2\text{-PySO}_2CF_2H$ (2.36 g, 12.20 mmol, 1.2 equiv) in dry DMF (20 mL) at −60° C. under Ar was added a solution of $^t$BuOK (2.05 g, 18.29 mmol, 1.8 equiv) in dry DMF (20 mL) dropwise over 1 h. The solution was slowly warmed to −40° C. after the addition. A solution of $NH_4Cl$ (sat., 10 mL) was then added slowly, followed by the addition of HCl (3 M, 10 mL). The reaction was slowly warmed to r.t. and stirred overnight. The solution was diluted with EtOAc (150 mL). The organic phase was separated, washed with water (50 mL) and brine (50 mL), and dried with anhydrous $Na_2SO_4$. The solution was concentrated and purified by silica gel chromatography (30% EtOAc in hexane) to afford a yellow oil (22, 2.5 g, 77%). $^1H$ NMR (500 MHz, $CDCl_3$) δ 4.76 (brs, 1H), 4.54 (brs, 1H), 4.09 (q, J=7.1 Hz, 2H), 2.60 (brs, 1H), 2.40 (d, J=14.3 Hz, 1H), 2.14 (d, J=12.9 Hz, 1H), 2.07-1.90 (m, 2H), 1.64 (td, J=13.4, 3.9 Hz, 1H), 1.41 (s, 10H), 1.21 (t, J=7.1 Hz, 3H). HRMS-ESI (m/z) $[M+Na]^+$ calc'd for $C_{15}H_{23}F_2NNa$: 3452.1487, found: 342.1473.

(1R,5S)-4-(Difluoromethylene)-1-(phenylselanyl)-6-azabicyclo[3.2.1]octan-7-one (23). To a stirred solution of KHMDS (IM in THF, 2.76 mL, 2.76 mmol, 2.2 equiv) was slowly added dry THF (5 mL), and a solution of 22 (400 mg, 1.25 mmol, 1.0 equiv) in dry THF (5 mL) at −78° C. under Ar over 30 minutes. The solution was stirred at −78° C. for an additional 3 h, followed by the addition of a solution of PhSeCl (264 mg, 1.38 mmol, 1.1 equiv) in THF (5 mL). The solution was then slowly warmed to r.t. and stirred overnight. The reaction was quenched with the addition of sat. $NH_4Cl$ (10 mL). The solution was then diluted with EtOAc (100 mL) and the organic phase was separated. The aqueous phase was extracted with EtOAc (50 mL) twice. The combined organic phase was washed with brine (ca. 10 mL) and dried with anhydrous $Na_2SO_4$. The solution was concentrated and purified by silica gel chromatography (50% EtOAc in hexane) to give a colorless oil (23, 236 mg, 57%). $^1H$ NMR (400 MHz, Chloroform-d) δ 7.66 (dd, J=8.1, 1.3 Hz, 2H), 7.39-7.35 (m, 1H), 7.30 (t, J=7.3 Hz, 2H), 6.45 (s, 1H), 4.30 (brs, 1H), 2.56-2.45 (m, 2H), 2.37-2.24 (m, 1H), 2.20-2.12 (m, 1H), 1.80 (dd, J=12.3, 7.0 Hz, 1H), 1.75 (d, J=9.9 Hz, 1H). HRMS-ESI (m/z) $[M+Na]^+$ calc'd for $C_9H_{12}F_3N_4OSe$: 352.0023, found: 352.0018.

Ethyl (S)-3-((tert-butoxycarbonyl)amino)-4-(difluoromethylene)cyclohex-1-ene-1-carboxylate (24a) & Ethyl (S)-5-((tert-butoxycarbonyl)amino)-4-(difluoro methylene)cyclohex-1-ene-1-carboxylate (24b). To a stirred solution of 23 (150 mg, 0.866 mmol, 1.0 equiv) in DCM (10 mL) was added BoczO (283 mg, 1.3 mmol, 1.5 equiv), DIPEA (0.22 mL, 1.3 mmol, 1.5 equiv) and DMAP (11 mg, 0.086 mmol, 0.1 equiv) sequentially. The solution was stirred at r.t. overnight. The completion of reaction was determined by TLC (hexane: EtOAc=2:1). The solution was concentrated and diluted with EtOH (5 mL), followed by the addition of $K_2CO_3$ (360 mg, 2.6 mmol, 3.0 equiv). The suspension was stirred at r.t. for 3 h. The mixture was concentrated and diluted with DCM (20 mL) and HCl (0.5 M, 10 mL). The organic phase was separated and then washed with water (10 mL), $NaHCO_3$ (aq. 10 mL), and brine (10 mL). The organic phase was dried over anhydrous $Na_2SO_4$. To this stirred solution was added m-CPBA (291 mg, 1.3 mmol, 1.5 equiv). The solution was stirred at r.t. for 3 h. The completion of reaction was determined by LC-MS. The reaction was quenched with sat. $Na_2S_2O_3$ (aq. 10 mL). The organic phase was separated, washed with saturated $NaHCO_3$ (aq. 10 mL) and brine (10 mL), and dried with anhydrous $Na_2SO_4$. The solution was concentrated and purified by silica gel chromatography (5-10% EtOAc in hexane) to afford a colorless oil (24a, 35 mg, 24%) $^1H$ NMR (500 MHz, $CDCl_3$) δ 6.86-6.82 (m, 1H), 4.98 (brs, 1H), 4.66 (brs, 1H), 4.21 (qd, J=7.1, 2.1 Hz, 2H), 2.61-2.49 (m, 2H), 2.18 (dddd, J=19.1, 10.3, 5.1, 2.3 Hz, 1H), 1.99 (ddtd, J=14.4, 11.8, 5.6, 3.3 Hz, 1H), 1.45 (s, 9H), 1.29 (t, J=7.1 Hz, 3H). $^{13}C$ NMR (126 MHz, $CDCl_3$) δ 166.6, 154.6, 152.7 (t, J=286.9 Hz), 135.5, 133.4, 86.4, 80.3, 61.0, 42.9, 28.5, 24.4, 18.2, 14.3. HRMS-APCI (m/z) $[M-H]^-$ calc'd for $C_{15}H_{21}F_2NO_4$: 316.1366, found: 316.1361. and a colorless oil (24b, 32 mg, 22%). $^1H$ NMR (500 MHz, $CDCl_3$) δ 6.97 (brs, 1H), 4.70 (brs, 1H), 4.62 (brs, 1H), 4.20 (q, J=7.1 Hz, 2H), 3.02 (d, J=21.7 Hz, 1H), 2.90 (d, J=21.9 Hz, 1H), 2.65 (d, J=17.8 Hz, 1H), 2.49 (d, J=17.6 Hz, 1H), 1.43 (s, 9H), 1.29 (t, J=7.1 Hz, 3H). $^{13}C$ NMR (126 MHz, $CDCl_3$) δ 166.5, 155.1, 151.6 (t, J=286.2 Hz), 136.2, 127.8, 84.2, 80.0, 61.0, 42.4, 30.8, 28.5, 21.9, 14.4. HRMS-APCI (m/z) $[M-H]^-$ calc'd for $C_{15}H_{20}F_2NO_4$: 316.1366, found: 316.1361.

General procedure A. To a solution of aq. HCl (4 M, 1.5 mL) and AcOH (1.5 mL) was added the ester intermediate under Ar. The solution was sealed and heated to 80° C. and stirred overnight. The completion of reaction was determined by LC-MS. The solution was concentrated and purified by C-18 chromatography (0-10% $CH_3CN$ in $H_2O$) to give product.

(1R,3S)-3-Amino-4-(difluoromethylene)cyclohexane-1-carboxylic acid (13). 22 (200 mg, 0.626 mmol) was deprotected by procedure A to give a white solid (13, 87 mg, 61%). $^1H$ NMR (500 MHz, $CD_3OD$) δ 4.37 (brs, 1H), 2.75 (tt, J=12.3, 3.5 Hz, 1H), 2.59-2.51 (m, 1H), 2.27 (d, J=14.8 Hz, 1H), 2.24-2.14 (m, 2H), 1.91 (ddd, J=14.9, 13.1, 4.6 Hz, 1H), 1.50 (qd, J=13.3, 12.7, 4.4 Hz, 1H). $^{13}C$ NMR (126 MHz, $CD_3OD$) δ 175.6, 152.8 (t, J=287.9 Hz), 84.3 (dd, J=23.2, 15.4 Hz), 44.3 (dd, J=5.3, 1.2 Hz), 36.2, 31.1, 27.3, 18.6. HRMS-ESI (m/z) $[M-H]^-$ calc'd for $C_8H_{10}F_2NO_2$: 190.0685, found: 190.0684.

(S)-3-Amino-4-(difluoromethylene)cyclohex-1-ene-1-carboxylic acid (14). 24a (30 mg, 0.095 mmol) was deprotected by procedure A to give a white solid (14, 11 mg, 52%). $^1H$ NMR (500 MHz, $CD_3OD$) δ 6.89 (brs, 1H), 4.72 (brs, 1H), 2.71 (d, J=14.4 Hz, 1H), 2.65 (d, J=8.9 Hz, 1H), 2.32-2.17 (m, 2H). $^{13}C$ NMR (126 MHz, $CD_3OD$) δ 168.7, δ 155.0 (t, J=287.6 Hz), 139.2, 130.5, 84.7 (dd, J=24.6, 15.5 Hz), 44.2 (d, J=5.8 Hz), 25.0, 17.8. HRMS-ESI (m/z) $[M-H]^-$ calc'd for $C_8H_8F_2NO_2$: 188.0529, found: 188.0534.

(S)-5-Amino-4-(difluoromethylene)cyclohex-1-ene-1-carboxylic acid (15). 24b (25 mg, 0.095 mmol) was deprotected by procedure A to give a white solid (15, 15 mg, 67%). 1H NMR (500 MHz, $CD_3OD$) δ 7.1 (brs, 1H), 4.5 (brs, 1H), 3.2 (d, J=22.3 Hz, 1H), 3.1-3.0 (m, 1H), 2.9 (d, J=18.7 Hz, 1H), 2.6 (ddq, J=18.4, 6.0, 3.1 Hz, 1H). $^{13}C$ NMR (126 MHz, $CD_3OD$) δ 168.8, 154.2 (t, J=288.4 Hz), 137.0 (d, J=1.8 Hz), 126.9, 82.7 (dd, J=23.1, 17.6 Hz), 44.1 (d, J=6.2 Hz), 28.9, 21.8. HRMS-ESI (m/z) $[M-H]^-$ calc'd for $C_8H_8F_2NO_2$: 188.0529, found: 188.0534.

Enzyme Assays.

hOAT and PYCR1 were expressed, grown, and purified according to literature procedures.[3-4] GABA-AT was isolated from pig brains and purified according to a literature procedure.[5] Coupled enzyme assays for GABA-AT, hOAT, Ala-AT, and Asp-AT were carried out according to previous procedures.[6-7]

Dialysis Assay.

The dialysis experiment was conducted using previous protocols.[6, 8-9]

Partition Ratio Experiment.

The partition ratio was calculated using previous protocols.[6, 8-9]

Fluoride Ion Release.

The fluoride ion release assay was conducted using previous protocols.[2] The final concentration of hOAT in the sample was determined to be 61.7±4.1 ug/mL (monomer, 1.34±0.12 μM) via BSA assay and calculation of dilution. A calibration curve of voltage (V, mV) was generated from varying concentrations of NaF (F, μM) to get the equation: $F^-=10^\wedge((V-181.4)/-54.21)$. For accurate detection of fluoride ion concentration, 2.0 μM of fluoride ion was added to each control and sample. The number of fluoride ions released per active site was calculated by the ratio of the fluoride ion release concentration and hOAT concentration.

TABLE 4

Calculation of fluoride ion release for 14 with/without the presence of α-KG.

| With α-KG | Control Trial 1 | Control Trial 2 | Control Trial 3 | Sample Trial 1 | Sample Trial 2 | Sample Trial 3 |
|---|---|---|---|---|---|---|
| Test-1 (mV) | 166.0 | 166.2 | 166.0 | 139.8 | 139.9 | 139.3 |
| Test-2 (mV) | 166.1 | 166.2 | 166.3 | 139.8 | 140.1 | 139.5 |
| Test-3 (mV) | 166.0 | 166.3 | 166.2 | 139.6 | 139.9 | 139.3 |
| Ave(mV) | 163.03 | 163.23 | 165.2 | 139.7 | 140.0 | 139.6 |
| $F^-$ Detected (μM) | 1.92 | 1.90 | 1.91 | 5.57 | 5.81 | 5.91 |
| $F^-$ Detected Ave (μM) | Control: 1.91 ± 0.007 | | | Sample: 5.86 ± 0.041 | | |
| $F^-$ Release (μM) | 3.95 | | | | | |
| Enzyme Concentration | 1.34 ± 0.09 μM (Monomer) | | | | | |
| Fluoride ions released per active site (with α-KG) | 2.95 equiv | | | | | |

| Without α-KG | Control Trial 1 | Control Trial 2 | Control Trial 3 | Sample Trial 1 | Sample Trial 2 | Sample Trial 3 |
|---|---|---|---|---|---|---|
| Test-1 (mV) | 166.3 | 166.3 | 166.0 | 141.4 | 142.0 | 141.3 |
| Test-2 (mV) | 166.2 | 166.3 | 166.0 | 141.0 | 141.9 | 141.1 |
| Test-3 (mV) | 166.2 | 166.0 | 165.7 | 141.0 | 141.7 | 140.9 |
| Ave(mV) | 166.2 | 166.2 | 165.9 | 141.1 | 141.9 | 141.1 |
| $F^-$ Detected (μM) | 1.90 | 1.91 | 1.93 | 5.53 | 5.36 | 5.53 |
| $F^-$ Detected Ave (μM) | Control: 1.91 ± 0.012 | | | Sample: 5.48 ± 0.082 | | |
| $F^-$ Release (μM) | 3.57 | | | | | |
| Enzyme Concentration | 1.34 ± 0.09 μM (Monomer) | | | | | |
| Fluoride ions released per active site (without α-KG) | 2.66 equiv | | | | | |

Crystallography

Co-crystallization of hOAT with 14 and 9: The freshly prepared enzyme was buffer exchanged into 50 mM Tricine pH 7.8 and concentrated to a protein concentration of 6 mg/mL. Previously reported crystallization condition[8] was optimized using the hanging drop vapor diffusion method by varying PEG 6000 (8-12%), NaCl (100-250 mM), glycerol (0%-10%) with 100 mM Tricine pH 7.8 was kept constant as the buffer. For each hanging drop, 2 μl of protein solution was mixed with equal volume of well solution and 0.5 μl of 10 mM compound 181 or OV215. The crystals with the best morphology and size grew in a final condition containing 12% PEG 8000, 200 mM NaCl, 10% glycerol. Crystals were transferred to a cryo-protectant solution (well solution supplemented with 30% glycerol) before being flash-frozen in liquid nitrogen.

Crystal Soaking of hOAT with 14: The holoenzyme crystals were first grown via a hanging drop vapor diffusion method. Each drop contained 2 μL of protein and 2 μL of well solution. The best crystallization condition contained 8% PEG 6000, 100 mM NaCl, 5% glycerol, and 50 mM Tricine pH 7.8. Once the holoenzyme crystals reached their maximum size within five days, 1 μL of 10 mM 14 was added to the drop with crystals. Within the first three minutes of 14 addition, the hOAT crystals turned their color from yellow to transparent. The crystals were soaked for varying time periods from 17 to 44 minutes, transferred into cryo-protective solution (well solution supplemented with 30% glycerol), and then flash-frozen in liquid nitrogen.

X-ray Diffraction and Data Processing: Monochromatic X-ray diffraction data were collected at the LS-CAT beamline 21-ID-D at the Advanced Photon Source at Argonne National Laboratory. Data were collected at a wavelength of 1.127 Å and a temperature of 100 K using a Dectris Eiger 9M detector. Data sets were processed and analyzed with with Xia2 software.[10-12]

Model Building and Refinement: The hOAT structure was solved by molecular replacement using PHASER[13] in Phenix. The starting search model was the previously published structure of hOAT[14] (PDB code: 1OAT). The model building and refinement were accomplished in Coot[15] and Phenix[16], respectively, as an iterative process until the lowest possible $R_{free}$/R factor values were attained. Structural depiction figures were prepared using UCSF Chimera[17].

window with a target AGC value of 1e6 charges and subjected to a fixed ETD reaction time of 10 ms with at targeted t-SIM-MS2 method. Given the limits instrument control software, the precursor charge was set to +24. ETD reagent target was set to 7e5 charges. Fragmentation data was collected from 350-2000 m/z in the Orbitrap at a resolution of 120,000 (at 200 m/z) with 4 microscans. Fragmentation spectra were summed across the elution peak of hOAT to increase the signal-to-noise of fragment ions. hOAT was also fragmented using higher energy collisional activation (HCD) on an Orbitrap Eclipse (Thermo Fischer Scientific) mass spectrometer. Protein was introduced to the

TABLE 5

Statistics of the crystal structure of hOAT inactivated by compound 9 and 14.

| Complex | hOAT-14 soaking | hOAT-14 cocrystal | hOAT-9 cocrystal |
|---|---|---|---|
| PDB code | 7LOM | 7LON | 7LNM |
| Space group | P $3_2$ 2 1 | P $3_1$ 1 2 | P $3_2$ |
| Cell dimension | | | |
| α, β, γ (deg) | 90, 90, 120 | 90, 90, 120 | 90, 90, 120 |
| a, b, c (Å) | 115.6, 115.6, 186.5 | 192.0, 192.0, 57.0 | 115.7, 115.7, 188.0 |
| Processed Resolution (Å) | 2.10 | 1.95 | 2.00 |
| Rmerge [a] (%) | 15.0 (192.1) | 17.4 (159.9) | 11.8 (108.6) |
| Rpim [c] (%) | 8.9 (115.2) | 9.2 (92.5) | 6.8 (67.8) |
| I/σ (I) | 7.3 (0.9) | 4.2 (0.8) | 4.6 (1.3) |
| CC ½ [d] (%) | 99.5 (35.6) | 99.7 (74.5) | 99.3 (37.6) |
| Completeness (%) | 98.4 (99.8) | 99.5 (93.0) | 100.0 (100.0) |
| Multiplicity | 7.0 (7.1) | 8.5 (7.0) | 3.9 (3.5) |
| No. Reflections | 579510 | 746626 | 749788 |
| No. Unique Reflections | 83376 | 87426 | 190270 |
| Refinement | | | |
| Rwork[e]/Rfree[f] (%) | 19.96/23.51 | 23.65/27.31 | 15.77/18.59 |
| No. of Atoms | | | |
| protein | 9432 | 9409 | 18907 |
| ligand | 118 | 126 | 246 |
| water | 470 | 574 | 1690 |
| B factors ($Å^2$) | | | |
| protein | 52.49 | 39.24 | 40.55 |
| RMSD [g] | | | |
| bond lengths (Å) | 0.002 | 0.017 | 0.003 |
| bond angles (deg) | 0.56 | 1.58 | 0.60 |
| Ramachandran plot (%) | | | |
| favored | 95.88 | 95.60 | 96.63 |
| allowed | 4.04 | 4.23 | 3.37 |
| outliers | 0.08 | 0.17 | 0.00 |

[a] $R_{merge} = \Sigma|I_{obs} - I_{avg}|/\Sigma I_{avg}$

[b] The values for the highest-resolution bin are in parentheses

[c] Precision-indicating merging R

[d] Pearson correlation coefficient of two "half" data sets

[e] $R_{work} = \Sigma|F_{obs} - F_{calc}|/\Sigma F_{obs}$

[f] Five percent of the reflection data were selected at random as a test set, and only these data were used to calculate $R_{free}$

[g] Root-mean square deviation

Intact Protein Mass Spectrometry and Top-Down Proteomics hOAT was analyzed into a Orbitrap Fusion Lumos or Orbitrap Eclipse (Thermo Fischer Scientific) mass spectrometer and full MS data was acquired as previously described.[8] The liquid chromatography (LC) column heater compartment was set to 55° C. or was left at room temperature (25° C.) as indicated in the results section. hOAT was fragmented using front-end electron transfer dissociation (f-ETD)[18] on an Orbitrap Fusion Lumos (Thermo Fischer Scientific) mass spectrometer. The same LC conditions described[8] were used. The charge state +50 of modified or unmodified hOAT were quadrupole isolated using a 10 m/z mass spectrometer using LC and the same conditions previously described[8] applying a source voltage of 1,700 V and an ion transfer tube temperature of 320° C. HCD data was collected in a data-dependent Top-N modality with cycle time of 2 s, full scan acquired from 600-1800 m/z with 10 microscans and an Orbitrap resolution of 7,500 (at 200 m/z) and a target AGC of 4e6 charges, and a default charge state of +15 using the advanced peak determination algorithm (APD). MS2 data was acquired with a target 5e5 charges and a 3 m/z isolation window with an HCD NCE of 28 and 1 microscan from 300-2000 m/z. Fragmentation data was deconvoluted to neutral mass values using the Xtract algorithm in the Freestyle 1.6 software package (Thermo Fisher)

and analyzed using Prosight Lite software[19] with a 10 ppm fragment mass tolerance and HCD or ETD as the fragmentation method depending on the method used to generate underlying data.

Native Mass Spectrometry

Treated and unmodified control OAT samples were desalted by dialysis against an Amicon 15 kDa molecular weight cutoff filter (Millipore) for 10 times at 4° C. Desalted samples were individually analyzed into a Q-Exactive Ultra High Mass Range (UHMR) (Thermo Fisher Scientific) mass spectrometer using a Nanospray Flex™ static source (Thermo Fisher Scientific) and medium-length borosilicate-coated emitters (Thermo Fisher Scientific). Spray voltages ranged between +1,500V to +2,000V and the ion transfer tube was set to 310° C. The mass spectrometer was acquired in positive ESI mode, with full scan data collected from 4,000-10,000 m/z with 5-20 microscans and an Orbitrap resolution of 35,000 or 17,500 (at 200 m/z). Target AGC of 1e6 charges and maximum injection time ranging from 50-400 ms. The S-lens RF level was set to 200% and extended trapping set to 100. Raw spectra from each experiment were summed across scans and m/z deconvolution was performed using mMass[20] and UniDec[21] to generate zero-charge masses and associated mass standard deviations.

Small Molecule Mass Spectrometry

Metabolomics assays were preformed and data was acquired as previously described.[8] MS1 and MS2 spectra was manually interpreted to identify hOAT metabolite turnover products.

Docking Study

Docking models of ligands bound to GABA-AT or OAT were developed using the Molecular Operating Environment (MOE) computational suite's Builder utility.[22-24] The energy minimization of ligands was conducted in the gas phase using the force field MMFF94X. The X-ray crystal structures of inactivated hOAT (salt bridge maintained, PDB: 1GBN) and inactivated hOAT (salt bridge disrupted, PDB: 7JX9) were uploaded to MOE respectively, followed by the receptor preparation. The tight-binding products in the active pockets were deleted, and catalytic Lys292 was neutralized. The docking sites were specified at the catalytic Lys292 atoms. Ligand dockings were carried out in the prepared aminotransferase enzyme models with unrelated substrates and the solvent atoms inactivated. Ligand placement employed the Alpha Triangle method with Affinity dG scoring generating 300 data points that were further refined using the induced fit method with GBVI/WSA dG scoring to obtain the top 50 docking results. The docking results of each ligand were analyzed for selection of the best docking pose, based on the score and reported X-ray structures.

Molecular Dynamics Simulation

A docking protocol was employed to generate the initial OAT complex corresponding to 14a and 14b for the classical MD simulation. The protein structure chosen for this study was the X-ray crystal structure of xxx (PDB ID: 1OHW) with a resolution of yyy Å. The protonationstates of the amino acid residues were determined using the H++ server. The structures of 14a and 14b were optimized using Gausian09 software at a HF/6-31+(G) level of theory.[15] The inhibitor and protein structures were further refined using AutoDockTools-1.5.6 available with the MGLTools software package.[25] Refined inhibitor structures were docked into the OAT active site using Autodock 4.2 software. A gridbox centered on the active site was generated using Autogrid 4.2 software with a grid spacing of 0.375 Å and dimensions of 55×55×55 points along the x, y, and z axes. Lamarckian genetic algorithm (GA) was used for the conformational search with a GA populationsize of 150 and a maximum number of evaluations of 2,500,000. The 100 generated poses were clustered according to their rmsd values (1.5 Å cutoff), and the lowest energy conformation of the best cluster was selected for the MD simulation. The electrostaticpotential energies (ESP) of the geometrically optimized inhibitors (HF/6-31+G) were calculated at the HF/6-31+G level of theory. Then these energies were used to derive the partial atomic charges of the inhibitors using the electrostatic potential square fit (ESP) method employed in the antechamber module available in the Amber12 program.[26] This is the method used to derive the partialatomic charges of the original Amber forcefields. The inhibitor atoms were treated with general Amber force field (GAFF), and the automatically assigned GAFF atom types were manually adjusted to accurately represent their chemical environment before deriving the parameters. The parameters and topology files were generated using tLEaP and antechamber modules of the Amber12 program. Then these parameters and topology files were converted to GROMACS compatible format using ACPYPE.[27] The forcefield parameters and the topology for covalently bound PLP were derived similarly. The modified Amberff99SB-ILDN forcefield with parameters for covalently bound PLP were used to simulate the protein. Parameters for the OAT dimer were derived using the PDB2gmx module available in the GROMACS 5.1.2 software package. All of the MD simulations were performed using GROMACS 5.1.2 software.[28] The TIP3P model was used as the water model. The protein-inhibitor complex was immersed in a dodecahedron box filled with TIP3P water where the boundaries are extending at least 1.8 nm in all directions from the edges of the protein. Then, NaCl was added to the system up to a concentration of 0.15 M (physiological NaCl concentration) to neutralize the charge of the system. The solvated system was energy minimized with the steepest descent followed by the conjugate gradient method until it converged with a maximum force no greater than 500 KJ $mol^{-1}$ $nm^{-1}$.

The resulting energy minimized periodic system was the starting configuration for the MD simulation, which was carred out with the aid of the Extreme Science and Engineering Discovery Environment (XSEDE).[29] Prior to the production MD simulation, the system was subjected to equilibration in two steps. First, it was equilibrated at constant NVT (number of particles, volume, and temperature) ensemble for 1 ns. Then the resulting system was equilibrated at constant NPT(number of particles, pressure, and temperature) ensemble for 3 ns. Temperature and pressure were controlled at 310 K and 1 bar by the V-rescale thermostat (time constant of 0.4 ps) and the Parrinello-Rahmanbarostat (time constant of 2 ps), respectively. In both of the equilibration steps positions of the heavy atoms were restrained by applying a force constant of 1000 KJ $mol^{-1}$ $nm^{-2}$. After that, the position restraints were gradually reduced from 500 to 100 KJ $mol^{-1}$ $nm^{-2}$ over two runs (1 ns each). Finally, a production MD simulation of the equilibrated system was carried out under the NPT condition for 15 ns (time step of 2 fs) without positional restraints. During the NPTequilibration, the V-rescale thermostat was replaced by the most accurate Nose-Hoover thermostat and used for the rest of the simulation protocol. The long-range electrostatic interactions were treated with the particle mesh Ewald (PME) method, while Coulomb and van der Waals interactions were cut off at 1.2 nm. Bond lengths of the atoms were restrained using the Linear Constraint Solver (LINCS) algorithm.

Important distance and dihedral angle measurements were taken using distance, mindist and angle tools available in the GROMACS software package.

References

1. Yeung, Y. Y.; Hong, S.; Corey, E. J., A short enantioselective pathway for the synthesis of the anti-influenza neuramidase inhibitor oseltamivir from 1,3-butadiene and acrylic acid. *J Am Chem Soc* 2006, 128 (19), 6310-1.
2. Zhu, W.; Doubleday, P. F.; Catlin, D. S.; Weerawarna, P. M.; Butrin, A.; Shen, S.; Wawrzak, Z.; Kelleher, N. L.; Liu, D.; Silverman, R. B., A Remarkable Difference That One Fluorine Atom Confers on the Mechanisms of Inactivation of Human Ornithine Aminotransferase by Two Cyclohexene Analogues of gamma-Aminobutyric Acid. *J Am Chem Soc* 2020, 142 (10), 4892-4903.
3. Christensen, E. M.; Patel, S. M.; Korasick, D. A.; Campbell, A. C.; Krause, K. L.; Becker, D. F.; Tanner, J. J., Resolving the cofactor-binding site in the proline biosynthetic enzyme human pyrroline-5-carboxylate reductase 1. *J Biol Chem* 2017, 292 (17), 7233-7243.
4. Mascarenhas, R.; Le, H. V.; Clevenger, K. D.; Lehrer, H. J.; Ringe, D.; Kelleher, N. L.; Silverman, R. B.; Liu, D., Selective Targeting by a Mechanism-Based Inactivator against Pyridoxal 5'-Phosphate-Dependent Enzymes: MechanismS of Inactivation and Alternative Turnover. *Biochemistry-Us* 2017, 56 (37), 4951-4961.
5. Churchich, J. E.; Moses, U., 4-Aminobutyrate Aminotransferase—the Presence of Nonequivalent Binding-Sites. *J Biol Chem* 1981, 256 (3), 1101-1104.
6. Lee, H.; Doud, E. H.; Wu, R.; Sanishvili, R.; Juncosa, J. I.; Liu, D. L.; Kelleher, N. L.; Silverman, R. B., Mechanism of Inactivation of gamma-Aminobutyric Acid Aminotransferase by (1S,3S)-3-Amino-4-difluoromethylene-1-cyclopentanoic Acid (CPP-115). *J Am Chem Soc* 2015, 137 (7), 2628-2640.
7. Juncosa, J. I.; Lee, H.; Silverman, R. B., Two continuous coupled assays for ornithine-delta-aminotransferase. *Anal Biochem* 2013, 440 (2), 145-149.
8. Moschitto, M. J.; Doubleday, P. F.; Catlin, D. S.; Kelleher, N. L.; Liu, D.; Silverman, R. B., Mechanism of Inactivation of Ornithine Aminotransferase by (1S,3S)-3-Amino-4-(hexafluoropropan-2-ylidenyl)cyclopentane-1-carboxylic Acid. *J Am Chem Soc* 2019, 141 (27), 10711-10721.
9. Juncosa, J. I.; Takaya, K.; Le, H. V.; Moschitto, M. J.; Weerawarna, P. M.; Mascarenhas, R.; Liu, D. L.; Dewey, S. L.; Silverman, R. B., Design and Mechanism of (S)-3-Amino-4-(difluoromethylenyl)cyclopent-1-ene-1-carboxylic Acid, a Highly Potent gamma-Aminobutyric Acid Aminotransferase Inactivator for the Treatment of Addiction. *J Am Chem Soc* 2018, 140 (6), 2151-2164.
10. Winter, G.; Waterman, D. G.; Parkhurst, J. M.; Brewster, A. S.; Gildea, R. J.; Gerstel, M.; Fuentes-Montero, L.; Vollmar, M.; Michels-Clark, T.; Young, I. D.; Sauter, N. K.; Evans, G., DIALS: implementation and evaluation of a new integration package. *Acta Crystallogr D* 2018, 74, 85-97.
11. Evans, P., Scaling and assessment of data quality. *Acta Crystallogr D* 2006, 62, 72-82.
12. Grosse-Kunstleve, R. W.; Sauter, N. K.; Moriarty, N. W.; Adams, P. D., The Computational Crystallography Toolbox: crystallographic algorithms in a reusable software framework. *J Appl Crystallogr* 2002, 35, 126-136.
13. Mccoy, A. J.; Grosse-Kunstleve, R. W.; Adams, P. D.; Winn, M. D.; Storoni, L. C.; Read, R. J., Phaser crystallographic software. *J Appl Crystallogr* 2007, 40, 658-674.
14. Shen, B. W.; Hennig, M.; Hohenester, E.; Jansonius, J. N.; Schirmer, T., Crystal structure of human recombinant ornithine aminotransferase. *J Mol Biol* 1998, 277 (1), 81-102.
15. Emsley, P.; Lohkamp, B.; Scott, W. G.; Cowtan, K., Features and development of Coot. *Acta Crystallographica Section D—Biological Crystallography* 2010, 66, 486-501.
16. Liebschner, D.; Afonine, P. V.; Baker, M. L.; Bunkoczi, G.; Chen, V. B.; Croll, T. I.; Hintze, B.; Hung, L. W.; Jain, S.; McCoy, A. J.; Moriarty, N. W.; Oeffner, R. D.; Poon, B. K.; Prisant, M. G.; Read, R. J.; Richardson, J. S.; Richardson, D. C.; Sammito, M. D.; Sobolev, O. V.; Stockwell, D. H.; Terwilliger, T. C.; Urzhumtsev, A. G.; Videau, L. L.; Williams, C. J.; Adams, P. D., Macromolecular structure determination using X-rays, neutrons and electrons: recent developments in Phenix. *Acta Crystallogr D* 2019, 75, 861-877.
17. Pettersen, E. F.; Goddard, T. D.; Huang, C. C.; Couch, G. S.; Greenblatt, D. M.; Meng, E. C.; Ferrin, T. E., UCSF chimera—A visualization system for exploratory research and analysis. *J Comput Chem* 2004, 25 (13), 1605-1612.
18. Earley, L.; Anderson, L. C.; Bai, D. L.; Mullen, C.; Syka, J. E.; English, A. M.; Dunyach, J. J.; Stafford, G. C., Jr.; Shabanowitz, J.; Hunt, D. F.; Compton, P. D., Front-end electron transfer dissociation: a new ionization source. *Anal Chem* 2013, 85 (17), 8385-90.
19. Fellers, R. T.; Greer, J. B.; Early, B. P.; Yu, X.; LeDuc, R. D.; Kelleher, N. L.; Thomas, P. M., ProSight Lite: graphical software to analyze top-down mass spectrometry data. *Proteomics* 2015, 15 (7), 1235-8.
20. Niedermeyer, T. H.; Strohalm, M., mMass as a software tool for the annotation of cyclic peptide tandem mass spectra. *Plos One* 2012, 7 (9), e44913.
21. Marty, M. T.; Baldwin, A. J.; Marklund, E. G.; Hochberg, G. K.; Benesch, J. L.; Robinson, C. V., Bayesian deconvolution of mass and ion mobility spectra: from binary interactions to polydisperse ensembles. *Anal Chem* 2015, 87 (8), 4370-6.
22. Heath, T. K.; Lutz, M. R.; Reidl, C. T.; Guzman, E. R.; Herbert, C. A.; Nocek, B. P.; Holz, R. C.; Olsen, K. W.; Ballicora, M. A.; Becker, D. P., Practical spectrophotometric assay for the dapE-encoded N-succinyl-L,L-diaminopimelic acid desuccinylase, a potential antibiotic target. *Plos One* 2018, 13 (4).
23. Vilar, S.; Cozza, G.; Moro, S., Medicinal Chemistry and the Molecular Operating Environment (MOE): Application of QSAR and Molecular Docking to Drug Discovery. *Curr Top Med Chem* 2008, 8 (18), 1555-1572.
24. Boyd, S., Molecular operating environment. *Chem World-Uk* 2005, 2 (9), 66-66.
25. Morris, G. M.; Huey, R.; Lindstrom, W.; Sanner, M. F.; Belew, R. K.; Goodsell, D. S.; Olson, A. J., AutoDock4 and AutoDockTools4: Automated Docking with Selective Receptor Flexibility. *J Comput Chem* 2009, 30 (16), 2785-2791.
26. Wang, J. M.; Wang, W.; Kollman, P. A.; Case, D. A., Automatic atom type and bond type perception in molecular mechanical calculations. *J Mol Graph Model* 2006, 25 (2), 247-260.

27. Sousa da Silva, A. W.; Vranken, W. F., ACPYPE—AnteChamber PYthon Parser interfacE. *BMC Res Notes* 2012, 5, 367.

28. Pronk, S.; Pall, S.; Schulz, R.; Larsson, P.; Bjelkmar, P.; Apostolov, R.; Shirts, M. R.; Smith, J. C.; Kasson, P. M.; van der Spoel, D.; Hess, B.; Lindahl, E., GROMACS 4.5: a high-throughput and highly parallel open source molecular simulation toolkit. *Bioinformatics* 2013, 29 (7), 845-54.

29. Towns, J.; Cockerill, T.; Dahan, M.; Foster, I.; Gaither, K.; Grimshaw, A.; Hazlewood, V.; Lathrop, S.; Lifka, D.; Peterson, G. D.; Roskies, R.; Scott, J. R.; Wilkins-Diehr, N., XSEDE: Accelerating Scientific Discovery. *Comput Sci Eng* 2014, 16 (5), 62-74.

Example 3

TABLE 6 in vivo PK profiles of Compound 14 and Compound 9

| Cpd | Route | Dose (mg/kg) | $T_{max}$ (hr) | $^{a}C_0/C_{max}$ (ng/mL) | $AUC_{last}$ (hr*ng/mL) | $AUC_{inf}$ (hr*ng/mL) | $T_{1/2}$ (hr) | CL (mL/min/kg) | $V_{SS}$ (L/kg) | % F | B/P ratio @0.25 h |
|---|---|---|---|---|---|---|---|---|---|---|---|
| 9 | IV | 3 | — | 2376.08 | 634.12 | 653.80 | 0.51 | 76.48 | 1.75 | — | 0.05 |
| | PO | 10 | 0.25 | 1575.74 | 881.20 | 1006.60 | — | — | — | 42 | 0.03 |
| 14 | IV | 10 | — | 14753.20 | 2467.95 | 2492.65 | 0.16 | 66.86 | 0.64 | — | 0.05 |
| | PO | 30 | 0.25 | 3432.69 | 4258.71 | 4332.80 | — | — | — | 58 | 0.01 |

In accordance with this disclosure, various other compounds, varied structurally, stereochemically and/or configurationally, are available through such incorporated synthetic procedures and techniques or straight-forward modifications thereof, such modifications as would also be known and understood by those skilled in the art and made aware of this invention, such procedures, techniques and modifications limited only by the commercial or synthetic availability of any corresponding reagent or starting material.

We claim:

1. A compound of the following formula or a dissociated form, a non-protonated form, a zwitterion form, or a salt thereof:

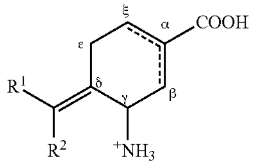

wherein a double bond is optionally present between the α and ζ carbons or wherein a double bond is optionally present between the α and β carbons, and wherein each of $R^1$ and $R^2$ is independently selected from F, Cl, Br, and I.

2. The compound of claim 1 in zwitterion form comprising an ammonium moiety and a carboxylate moiety.

3. The compound of claim 1, wherein no double bond is present between the α and ζ carbons and between the α and β carbons.

4. The compound of claim 1, wherein the double bond is present between the α and ζ carbons.

5. The compound of claim 1, wherein the double bond is present between the α and β carbons.

6. The compound of claim 1, wherein $R^1$ and $R^2$ are F.

7. The compound of claim 1 of a formula:

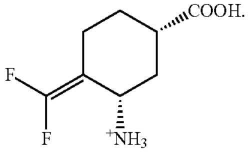

8. The compound of claim 1 of a formula:

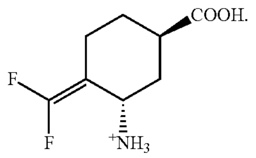

9. The compound of claim 1 of a formula:

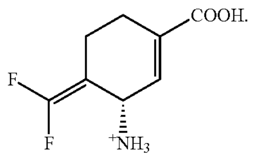

10. The compound of claim 1 of a formula:

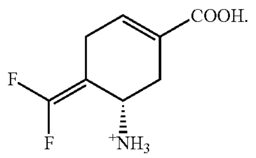

11. The compound of claim 1, wherein the compound is a salt comprising a substituent selected from an ammonium substituent, a carboxylate substituent, and a combination thereof.

12. The compound of claim 11, wherein the ammonium salt has a counter ion that is the conjugate base of a protic acid.

13. A pharmaceutical composition comprising the compound of claim 1 and a pharmaceutically suitable carrier, diluent, or excipient.

14. A method of modulating human ornithine aminotransferase (hOAT) activity, the method comprising contacting the compound of claim 1 with a medium comprising hOAT, wherein the compound is present in an amount sufficient to modulate hOAT activity.

15. The method of claim 14, wherein the contact is in vivo.

16. A method of reducing activity of an hOAT expressed by a human cancer, the method comprising contacting the compound of claim 1 with the cancer expressing an hOAT, wherein the compound is present in an amount that is effective to reduce hOAT activity.

17. A method for treating cancer in a subject in need thereof, the method comprising administering to the subject a therapeutically effective amount of the compound of claim 1, wherein the cancer is characterized by expression or overexpression of human ornithine aminotransferase (hOAT).

18. The method of claim 17, wherein the cancer is hepatocellular carcinoma (HCC), non-small cell lung cancer (NSCLC), or colorectal cancer.

* * * * *